US007803906B2

(12) United States Patent
Al-Mahmood et al.

(10) Patent No.: US 7,803,906 B2
(45) Date of Patent: Sep. 28, 2010

(54) COMPOSITION COMPRISING AN ANGIOGENESIS RELATED PROTEIN

(75) Inventors: Salman Al-Mahmood, Paris (FR); Sylvie Colin, Paris (FR); Christophe Schneider, Reims (FR)

(73) Assignee: Gene Signal International SA, Epalinges (CH)

( * ) Notice: Subject to any disclaimer, the term of this patent is extended or adjusted under 35 U.S.C. 154(b) by 561 days.

(21) Appl. No.: 10/947,476

(22) Filed: Sep. 22, 2004

(65) Prior Publication Data
US 2005/0119215 A1 Jun. 2, 2005

Related U.S. Application Data

(63) Continuation of application No. PCT/FR03/00912, filed on Mar. 21, 2003.

(30) Foreign Application Priority Data

Mar. 22, 2002 (FR) .................................. 02 03655

(51) Int. Cl.
C07K 14/00 (2006.01)
A61K 38/16 (2006.01)
(52) U.S. Cl. ...................................... 530/350; 530/380
(58) Field of Classification Search ................ 530/350, 530/380
See application file for complete search history.

(56) References Cited

U.S. PATENT DOCUMENTS

| 5,747,660 | A | 5/1998 | Orlicky |
| 7,034,132 | B2 * | 4/2006 | Anderson et al. ............. 536/23.1 |
| 2002/0137081 | A1 | 9/2002 | Bandman |

| 2007/0042945 | A1 * | 2/2007 | Bodary et al. ................. 514/12 |

FOREIGN PATENT DOCUMENTS

| WO | WO 98-21333 | 5/1998 |
| WO | WO 99/00498 | 1/1999 |
| WO | WO 01/21831 | 3/2001 |
| WO | WO 01/60860 | 8/2001 |
| WO | WO 02/34783 | 5/2002 |
| WO | WO 0234783 A2 * | 5/2002 |
| WO | WO 03/074073 | 9/2003 |

OTHER PUBLICATIONS

Genbank Accession No. BAA92674, Mar. 14, 2000.*
Genbank Accession No. Q9H3U3, (May 1998).*
XP-002219162; Database accession No. ABV26916; Sep. 16, 2002.
XP 002219161; The Major CD9 and CD81 Molecular Partner; Journal of Biological Chemistry; vol. 276, No. 17, pp. 14329-14337.
XP 002219163; Database accession No. AI953818; Abstract; Aug. 23, 1999.

(Continued)

Primary Examiner—J. E Angell
(74) Attorney, Agent, or Firm—Young & Thompson

(57) ABSTRACT

Nucleotide sequences and the corresponding polypeptide sequences implicated in the regulation of angiogenesis are identified. The nucleotide and polypeptide sequences, or pharmaceutical compositions made from such sequences, can be used in the clinical study of the angiogenesis process, the prognosis, diagnosis and treatment of pathologies linked to angiogenesis, and in the implementation of pharmacological, pharmacogenomic and drug identification trials.

6 Claims, 1 Drawing Sheet

OTHER PUBLICATIONS

XP-002219164; Database accession No. BC022235; Abstract; Feb. 6, 2002.
XP 002219166; Database accession No. AB037857; Abstract; Mar. 14, 2000.
XP 002219165; Database accession No. U47120; Abstract; Mar. 18, 1996.
XP-002269996; Database accession No. ABV25139; Abstract; Sep. 16, 2002.
XP 002269997; Database accession No. AF247704; Abstract; Sep. 5, 2000.
XP 002269998; Database accession No. ABV23250; Abstract; Sep. 16, 2002.
XP-002269999; Database accession No. AA486235; Abstract; Jun. 27, 1997.
XP 002270000; Database accession No. U91543; Abstract; Jul. 10, 1998.
XP 002270001; Database accession No. ABX63370; Abstract; Feb. 25, 2003.
XP-002270002; Database accession No. BC001571; Abstract; Oct. 25, 2001.
XP 002270003; Database accession No. BF980038; Abstract; Jan. 24, 2001.

* cited by examiner

SEQUENCE LISTING

<160> NUMBER OF SEQ ID NOS: 34

<210> SEQ ID NO 1
<211> LENGTH: 6160
<212> TYPE: DNA
<213> ORGANISM: Homo sapiens
<300> PUBLICATION INFORMATION:
<308> DATABASE ACCESSION NUMBER: GenBank/AB037857
<309> DATABASE ENTRY DATE: 2000-03-14
<313> RELEVANT RESIDUES: (1)..(6160)

<400> SEQUENCE: 1

```
ctcgcgagga gagcggagca ggcgcgcggc ccaggcggag gagcgccgac tctggagcag      60
ccggagctgg aagaggagga ggaggagagg cggcggggaa ggaggaggag ggggagagtc     120
gctcccgccg ggcgagcatg gggcgcctgg cctcgaggcc gctgctgctg gcgctcctgt     180
cgttggctct ttgccgaggg cgtgtggtga gagtccccac agcgaccctg gttcgagtgg     240
tgggcactga gctggtcatc ccctgcaacg tcagtgacta tgatggcccc agcgagcaaa     300
actttgactg gagcttctca tctttgggga gcagctttgt ggagcttgca agcacctggg     360
aggtggggtt cccagcccag ctgtaccagg agcggctgca gaggggcgag atcctgttaa     420
ggcggactgc caacgacgcc gtggagctcc acataaagaa cgtccagcct tcagaccaag     480
gccactacaa atgttcaacc cccagcacag atgccactgt ccagggaaac tatgaggaca     540
cagtgcaggt taaagtgctg gccgactccc tgcacgtggg ccccagcgcg cggccccgc      600 cgagcctgag cctgcgggag ggggagccct tcgagctgcg ctgcactgcc gcctccgcct     660
cgccgctgca cacgcacctg gcgctgctgt gggaggtgca ccgcggcccg gccaggcgga     720
gcgtcctcgc cctgacccac gagggcaggt tccacccggg cctggggtac gagcagcgct     780
accacagtgg ggacgtgcgc ctcgacaccg tgggcagcga cgcctaccgc ctctcagtgt     840
cccgggctct gtctgccgac cagggctcct acaggtgtat cgtcagcgag tggatcgccg     900
agcagggcaa ctggcaggaa atccaagaaa aggccgtgga agttgccacc gtggtgatcc     960
agccatcagt tctgcgagca gctgtgccca agaatgtgtc tgtggctgaa ggaaaggaac    1020
tggacctgac ctgtaacatc acaacagacc gagccgatga cgtccggccc gaggtgacgt    1080
ggtccttcag caggatgcct gacagcaccc tacctggctc ccgcgtgttg gcgcggcttg    1140
accgtgattc cctggtgcac agctcgcctc atgttgcttt gagtcatgtg gatgcacgct    1200
```

-continued

```
cctaccattt actggttcgg gatgttagca aagaaaactc tggctactat tactgccacg    1260
tgtccctgtg ggcacccgga cacaacagga gctggcacaa agtggcagag gccgtgtctt    1320
ccccagctgg tgtgggtgtg acctggctag aaccagacta ccaggtgtac ctgaatgctt    1380
ccaaggtccc cgggtttgcg gatgaccca cagagctggc atgccgggtg gtggacacga     1440
agagtgggga ggcgaatgtc cgattcacgg tttcgtggta ctacaggatg aaccggcgca    1500
gcgacaatgt ggtgaccagc gagctgcttg cagtcatgga cggggactgg acgctaaaat    1560
atggagagag gagcaagcag cgggcccagg atggagactt tattttttct aaggaacata    1620
cagacacgtt caatttccgg atccaaagga ctacagagga agacagaggc aattattact    1680
gtgttgtgtc tgcctggacc aaacagcgga acaacagctg ggtgaaaagc aaggatgtct    1740
tctccaagcc tgttaacata tttttgggcat tagaagattc cgtgcttgtg gtgaaggcga    1800
ggcagccaaa gccttctttt gctgccgaa atacatttga gatgacttgc aaagtatctt     1860
ccaagaatat taagtcgcca cgctactctg ttctcatcat ggctgagaag cctgtcggcg    1920
acctctccag tcccaatgaa acgaagtaca tcatctctct ggaccaggat tctgtggtga    1980
agctggagaa ttggacagat gcatcacggg tggatggcgt tgttttagaa aaagtgcagg    2040
aggatgagtt ccgctatcga atgtaccaga ctcaggtctc agacgcaggg ctgtaccgct    2100
gcatggtgac agcctggtct cctgtcaggg gcagcctttg gcgagaagca gcaaccagtc    2160
tctccaatcc tattgagata gacttccaaa cctcaggtcc tatatttaat gcttctgtgc    2220
attcagacac accatcagta attcggggag atctgatcaa attgttctgt atcatcactg    2280
tcgagggagc agcactggat ccagatgaca tggccttga tgtgtcctgg tttgcggtgc      2340
actcttttgg cctggacaag gctcctgtgc tcctgtcttc cctggatcgg aagggcatcg    2400
tgaccacctc ccggagggac tggaagagcg acctcagcct ggagcgcgtg agtgtgctgg    2460
aattcttgct gcaagtgcat ggctccgagg accaggactt tggcaactac tactgttccg    2520
tgactccatg ggtgaagtca ccaacaggtt cctggcagaa ggaggcagag atccactcca    2580
agcccgtttt tataactgtg aagatggatg tgctgaacgc cttcaagtat cccttgctga    2640
tcggcgtcgg tctgtccacg gtcatcgggc tcctgtcctg tctcatcggg tactgcagct    2700
cccactggtt ttgtaagaag gaggttcagg agacacggcg cgagcgccgc aggctcatgt    2760
cgatggagat ggactaggct ggcccgggag gggagtgaca gagggacgtt ctaggagcaa    2820
ttggggcaag aagaggacag tgatatttta aaacaaagtg tgttacacta aaaaccagtc    2880
ctctctaatc tcaggtggga cttggcgctc tctcttttct gcatgtcaag ttctgagcgc    2940
ggacatgttt accagcacac ggctcttctt cccacggcac tttctgatgt aacaatcgag    3000
tgtgtgtttt cccaactgca gcttttaat ggttaacctt catctaattt ttttctccc      3060 actggtttat agatcctctg acttgtgtgt gtttatagct tttgtttcgc ggggttgtgg    3120
tgaggaaggg gtgatggcat gcggagttct ttatcttcag tgagaatgtg cctgcccgcc    3180
tgagagccag cttccgcgtt ggaggcacgt gttcagagag ctgctgagcg ccaccctcta    3240
cccggctgac agacaacaca gacctgtgcc gaaggctaat ttgtggcttt tacgaccta     3300 ccccacccc tgttttcagg ggtttagact acatttgaaa tccaaacttg gagtatataa     3360
cttcttattg agcccaactg ctttttttt ttttttttt gcttctctgc ccttttcca      3420 tttcttttgt atttgttttc tgtgagagca ctgaaatggc agccctggaa tctacaattt    3480
ggctctccac tgagcacctt atcttgccac cttagcctta agaatgaata tgaagaaaaa    3540
```

```
tacacagcca cctctgtcca gggcagtaag aagggctgca aggaagggga ggatggggac   3600
aaggaaagga tcagatacct gctccagtag ttgtgaggcc actgtgtctc aggggactcc   3660
aggaggagca gaagagggat cccacgaagt tattcttacg cagctggggc caggagggtc   3720
agagtggtgc caggtgcaag ttaggctaaa gaagccacca ctattcctct ctcttgccca   3780
ttgtgggggg caaaggcatt ggtcaccaag agtcttgcag ggggacccac agatatgcca   3840
tgtccttcac acgtgcttgg gctccttaac ctgaaggcaa attgctactt gcaagactga   3900
ctgacttcaa ggaatcagaa attacctaga agcaccatgt ttttctatg acctttcag    3960 tccttcaggt cattttaagg tccactgcag ggggttagtg agaaagggta tactttgtgg   4020
tatgttttgc tttcctaata gggacatgaa ggaaacccag caatttgctg ttatgtgaat   4080
ggcctgtaga gcagagtcaa gagcggtgtg ctttgcccga ctgctcccat caggaatagg   4140
agagtagaca gagatcttcc acatcccagg cttctgctgc tgctttaaaa gctctgtcct   4200
tggagcctcc cgctccctga agtgtctcgc ccctgcaca gcactggcct ttcggaagca    4260
tcccagtagg gttttctgag gctcgctggt gactcatgcc ctaattgcaa tcctctgctt   4320
ttatcttgac tttgaaggat ctaacactgc tctctcttcc aaaggggaaa aaagattca    4380 tttgttttga gcaataaact aatacaaaat gatggccatt catgtgcagc tctttgtcac   4440
catgggccgg atgagttgtg ctcctcctgg ctcaccatt ccccctgctc cccacagcc     4500 ggttctgcac ttatcaccga gtcgcccctg gaagcagatt cccattgagt ttcccacc     4560 aaggggacca tgcacatggt agaaacatta gattctgcat tgacagtagc ctttccttgg   4620
cccgggcctg tggtgggaag acgggcaaca agtatacccc accagggcct gagtgactag   4680
aggaagagga cgaggccttg ttggcactag atttgggtat tttctgcatg tcataacata   4740
tcctaactgc tatttcagaa gaggcagctt gtaggtgatt gtacaagtga gaattaaaga   4800
gagaacagat atttaaacag gtgctgtatt agtaacagcc agtgcccttt cagcccttgc   4860
atctattaaa aggagattca ggattttatt ggcacaggcc cttcttagta ggaagaaagg   4920
gtgcttagct ttggacctga ccgggtgtgt gtaaaaccat ggactgagtc acagcagaca   4980
ctcgatggtg gtaaatgtga tgggtgctta cacactgtac cttttccttt catactgatg   5040
ctgcagttca gggctggagt tgttaaggca ttgacctcca cccacctgcc ccatgtccac   5100
tgggctgccc aagctgcatg tcacctgagg gctggcagga agggcgaga aatcccaggg    5160 cattgtacca aggacctagt tccttctagg gatataaatt tccaggaatg tgtatttta    5220 atgtggtgag atgcactctt ttgttgtacc aaatagggct cccacccca cccctgcgac    5280 aagtgctctt ctagaacagg ttcctaccag cagcactggt gtgaatgaaa gagagaccca   5340
gccgcgtctc acacaggtgg aattgcactt cttaacaaaa aggaacttta taaagtttg    5400 ggattttttt tcctaatcat aaaaatagcc ccagaaagag cctaagctat gttcagatag   5460
aagcctcgaa attcctgtaa attgtttact ttatgatgtt tacatacacg tttcactttg   5520
aaaaaaaatg caaatcgact ttttaacaac tgttgagatg tttcatggga cagtagaact   5580
ctgactcacc aactgggcta aatttttaatt taaaaatgta tttatttgag tgtctttccc   5640
cccctcaccc tcaccatctg aggggctccc tgagatcttg gtagaggagg cccctcctgc   5700
ccagaccttc gtttgtttcc ccggtggccc ttgcttcttg ctttgcagac tgcctgcagc   5760
catgattttg tcactgacat ctgtgagcca aagactgagc cttttggca ggaataataa    5820 gcaatactac acaacttgct actttcagaa aactttttt tagcttcacc gatgacaaca    5880
gaggaagaag ggaactggga tttgggtaag ttctcctcca ctgtttgacc aaattctcag   5940
```

| | |
|---|---:|
| tgataaatat gtgtgcagat ccctagaaga gaaaacgctg actttctttt taagtgtggc | 6000 |
| acataaggat ctgcagaatt ttccgtagac aaagaaagga tcttgtgtat ttttgtccat | 6060 |
| atccaatgtt atatgaacta attgtattgt tttatactgt gaccacaaat attatgcaat | 6120 |
| gcaccatttg ttttttattt cattaaagga agtttaattt | 6160 |

```
<210> SEQ ID NO 2
<211> LENGTH: 3266
<212> TYPE: DNA
<213> ORGANISM: Homo sapiens
<300> PUBLICATION INFORMATION:
<308> DATABASE ACCESSION NUMBER: GenBank/AF247704
<309> DATABASE ENTRY DATE: 2000-09-02
<313> RELEVANT RESIDUES: (1)..(3266)

<400> SEQUENCE: 2
```

| | |
|---|---:|
| gcggtgcggg ccgggcgggt gcattcaggc caaggcgggg ccgccgggat gctcagggtt | 60 |
| ccggagccgc ggcccgggga ggcgaaagcg gaggggcccg cgccgccgac cccgtccaag | 120 |
| ccgctcacgt ccttcctcat ccaggacatc ctgcgggacg gcgcgcagcg gcaaggcggc | 180 |
| cgcacgagca gccagagaca gcgcgacccg gagccggagc cagagccaga gccagaggga | 240 |
| ggacgcagcc gcgccgggc gcagaacgac cagctgagca ccgggccccg cgccgcgccg | 300 |
| gaggaggccg agacgctggc agagaccgag ccagaaaggc acttggggtc ttatctgttg | 360 |
| gactctgaaa acacttcagg cgcccttcca aggcttcccc aaaccctaa gcagccgcag | 420 |
| aagcgctccc gagctgcctt ctcccacact caggtgatcg agttggagag gaagttcagc | 480 |
| catcagaagt acctgtcagc ccctgaacgg gcccacctgg ccaagaacct caagctcacg | 540 |
| gagacccaag tgaagatatg gttccagaac agacgctata agactaagcg aaagcagctc | 600 |
| tcctcggagc tgggagactt ggagaagcac tcctctttgc cggccctgaa agaggaggcc | 660 |
| ttctcccggg cctcccctgg ctccgtgtat aacagctatc cttactaccc ataccctgtac | 720 |
| tgcgtgggca gctggagccc agcttttttgg taatgccagc tcaggtgaca accattatga | 780 |
| tcaaaaactg ccttcccccag ggtgtctcat atgaaaagca caaggggcca aggtcaggga | 840 |
| gcaagaggtg tgcacaccaa aactattgga gaattgcgtg gaaatcttca gattcttcac | 900 |
| tggtgagaca atgaaacaac agagacagtg aaagttttaa tacctaagtc attccccccag | 960 |
| tgcatactgt agcgtcaagt ttttgcttct ggctacctgt ttgaagggga gagagggaaa | 1020 |
| atcaagtggt atttttccagc actttgtatg attttggatg agctgtacac ccaaggattc | 1080 |
| tgttctgcaa ctccatcctc ctgtgtcact gaatatcaac tctgaaagag caaacctaac | 1140 |
| aggagaaagg acaaccagga tgaggatgtc accaactgaa ttaaacttaa gtccagaagc | 1200 |
| ctcctgttgg ccttggaata tggccaaggc tctctctgtc cctgtaaaag agaggggcaa | 1260 |
| atagtctcca aagagaacgc cctcatgctc agcacatatt tgcatggaag ggggagatgg | 1320 |
| gtgggaggag atgaaaatat cagcttttct tattcctttt tattccttttt aaaatggtat | 1380 |
| gccaacttaa gtatttacag ggtggcccaa atagaacaag atgcactcgc tgtgatttta | 1440 |
| agacaagctg tataaacaga actccactgc aagagggagg gccgggccag gagaatctcc | 1500 |
| gcttgtccaa gacaggggcc taaggagggt ctccacactg ctgctagggg ctgttgcatt | 1560 |
| tttttattag tagaaagtgg aaaggcctct tctcaacttt tttcccttgg gctggagaat | 1620 |
| ttagaatcag aagtttcctg gagttttcag gctatcatat atactgtatc ctgaaaggca | 1680 |
| acataattct tccttccctc cttttaaaat tttgtgttcc ttttgcagc aattactcac | 1740 |

-continued

```
taaagggctt cattttagtc cagattttta gtctggctgc acctaactta tgcctcgctt    1800
atttagcccg agatccggtc ttttttttt tttttttttc cgtctcccca aagctttatc    1860
tgtcttgact ttttaaaaaa gtttgggggc agattctgaa ttggctaaaa gacatgcatt    1920
tttaaaacta gcaactctta tttctttcct ttaaaaatac atagcattaa atcccaaatc    1980
ctatttaaag acctgacagc ttgagaaggg tcactactgc atttatagga ccttctggtg    2040
gttctgctgt tacgtttgaa gtctgacaat ccttgagaat ctttgcatgc agaggaggta    2100
agaggtattg gattttcaca gagggaagaa cacagcgcag aatgaaggcg caggcttact    2160
gagctgtcca gtggagggct catgggtggg acatggaaaa gaaggcagcc taggccctgg    2220
ggagcccagt ccactgagca agcaagggac tgagtgagcc ttttgcagga aaaggctaag    2280
aaaaaggaaa accattctaa aacacaacaa gaaactgtcc aaatgctttg ggaactgtgt    2340
ttattgccta taatggggtc cccaaaatgg gtaacctaga cttcagagag aatgagcaga    2400
gagcaaagga gaaatctggg ctgtccttcc attttcattc tgttatctca ggtgagctgg    2460
tagaggggag acattagaaa aaatgaaac aacaaaacaa ttactaatga ggtacgctga    2520
ggcctgggag tctcttgagc tccacgactt caaaattaaa atgagccatg agtcaaacca    2580
ctgcaatcca gcctgggcaa cgagcaagac ccagtctcta ctgttggtgg caaaattgcc    2640
aacataagtt aatagaaagt tggccaattt cacccatttt tctgtggttt gggctccaca    2700
ttgcaatgtt caatgccacg tgctgctgac accgaccgga gtactagcca gcacaaaagg    2760
cagggtagcc tgaattgctt tctgctcttt acatttcttt taaaataagc atttagtgct    2820
cagtccctac tgagtactct ttctctcccc tcctctgaat ttaattcttt caacttgcaa    2880
tttgcaaggg ttacacattt cactgtgatg tatattgtgt tgcaaaaaaa aaaaagtgtc    2940
tttgtttaaa attacttggt ttgtgaatcc atcttgcttt ccccattgga actagtcatt    3000
aacccatctc tgaactggta gaaaaacatc tgaagagcta gtctatcagc atctgacagg    3060
tgaattggat ggttctcaga accatttcac ccagacagcc tgtttctatc ctgtttaata    3120
aattagtttg ggttctctac atgcataaca aaccctgctc caatctgtca cataaaagtc    3180
tgtgacttga agtttagtca gcaccccac caaactttat ttttctatgt gttttttgca    3240
acatatgagt gttttgaaaa taaagt                                         3266
```

<210> SEQ ID NO 3  
<211> LENGTH: 6771  
<212> TYPE: DNA  
<213> ORGANISM: Homo sapiens  
<300> PUBLICATION INFORMATION:  
<308> DATABASE ACCESSION NUMBER: GenBank/U91543  
<309> DATABASE ENTRY DATE: 1998-08-04  
<313> RELEVANT RESIDUES: (1)..(6771)

<400> SEQUENCE: 3

```
atatggaggt gaagggtgag atcgggaaac aaagggtatg gcccctagt tcccaaaggg     60 agcagggaga tgggaataga attgaaggta ggttttaggc tacttgggag gaggaatatt    120
taggtaattg tggagacttt ctcctgtgtg atgaaggcgg cagacactgt gatcctgtgg    180
gcaagaagta aaaatgacca gctgaggatt tcttttcctc caggactgtg ttggggtgac    240
aggatgcctg ataaggatga cattcggctg ctgccgtcag cattgggtgt gaagaagaga    300
aaacgaggac ccaagaagca gaaggagaac aagccaggaa accccgaaa acgcaagaag    360 cgtgacagtg aggaggaatt tggttctgag cgagatgagt accggagaa gtcagagagt    420 gggggcagtg aatatggaac cggaccgggt cggaaacgaa gaaggaagca ccgagaaaaa    480
```

-continued

```
aaggagaaga agacaaagcg gcggaaaaag ggggagggag atgggggggca aaagcaagtg      540 gaacagaagt catcagcaac tctgcttctg acctggggcc tggaggatgt ggagcatgtg      600
ttctctgagg aggattacca cacgctcacc aactacaaag ccttcagcca gttcatgagg      660
cccctaattg ctaagaagaa tcctaagatc ccaatgtcta agatgatgac catccttggg      720
gccaaatgga gagagttcag tgccaacaac cccttcaagg ggtcagcagc tgctgtggcg      780
gcggcagcgg cagcagcagc agcagctgta gctgagcagg tgtcagctgc tgtctcgtcg      840
gccaccccca tagcaccctc cggaccccccc gcccttccac caccccctgc tgctgatatc      900
cagcccccac ccatccgaag agccaaaacc aaagagggca aaggtccagg ccataagagg      960
cggagtaaga gcccccgagt gcctgatgga cgcaagaagc ttcggggaaa gaaaatggca     1020
ccactcaaaa taaaactagg gcttctgggt ggcaagagga agaaaggagg ctcgtatgtt     1080
tttcagagcg acgaaggtcc tgaaccagag gctgaggaat cagacctgga cagtggcagt     1140
gtccacagtg cctcaggccg gcctgatggc cctgtccgca ccaagaaact aaagagaggc     1200
cggccaggaa ggaagaagaa gaaggtcctg ggctgtcctg cagtggccgg ggaggaggag     1260
gttgatggct acgagacgga tcaccaggat tactgtgagg tgtgccagca gggtggggaa     1320
attattctgt gtgacacctg ccctcgtgcc taccacctcg tctgccttga tcctgagctt     1380
gaccgggctc cagagggcaa atggagctgc cctcactgtg agaaggaggg ggtccagtgg     1440
gaggccaagg aggaagaaga agaatacgaa gaggagggag aggaagaagg ggagaaggag     1500
gaggaggatg atcacatgga gtactgccgc gtatgcaagg acggcgggga gctcctgtgc     1560
tgtgacgcgt gcatctcctc ctaccacatt cattgtctaa accctcccct gcctgacatt     1620
cccaatggtg aatggctgtg tccccgatgc acatgccccg tgctgaaggg tcgagtgcag     1680
aagatcctac attggcggtg gggggagcca cctgtagcag tgccagcccc tcaacaggca     1740
gatggaaatc cagatgtccc accccccccgt cctcttcaag gcagatcaga gcgagagttc     1800
tttgtcaagt gggtaggact atcctactgg cactgctcct gggccaagga gcttcagctg     1860
gaaatcttcc atttggttat gtatcgaaac taccagcgga agaatgacat ggatgagccc     1920 ccaccectgg actatggctc cggcgaggat gatgggaaga gcgacaagcg taaagtgaaa     1980
gacccgcact atgctgagat ggaggagaag tactatcgtt ttggcatcaa gccagagtgg     2040
atgaccgtcc accgcatcat caaccacagt gtggataaaa agggggaatta ccactatcta     2100 gtaaaatgga gggacttacc atatgaccag tccacgtggg aggaagatga aatgaatatc     2160
cctgaatacg aagaacataa gcaaagctac tggagacacc gagaactaat tatgggggaa     2220
gaccctgccc agccccgcaa gtataagaag aagaagaagg agctacaggg tgatgggcct     2280
cccagttctc ccactaatga tcctaccgtg aaatatgaga ctcagccacg gtttatcaca     2340
gccactggag gcaccctgca catgtatcag ttggaagggc tgaactggct acgcttctcc     2400
tgggcccagg gcactgacac cattctagct gatgagatgg ggctaggcaa gaccatacaa     2460
accatcgtct tcctctactc actctacaag gagggccaca caaaaggtcc cttcctggtg     2520
agtgccccac tctctaccat cattaactgg gagcgggagt tccagatgtg ggcacccaaa     2580
ttctatgtgg tgacatacac gggtgacaag gacagccggg ccatcattcg tgagaatgaa     2640
ttctcctttg aggacaatgc catcaaaggg ggcaagaaag cttttaagat gaagagggag     2700
gcacaggtga agttccatgt tctcctgaca tcgtatgagc tgatcaccat tgatcaggca     2760
gcacttggtt ccatccgctg ggcctgtctt gtggtagatg aggcccatcg actcaagaac     2820
```

```
aaccagtcca agttttcag ggttctcaat ggttacaaga tagatcataa gttgctgctg    2880
acaggaaccc cattgcagaa taatctggag gagctcttcc atctcctgaa cttcctcacc    2940
ccagagagat ttaacaactt ggagggcttc ctggaggagt ttgctgacat atccaaagag    3000
gaccagatca agaaactgca tgatttgctg gggccacaca tgctgcggag actcaaggca    3060
gatgtcttta agaacatgcc agccaagaca gagctcatcg ttcgggtgga gctaagcccc    3120
atgcagaaga aatactacaa atacatcctg actcgaaatt ttgaggcctt gaattcacga    3180
ggtggtggga accaggtgtc gctgcttaat atcatgatgg atcttaagaa gtgctgcaac    3240
catccatacc ttttcccgt ggctgctatg gagtcccca aactcccag tggggcttat    3300 gagggtgggg cacttattaa gtcgtctggg aagctcatgc tgctccagaa gatgctgcga    3360
aagctgaagg agcaaggaca ccgagtgctc atcttctcgc agatgaccaa aatgttagac    3420
ttgcttgagg acttcttaga ctatgaaggc tacaagtatg agcgcatcga tggtggtatc    3480
acgggtgccc tgaggcagga ggccatcgat cggtttaatg ctcctggggc ccaacaattc    3540
tgcttcctcc tgtccacccg agctgggggc ctgggcatca atctggccac tgctgacact    3600
gtcatcatct ttgattctga ctggaacccc cataatgaca tccaggcctt tagccgggct    3660
catcggattg ccaggccaa caaagtgatg atttaccggt ttgtgactcg cgcgtcagtg    3720
gaagagcgaa tcacacaagt ggccaagaga aagatgatgc tgacacacct ggttgtgcgg    3780
cctgggctgg gctccaaggc aggctccatg tccaagcagg agcttgacga cattctcaaa    3840
tttggcactg aagagctatt caaggatgaa aacgaggggg agaacaagga ggaggacagc    3900
agtgtgattc attatgacaa tgaggccatc gctcggctgt tggaccggaa ccaggatgca    3960
actgaggaca ctgacgtgca gaacatgaat gagtatctca gctcccttcaa ggtggcacag    4020 tacgtcgtgc gggaagaaga caagattgag gaaattgagc gagagatcat caagcaggag    4080
gagaatgtgg accctgacta ctgggagaag ctgctgagcc atcactatga gcaacagcag    4140
gaagacctag cccggaatct aggcaagggc aagcgggttc gcaagcaagt taactacaat    4200
gatgctgctc aggaagacca agacaaccag tcagagtact cggtgggttc agaggaggag    4260
gatgaagact tcgatgaacg tcctgaaggg cgtagacagt caaagaggca gctccggaat    4320
gagaaagata agcccactgcc tccactgctg gcccgagtcg ggggcaacat tgaggtgctg    4380
ggcttcaaca cccgtcagcg gaaggctttc ctcaatgctg tgatgcgctg ggggatgcca    4440
ccacaggatg ccttcaccac acagtggctg gtgcgggacc tgaggggcaa gactgagaag    4500
gagtttaagg cctatgtgtc tttgttcatg cgccatctgt gtgagcctgg ggcagacggc    4560
tctgaaacct ttgccgatgg ggtccctcgg gagggactga gtcgccagca ggtgttgacc    4620
cgcattggag tcatgtctct cgtcaaaaag aaggtgcagg agtttgagca catcaatggg    4680
cgttggtcaa tgccggaact gatgcctgac cccagcgccg attctaagcg ctcctccaga    4740
gcctcctctc ctaccaaaac gtctcccacc actcctgagg cttctgctac caacagtccc    4800
tgcacctcta aacctgctac tccagctcca agtgagaaag gagaaggcat aaggacacct    4860
cttgagaagg aggaagctga aaaccaggag gaaaagccag agaagaacag cagaattggg    4920
gagaagatgg agacagaggc tgatgccccc agcccagccc catcacttgg ggagcggctg    4980
gagccaagga agattcctct agaggatgag gtgccagggg tgcctggaga gatggagcct    5040
gaacctgggt accgtgggga cagagagaag tcagccacag agtcgacgcc aggagaaagg    5100
ggggaggaga agccgttgga tggacaggaa cacaggggaga ggccgagggg ggaaacaggg    5160
gatttgggca agagagaaga tgtaaaaggt gaccgggagc ttcgaccagg gcctcgagat    5220
```

-continued

| | |
|---|---|
| gagccacggt ccaatgggcg acgagaggaa aagacagaga accccggtt catgttcaat | 5280 |
| atcgccgatg gtggcttcac agagcttcac acactgtggc agaatgagga acgggcagct | 5340 |
| atttcctcgg ggaaactcaa tgagatctgg cacagaagac atgactattg cttctggct | 5400 |
| gggattgtcc tccatggcta tgcacggtgg caggacatcc agaatgatgc tcaatttgcc | 5460 |
| attatcaacg agccatttaa aactgaagcc ataaggggga actttctgga gatgaaaaat | 5520 |
| aagttcctgg cccggaggtt caagctcctg gagcaggcgc tggtgattga ggagcagctg | 5580 |
| cggcgggcgg cctacctgaa cctgtcgcag gagccggcgc accccgccat ggccctccac | 5640 |
| gcccgcttcg ccgaggccga gtgcctggcc gagagccacc agcacctctc caaggagtcg | 5700 |
| ctggcgggga acaagccggc caacgccgtc ctgcacaagg ttctgaacca gctggaggag | 5760 |
| ttgctgagcg acatgaaggc ggacgtgacc cgcctgccag ccacgctgtc ccgaataccc | 5820 |
| cccatcgcag cccgccttca gatgtccgag cgcagcatcc tcagccggct ggccagcaag | 5880 |
| ggcacggagc ctcaccccac accggcctac ccgccgggtc cctacgctac acctccgggg | 5940 |
| tacggggcgg ccttcagcgc cgcacccgta ggggccctgg ccgccgcagg cgccaattac | 6000 |
| agccagatgc ctgcagggtc cttcatcaca gccgccacca acgccctcc agtgcttgtg | 6060 |
| aagaaggaga aggaaatggt gggggcattg gtgtcagacg ggctggatcg gaaggagccc | 6120 |
| cgagccgggg aggtgatctg tatagacgac tgactggatc ccaggcctgc ccttcaccca | 6180 |
| ggccccgtcc ccgaggccga cccccagctc aagcgctggg gcctgctgcc agccctccac | 6240 |
| cttcccacc ccttgggcca tcactgggct aggaacccct tgcccctct ctgcagctcc | 6300 |
| tctcttcaag aagggccctt tgtctttctc cactcccaca cacctttccc accaagcctt | 6360 |
| gaagactgtg ctggtgagaa aagtctgggt tgggagatgg ctgcagggt cttccaagta | 6420 |
| ccttcctccc acactgccaa gtatacacaa cttcccagta aatggttgtg gggaggaaag | 6480 |
| aggtggagcc tccccagccg tttccctgca gaatcagctc tgtctcatgt ggaagtggag | 6540 |
| aatcagcctt gcctggcctt taggaacttt tgtggggaag agagctttga agagaggagg | 6600 |
| gggactttag agagggatga aaatgagccc tgggagggag gaagggacga ggagggtgg | 6660 |
| ctgcatgtta ccgtccccta cctctcccca cgtggagggt ggagcagtta tgaggagga | 6720 |
| agtcaactgc tgttcagcct cagaataaag gtgccgttca ctggctcagt t | 6771 |

<210> SEQ ID NO 4
<211> LENGTH: 3041
<212> TYPE: DNA
<213> ORGANISM: Homo sapiens
<300> PUBLICATION INFORMATION:
<308> DATABASE ACCESSION NUMBER: GenBank/BC001571
<309> DATABASE ENTRY DATE: 2001-10-29
<313> RELEVANT RESIDUES: (1)..(3041)

<400> SEQUENCE: 4

| | |
|---|---|
| gtcagggccc tgcggtgtga ctcgcgggct cagctggtcc ggccgtagca cctccgcgcc | 60 |
| gtcgccatgt cgcggttttt caccaccggt tcggacagcg agtccgagtc gtccttgtcc | 120 |
| ggggaggagc tcgtcaccaa acctgtcgga ggcaactatg gcaaacagcc attgttgctg | 180 |
| agcgaggatg aagaagatac caagagagtt gtccgcagtg ccaaggacaa gagggtttgag | 240 |
| gagctgacca accttatccg gaccatccgt aatgccatga agattcgtga tgtcaccaag | 300 |
| tgcctggaag agtttgagct cctgggaaaa gcatatggga aggccaaaag cattgtggac | 360 |
| aaagaaggtg tccccggtt ctatatccgc atcctggctg acctagagga ctatcttaat | 420 |

-continued

```
gagctttggg aagataagga agggaagaag aagatgaaca agaacaatgc caaggctctg    480
agcaccttgc gtcagaagat ccgaaaatac aaccgtgatt tcgagtccca tatcacaagc    540
tacaagcaga accccgagca gtctgcggat gaagatgctg agaaaaatga ggaggattca    600
gaaggctctt cagatgagga tgaggatgag gacggagtca gtgctgcaac tttcttgaag    660
aagaaatcag aagctccttc tggggagagt cgcaagttcc tcaaaaagat ggatgatgaa    720
gatgaggact cagaagattc cgaagatgat gaagactggg acacaggttc cacatcttcc    780
gattccgact cagaggagga agaagggaaa caaaccgcgc tggcctcaag atttcttaaa    840
aaggcaccca ccacagatga ggacaagaag gcagccgaga agaaacggga ggacaaagct    900
aagaagaagc acgacaggaa atccaagcgc ctggatgagg aggaggagga caatgaaggc    960
ggggagtggg aaagggtccg gggcggagtg ccgttggtta aggagaagcc aaaaatgttt   1020
gccaagggaa ctgagatcac ccatgctgtt gttatcaaga aactgaatga gatcctacag   1080
gcacgaggca agaagggaac tgatcgtgct gcccagattg agctgctgca actgctggtt   1140
cagattgcag cggaaaacaa cctgggagag ggcgtcattg tcaagatcaa gttcaatatc   1200
atcgcctctc tctatgacta caaccccaac ctggcaacct acatgaagcc agagatgtgg   1260
gggaagtgcc tggactgcat caatgagctg atggatatcc tgtttgcaaa tcccaacatt   1320
tttgttggag agaatattct ggaagagagt gagaacctgc acaacgctga ccagccactg   1380
cgtgtccgtg gctgcatcct aactctggtg gaacgaatgg atgaagaatt taccaaaata   1440
atgcaaaata ctgaccctca ctcccaagag tacgtggagc acttgaagga tgaggcccag   1500
gtgtgtgcca tcatcgagcg tgtgcagcgc tacctggagg agaagggcac taccgaggag   1560
gtctgccgca tctacctgct gcgcatcctg cacacctact acaagtttga ttacaaggcc   1620
catcagcgac agctgacccc gcctgagggc tcctcaaagt ctgagcaaga ccaggcagaa   1680
aatgagggcg aggactcggc tgtgttgatg gagagactgt gcaagtacat ctacgccaag   1740
gaccgcacag accggatccg cacatgtgcc atcctctgcc acatctacca ccatgctctg   1800
cactcgcgct ggtaccaggc ccgcgacctc atgctcatga gccacttgca ggacaacatt   1860
cagcatgcag acccgccagt gcagatcctt acaaccgca ccatggtgca gctgggcatc   1920
tgtgccttcc gccaaggcct gaccaaggac gcacacaacg ccctgctgga catccagtcg   1980
agtggccgag ccaaggagct tctgggccag ggcctgctgc tgcgcagcct gcaggagcgc   2040
aaccaggagc aggagaaggt ggagcggcgc cgtcaggtcc ccttccacct gcacatcaac   2100
ctggagctgc tggagtgtgt ctacctggtg tctgccatgc tcctggagat cccctacatg   2160
gccgcccatg agagcgatgc ccgccgacgc atgatcagca agcagttcca ccaccagctg   2220
cgcgtgggcg agcgacagcc cctgctgggt ccccctgagt ccatgcggga acatgtggtc   2280
gctgcctcca aggccatgaa gatgggtgac tggaagacct gtcacagttt tatcatcaat   2340
gagaagatga atgggaaagt gtgggaccttt tccccgagg ctgacaaagt ccgcaccatg   2400
ctggttagga agatccagga agagtcactg aggacctacc tcttcaccta cagcagtgtc   2460
tatgactcca tcagcatgga gacgctgtca gacatgtttg agctggatct gcccactgtg   2520
cactccatca tcagcaaaat gatcattaat gaggagctga tggcctccct ggaccagcca   2580
acacagacag tggtgatgca ccgcactgag cccactgccc agcagaacct ggctctgcag   2640
ctggccgaga agctgggcag cctggtggag aacaacgaac gggtgtttga ccacaagcag   2700
ggcacctacg ggggctactt ccgagaccag aaggacggca ccgcaaaaaa cgagggctac   2760
atgcgccgcg gtggctaccg ccagcagcag tctcagacgg cctactgagc tctccactct   2820
```

```
gtttcccgcc tgggccatcc aaccttgaag tcctaaacca cacctcagtc actaaaggtc    2880
tgtttaaagt tgttctggtt gattgcttgt tgccacaaag gtgtgttgag cccattcatt    2940
tgctgattat atttctgagc tgctaccaca tgacagacac aaggctcaga tgaagaggtg    3000
aattaaacac gttcctgacc tcaaaaaaaa aaaaaaaaa a                          3041

<210> SEQ ID NO 5
<211> LENGTH: 1507
<212> TYPE: DNA
<213> ORGANISM: Homo sapiens
<300> PUBLICATION INFORMATION:
<308> DATABASE ACCESSION NUMBER: GenBank/BC000533
<309> DATABASE ENTRY DATE: 2001-07-12
<313> RELEVANT RESIDUES: (1)..(1507)

<400> SEQUENCE: 5
ggcacgaggg ggccctgcgg tgtgactcgc gggctcagct ggtccggccg tagcacctcc      60
gcgccgtcgc catgtcgcgg tttttcacca ccggttcgga cagcgagtcc gagtcgtcct     120
tgtccgggga ggagctcgtc accaaacctg tcggaggcaa ctatggcaaa cagccattgt     180
tgctgagcga ggatgaagaa gataccaaga gagttgtccg cagtgccaag gacaagaggt     240
ttgaggagct gaccaacctt atccggacca tccgtaatgc catgaagatt cgtgatgtca     300
ccaagtgcct ggaagagttt gagctcctgg gaaaagcaca tgtgccatcc tctgccacat     360
ctaccaccat gctctgcact cgcgctggta ccaggcccgc gacctcatgc tcatgagcca     420
cttgcaggac aacattcagc atgcagaccc gccagtgcag atcctttaca accgcaccat     480
ggtgcagctg gcatctgtg ccttccgcca aggcctgacc aaggacgcac acaacgccct     540
gctggacatc cagtcgagtg gccgagccaa ggagcttctg ggccagggcc tgctgctgcg     600
cagcctgcag gagcgcaacc aggagcagga aaggtggag cggcgccgtc aggtcccctt     660
ccacctgcac atcaacctgg agctgctgga gtgtgtctac ctggtgtctg ccatgctcct     720
ggagatcccc tacatggccg cccatgagag cgatgcccgc cgacgcatga tcagcaagca     780
gttccaccac cagctgcgcg tgggcagcg acagcccctg ctgggtcccc ctgagtccat     840
gcgggaacat gtggtcgctg cctccaaggc catgaagatg ggtgactgga gacctgtca     900 cagttttatc atcaatgaga agatgaatgg gaaagtgtgg gaccttttcc ccgaggctga     960
caaagtccgc accatgctgg ttaggaagat ccaggaagag tcactgagga cctacctctt    1020
cacctacagc agtgtctatg actccatcag catggagacg ctgtcagaca tgtttgagct    1080
ggatctgccc actgtgcact ccatcatcag caaaatgatc attaatgagg agctgatggc    1140
ctccctggac cagccaacac agacagtggt gatgcaccgc actgagccca ctgcccagca    1200
gaacctggct ctgcagctgg ccgagaagct gggcagcctg gtggagaaca acgaacgggt    1260
gtttgaccac aagcagggca cctacggggg ctacttccga gaccagaagg acggctaccg    1320
caaaaacgag ggctacatgc gccgcggtgg ctaccgccag cagcagtctc agacggccta    1380
ctgagctctc cactctgttt cccgcctggg ccatccaacc ttgaagtcct aaaccacacc    1440
tcagtcacta aaggtctgtt taaagttaaa aaaaaaaaaa aaaaaaaaaa aaaaaaaaaa    1500
aaaaaaa                                                              1507

<210> SEQ ID NO 6
<211> LENGTH: 924
<212> TYPE: PRT
<213> ORGANISM: Homo sapiens
```

<400> SEQUENCE: 6

```
Arg Glu Glu Ser Gly Ala Gly Ala Arg Pro Arg Arg Ser Ala Asp
 1               5                  10                  15

Ser Gly Ala Ala Gly Ala Gly Arg Gly Gly Gly Glu Ala Ala Gly
            20                  25                  30

Lys Glu Glu Glu Gly Glu Ser Arg Ser Arg Arg Ala Ser Met Gly Arg
        35                  40                  45

Leu Ala Ser Arg Pro Leu Leu Leu Ala Leu Leu Ser Leu Ala Leu Cys
    50                  55                  60

Arg Gly Arg Val Val Arg Val Pro Thr Ala Thr Leu Val Arg Val Val
 65                  70                  75                  80

Gly Thr Glu Leu Val Ile Pro Cys Asn Val Ser Asp Tyr Asp Gly Pro
                85                  90                  95

Ser Glu Gln Asn Phe Asp Trp Ser Phe Ser Ser Leu Gly Ser Ser Phe
                100                 105                 110

Val Glu Leu Ala Ser Thr Trp Glu Val Gly Phe Pro Ala Gln Leu Tyr
            115                 120                 125

Gln Glu Arg Leu Gln Arg Gly Glu Ile Leu Leu Arg Arg Thr Ala Asn
130                 135                 140

Asp Ala Val Glu Leu His Ile Lys Asn Val Gln Pro Ser Asp Gln Gly
145                 150                 155                 160

His Tyr Lys Cys Ser Thr Pro Ser Thr Asp Ala Thr Val Gln Gly Asn
                165                 170                 175

Tyr Glu Asp Thr Val Gln Val Lys Val Leu Ala Asp Ser Leu His Val
            180                 185                 190

Gly Pro Ser Ala Arg Pro Pro Pro Ser Leu Ser Leu Arg Glu Gly Glu
        195                 200                 205

Pro Phe Glu Leu Arg Cys Thr Ala Ala Ser Ala Ser Pro Leu His Thr
    210                 215                 220

His Leu Ala Leu Leu Trp Glu Val His Arg Gly Pro Ala Arg Arg Ser
225                 230                 235                 240

Val Leu Ala Leu Thr His Glu Gly Arg Phe His Pro Gly Leu Gly Tyr
                245                 250                 255

Glu Gln Arg Tyr His Ser Gly Asp Val Arg Leu Asp Thr Val Gly Ser
            260                 265                 270

Asp Ala Tyr Arg Leu Ser Val Ser Arg Ala Leu Ser Ala Asp Gln Gly
        275                 280                 285

Ser Tyr Arg Cys Ile Val Ser Glu Trp Ile Ala Glu Gln Gly Asn Trp
    290                 295                 300

Gln Glu Ile Gln Glu Lys Ala Val Glu Val Ala Thr Val Val Ile Gln
305                 310                 315                 320

Pro Ser Val Leu Arg Ala Ala Val Pro Lys Asn Val Ser Val Ala Glu
                325                 330                 335

Gly Lys Glu Leu Asp Leu Thr Cys Asn Ile Thr Thr Asp Arg Ala Asp
            340                 345                 350

Asp Val Arg Pro Glu Val Thr Trp Ser Phe Ser Arg Met Pro Asp Ser
        355                 360                 365

Thr Leu Pro Gly Ser Arg Val Leu Ala Arg Leu Asp Arg Asp Ser Leu
    370                 375                 380

Val His Ser Ser Pro His Val Ala Leu Ser His Val Asp Ala Arg Ser
385                 390                 395                 400

Tyr His Leu Leu Val Arg Asp Val Ser Lys Glu Asn Ser Gly Tyr Tyr
                405                 410                 415
```

```
Tyr Cys His Val Ser Leu Trp Ala Pro Gly His Asn Arg Ser Trp His
            420                 425                 430

Lys Val Ala Glu Ala Val Ser Ser Pro Ala Gly Val Gly Val Thr Trp
            435                 440                 445

Leu Glu Pro Asp Tyr Gln Val Tyr Leu Asn Ala Ser Lys Val Pro Gly
            450                 455                 460

Phe Ala Asp Asp Pro Thr Glu Leu Ala Cys Arg Val Val Asp Thr Lys
465                 470                 475                 480

Ser Gly Glu Ala Asn Val Arg Phe Thr Val Ser Trp Tyr Tyr Arg Met
                485                 490                 495

Asn Arg Arg Ser Asp Asn Val Val Thr Ser Glu Leu Leu Ala Val Met
            500                 505                 510

Asp Gly Asp Trp Thr Leu Lys Tyr Gly Glu Arg Ser Lys Gln Arg Ala
            515                 520                 525

Gln Asp Gly Asp Phe Ile Phe Ser Lys Glu His Thr Asp Thr Phe Asn
530                 535                 540

Phe Arg Ile Gln Arg Thr Thr Glu Glu Asp Arg Gly Asn Tyr Tyr Cys
545                 550                 555                 560

Val Val Ser Ala Trp Thr Lys Gln Arg Asn Asn Ser Trp Val Lys Ser
                565                 570                 575

Lys Asp Val Phe Ser Lys Pro Val Asn Ile Phe Trp Ala Leu Glu Asp
            580                 585                 590

Ser Val Leu Val Val Lys Ala Arg Gln Pro Lys Pro Phe Phe Ala Ala
            595                 600                 605

Gly Asn Thr Phe Glu Met Thr Cys Lys Val Ser Ser Lys Asn Ile Lys
            610                 615                 620

Ser Pro Arg Tyr Ser Val Leu Ile Met Ala Glu Lys Pro Val Gly Asp
625                 630                 635                 640

Leu Ser Ser Pro Asn Glu Thr Lys Tyr Ile Ile Ser Leu Asp Gln Asp
                645                 650                 655

Ser Val Val Lys Leu Glu Asn Trp Thr Asp Ala Ser Arg Val Asp Gly
            660                 665                 670

Val Val Leu Glu Lys Val Gln Glu Asp Glu Phe Arg Tyr Arg Met Tyr
            675                 680                 685

Gln Thr Gln Val Ser Asp Ala Gly Leu Tyr Arg Cys Met Val Thr Ala
            690                 695                 700

Trp Ser Pro Val Arg Gly Ser Leu Trp Arg Glu Ala Ala Thr Ser Leu
705                 710                 715                 720

Ser Asn Pro Ile Glu Ile Asp Phe Gln Thr Ser Gly Pro Ile Phe Asn
                725                 730                 735

Ala Ser Val His Ser Asp Thr Pro Ser Val Ile Arg Gly Asp Leu Ile
            740                 745                 750

Lys Leu Phe Cys Ile Ile Thr Val Glu Gly Ala Ala Leu Asp Pro Asp
            755                 760                 765

Asp Met Ala Phe Asp Val Ser Trp Phe Ala Val His Ser Phe Gly Leu
            770                 775                 780

Asp Lys Ala Pro Val Leu Leu Ser Ser Leu Asp Arg Lys Gly Ile Val
785                 790                 795                 800

Thr Thr Ser Arg Arg Asp Trp Lys Ser Asp Leu Ser Leu Glu Arg Val
                805                 810                 815

Ser Val Leu Glu Phe Leu Leu Gln Val His Gly Ser Glu Asp Gln Asp
            820                 825                 830
```

```
Phe Gly Asn Tyr Tyr Cys Ser Val Thr Pro Trp Val Lys Ser Pro Thr
            835                 840                 845

Gly Ser Trp Gln Lys Glu Ala Glu Ile His Ser Lys Pro Val Phe Ile
    850                 855                 860

Thr Val Lys Met Asp Val Leu Asn Ala Phe Lys Tyr Pro Leu Leu Ile
865                 870                 875                 880

Gly Val Gly Leu Ser Thr Val Ile Gly Leu Leu Ser Cys Leu Ile Gly
                885                 890                 895

Tyr Cys Ser Ser His Trp Cys Cys Lys Lys Glu Val Gln Glu Thr Arg
                900                 905                 910

Arg Glu Arg Arg Arg Leu Met Ser Met Glu Met Asp
                915                 920

<210> SEQ ID NO 7
<211> LENGTH: 234
<212> TYPE: PRT
<213> ORGANISM: Homo sapiens

<400> SEQUENCE: 7

Met Leu Arg Val Pro Glu Pro Arg Pro Gly Glu Ala Lys Ala Glu Gly
1               5                   10                  15

Ala Ala Pro Pro Thr Pro Ser Lys Pro Leu Thr Ser Phe Leu Ile Gln
                20                  25                  30

Asp Ile Leu Arg Asp Gly Ala Gln Arg Gln Gly Gly Arg Thr Ser Ser
            35                  40                  45

Gln Arg Gln Arg Asp Pro Glu Pro Glu Pro Glu Pro Glu Pro Glu Gly
        50                  55                  60

Gly Arg Ser Arg Ala Gly Ala Gln Asn Asp Gln Leu Ser Thr Gly Pro
65                  70                  75                  80

Arg Ala Ala Pro Glu Glu Ala Glu Thr Leu Ala Glu Thr Glu Pro Glu
                85                  90                  95

Arg His Leu Gly Ser Tyr Leu Leu Asp Ser Glu Asn Thr Ser Gly Ala
                100                 105                 110

Leu Pro Arg Leu Pro Gln Thr Pro Lys Gln Pro Gln Lys Arg Ser Arg
            115                 120                 125

Ala Ala Phe Ser His Thr Gln Val Ile Glu Leu Glu Arg Lys Phe Ser
        130                 135                 140

His Gln Lys Tyr Leu Ser Ala Pro Glu Arg Ala His Leu Ala Lys Asn
145                 150                 155                 160

Leu Lys Leu Thr Glu Thr Gln Val Lys Ile Trp Phe Gln Asn Arg Arg
                165                 170                 175

Tyr Lys Thr Lys Arg Lys Gln Leu Ser Ser Glu Leu Gly Asp Leu Glu
                180                 185                 190

Lys His Ser Ser Leu Pro Ala Leu Lys Glu Glu Ala Phe Ser Arg Ala
            195                 200                 205

Ser Leu Val Ser Val Tyr Asn Ser Tyr Pro Tyr Pro Tyr Leu Tyr
        210                 215                 220

Cys Val Gly Ser Trp Ser Pro Ala Phe Trp
225                 230

<210> SEQ ID NO 8
<211> LENGTH: 2000
<212> TYPE: PRT
<213> ORGANISM: Homo sapiens

<400> SEQUENCE: 8
```

-continued

```
Met Lys Ala Ala Asp Thr Val Ile Leu Trp Ala Arg Ser Lys Asn Asp
1               5                   10                  15

Gln Leu Arg Ile Ser Phe Pro Pro Gly Leu Cys Trp Gly Asp Arg Met
            20                  25                  30

Pro Asp Lys Asp Asp Ile Arg Leu Leu Pro Ser Ala Leu Gly Val Lys
        35                  40                  45

Lys Arg Lys Arg Gly Pro Lys Lys Gln Lys Glu Asn Lys Pro Gly Lys
    50                  55                  60

Pro Arg Lys Arg Lys Lys Arg Asp Ser Glu Glu Phe Gly Ser Glu
65                  70                  75                  80

Arg Asp Glu Tyr Arg Glu Lys Ser Glu Ser Gly Ser Glu Tyr Gly
                85                  90                  95

Thr Gly Pro Gly Arg Lys Arg Arg Lys His Arg Glu Lys Lys Glu
                100                 105                 110

Lys Lys Thr Lys Arg Arg Lys Lys Gly Glu Gly Asp Gly Gly Gln Lys
        115                 120                 125

Gln Val Glu Gln Lys Ser Ser Ala Thr Leu Leu Thr Trp Gly Leu
    130                 135                 140

Glu Asp Val Glu His Val Phe Ser Glu Glu Asp Tyr His Thr Leu Thr
145                 150                 155                 160

Asn Tyr Lys Ala Phe Ser Gln Phe Met Arg Pro Leu Ile Ala Lys Lys
                165                 170                 175

Asn Pro Lys Ile Pro Met Ser Lys Met Met Thr Ile Leu Gly Ala Lys
            180                 185                 190

Trp Arg Glu Phe Ser Ala Asn Asn Pro Phe Lys Gly Ser Ala Ala Ala
        195                 200                 205

Val Ala Ala Ala Ala Ala Ala Ala Ala Val Ala Glu Gln Val
    210                 215                 220

Ser Ala Ala Val Ser Ser Ala Thr Pro Ile Ala Pro Ser Gly Pro Pro
225                 230                 235                 240

Ala Leu Pro Pro Pro Ala Ala Asp Ile Gln Pro Pro Ile Arg
            245                 250                 255

Arg Ala Lys Thr Lys Glu Gly Lys Gly Pro Gly His Lys Arg Arg Ser
        260                 265                 270

Lys Ser Pro Arg Val Pro Asp Gly Arg Lys Lys Leu Arg Gly Lys Lys
    275                 280                 285

Met Ala Pro Leu Lys Ile Lys Leu Gly Leu Leu Gly Lys Arg Lys
    290                 295                 300

Lys Gly Gly Ser Tyr Val Phe Gln Ser Asp Glu Gly Pro Glu Pro Glu
305                 310                 315                 320

Ala Glu Glu Ser Asp Leu Asp Ser Gly Ser Val His Ser Ala Ser Gly
                325                 330                 335

Arg Pro Asp Gly Pro Val Arg Thr Lys Lys Leu Lys Arg Gly Arg Pro
            340                 345                 350

Gly Arg Lys Lys Lys Lys Val Leu Gly Cys Pro Ala Val Ala Gly Glu
        355                 360                 365

Glu Glu Val Asp Gly Tyr Glu Thr Asp His Gln Asp Tyr Cys Glu Val
    370                 375                 380

Cys Gln Gln Gly Gly Glu Ile Ile Leu Cys Asp Thr Cys Pro Arg Ala
385                 390                 395                 400

Tyr His Leu Val Cys Leu Asp Pro Glu Leu Asp Arg Ala Pro Glu Gly
                405                 410                 415

Lys Trp Ser Cys Pro His Cys Glu Lys Glu Gly Val Gln Trp Glu Ala
```

-continued

```
                420                 425                 430
Lys Glu Glu Glu Glu Tyr Glu Glu Gly Glu Glu Gly Glu
            435                 440                 445
Lys Glu Glu Glu Asp Asp His Met Glu Tyr Cys Arg Val Cys Lys Asp
            450                 455                 460
Gly Gly Glu Leu Leu Cys Cys Asp Ala Cys Ile Ser Ser Tyr His Ile
465                 470                 475                 480
His Cys Leu Asn Pro Pro Leu Pro Asp Ile Pro Asn Gly Glu Trp Leu
                    485                 490                 495
Cys Pro Arg Cys Thr Cys Pro Val Leu Lys Gly Arg Val Gln Lys Ile
            500                 505                 510
Leu His Trp Arg Trp Gly Glu Pro Pro Val Ala Val Pro Ala Pro Gln
            515                 520                 525
Gln Ala Asp Gly Asn Pro Asp Val Pro Pro Arg Pro Leu Gln Gly
    530                 535                 540
Arg Ser Glu Arg Glu Phe Phe Val Lys Trp Val Gly Leu Ser Tyr Trp
545                 550                 555                 560
His Cys Ser Trp Ala Lys Glu Leu Gln Leu Glu Ile Phe His Leu Val
                565                 570                 575
Met Tyr Arg Asn Tyr Gln Arg Lys Asn Asp Met Asp Glu Pro Pro Pro
            580                 585                 590
Leu Asp Tyr Gly Ser Gly Glu Asp Asp Gly Lys Ser Asp Lys Arg Lys
            595                 600                 605
Val Lys Asp Pro His Tyr Ala Glu Met Glu Glu Lys Tyr Tyr Arg Phe
            610                 615                 620
Gly Ile Lys Pro Glu Trp Met Thr Val His Arg Ile Ile Asn His Ser
625                 630                 635                 640
Val Asp Lys Lys Gly Asn Tyr His Tyr Leu Val Lys Trp Arg Asp Leu
                645                 650                 655
Pro Tyr Asp Gln Ser Thr Trp Glu Glu Asp Glu Met Asn Ile Pro Glu
            660                 665                 670
Tyr Glu Glu His Lys Gln Ser Tyr Trp Arg His Arg Glu Leu Ile Met
            675                 680                 685
Gly Glu Asp Pro Ala Gln Pro Arg Lys Tyr Lys Lys Lys Lys Glu
    690                 695                 700
Leu Gln Gly Asp Gly Pro Pro Ser Ser Pro Thr Asn Asp Pro Thr Val
705                 710                 715                 720
Lys Tyr Glu Thr Gln Pro Arg Phe Ile Thr Ala Thr Gly Gly Thr Leu
                725                 730                 735
His Met Tyr Gln Leu Glu Gly Leu Asn Trp Leu Arg Phe Ser Trp Ala
            740                 745                 750
Gln Gly Thr Asp Thr Ile Leu Ala Asp Glu Met Gly Leu Gly Lys Thr
            755                 760                 765
Ile Gln Thr Ile Val Phe Leu Tyr Ser Leu Tyr Lys Glu Gly His Thr
    770                 775                 780
Lys Gly Pro Phe Leu Val Ser Ala Pro Leu Ser Thr Ile Ile Asn Trp
785                 790                 795                 800
Glu Arg Glu Phe Gln Met Trp Ala Pro Lys Phe Tyr Val Val Thr Tyr
                805                 810                 815
Thr Gly Asp Lys Asp Ser Arg Ala Ile Ile Arg Glu Asn Glu Phe Ser
            820                 825                 830
Phe Glu Asp Asn Ala Ile Lys Gly Gly Lys Lys Ala Phe Lys Met Lys
            835                 840                 845
```

-continued

```
Arg Glu Ala Gln Val Lys Phe His Val Leu Leu Thr Ser Tyr Glu Leu
    850                 855                 860

Ile Thr Ile Asp Gln Ala Ala Leu Gly Ser Ile Arg Trp Ala Cys Leu
865                 870                 875                 880

Val Val Asp Glu Ala His Arg Leu Lys Asn Asn Gln Ser Lys Phe Phe
                    885                 890                 895

Arg Val Leu Asn Gly Tyr Lys Ile Asp His Lys Leu Leu Leu Thr Gly
                900                 905                 910

Thr Pro Leu Gln Asn Asn Leu Glu Glu Leu Phe His Leu Leu Asn Phe
            915                 920                 925

Leu Thr Pro Glu Arg Phe Asn Asn Leu Glu Gly Phe Leu Glu Glu Phe
930                 935                 940

Ala Asp Ile Ser Lys Glu Asp Gln Ile Lys Lys Leu His Asp Leu Leu
945                 950                 955                 960

Gly Pro His Met Leu Arg Arg Leu Lys Ala Asp Val Phe Lys Asn Met
                965                 970                 975

Pro Ala Lys Thr Glu Leu Ile Val Arg Val Glu Leu Ser Pro Met Gln
                980                 985                 990

Lys Lys Tyr Tyr Lys Tyr Ile Leu Thr Arg Asn Phe Glu Ala Leu Asn
            995                 1000                1005

Ser Arg Gly Gly Gly Asn Gln Val Ser Leu Leu Asn Ile Met Met
    1010                1015                1020

Asp Leu Lys Lys Cys Cys Asn His Pro Tyr Leu Phe Pro Val Ala
    1025                1030                1035

Ala Met Glu Ser Pro Lys Leu Pro Ser Gly Ala Tyr Glu Gly Gly
    1040                1045                1050

Ala Leu Ile Lys Ser Ser Gly Lys Leu Met Leu Leu Gln Lys Met
    1055                1060                1065

Leu Arg Lys Leu Lys Glu Gln Gly His Arg Val Leu Ile Phe Ser
    1070                1075                1080

Gln Met Thr Lys Met Leu Asp Leu Leu Glu Asp Phe Leu Asp Tyr
    1085                1090                1095

Glu Gly Tyr Lys Tyr Glu Arg Ile Asp Gly Gly Ile Thr Gly Ala
    1100                1105                1110

Leu Arg Gln Glu Ala Ile Asp Arg Phe Asn Ala Pro Gly Ala Gln
    1115                1120                1125

Gln Phe Cys Phe Leu Leu Ser Thr Arg Ala Gly Gly Leu Gly Ile
    1130                1135                1140

Asn Leu Ala Thr Ala Asp Thr Val Ile Ile Phe Asp Ser Asp Trp
    1145                1150                1155

Asn Pro His Asn Asp Ile Gln Ala Phe Ser Arg Ala His Arg Ile
    1160                1165                1170

Gly Gln Ala Asn Lys Val Met Ile Tyr Arg Phe Val Thr Arg Ala
    1175                1180                1185

Ser Val Glu Glu Arg Ile Thr Gln Val Ala Lys Arg Lys Met Met
    1190                1195                1200

Leu Thr His Leu Val Val Arg Pro Gly Leu Gly Ser Lys Ala Gly
    1205                1210                1215

Ser Met Ser Lys Gln Glu Leu Asp Asp Ile Leu Lys Phe Gly Thr
    1220                1225                1230

Glu Glu Leu Phe Lys Asp Glu Asn Glu Gly Glu Asn Lys Glu Glu
    1235                1240                1245
```

-continued

```
Asp Ser Ser Val Ile His Tyr Asp Asn Glu Ala Ile Ala Arg Leu
    1250                1255                1260

Leu Asp Arg Asn Gln Asp Ala Thr Glu Asp Thr Asp Val Gln Asn
    1265                1270                1275

Met Asn Glu Tyr Leu Ser Ser Phe Lys Val Ala Gln Tyr Val Val
    1280                1285                1290

Arg Glu Glu Asp Lys Ile Glu Glu Ile Glu Arg Glu Ile Ile Lys
    1295                1300                1305

Gln Glu Glu Asn Val Asp Pro Asp Tyr Trp Glu Lys Leu Leu Arg
    1310                1315                1320

His His Tyr Glu Gln Gln Gln Glu Asp Leu Ala Arg Asn Leu Gly
    1325                1330                1335

Lys Gly Lys Arg Val Arg Lys Gln Val Asn Tyr Asn Asp Ala Ala
    1340                1345                1350

Gln Glu Asp Gln Asp Asn Gln Ser Glu Tyr Ser Val Gly Ser Glu
    1355                1360                1365

Glu Glu Asp Glu Asp Phe Asp Glu Arg Pro Glu Gly Arg Arg Gln
    1370                1375                1380

Ser Lys Arg Gln Leu Arg Asn Glu Lys Asp Lys Pro Leu Pro Pro
    1385                1390                1395

Leu Leu Ala Arg Val Gly Gly Asn Ile Glu Val Leu Gly Phe Asn
    1400                1405                1410

Thr Arg Gln Arg Lys Ala Phe Leu Asn Ala Val Met Arg Trp Gly
    1415                1420                1425

Met Pro Pro Gln Asp Ala Phe Thr Thr Gln Trp Leu Val Arg Asp
    1430                1435                1440

Leu Arg Gly Lys Thr Glu Lys Glu Phe Lys Ala Tyr Val Ser Leu
    1445                1450                1455

Phe Met Arg His Leu Cys Glu Pro Gly Ala Asp Gly Ser Glu Thr
    1460                1465                1470

Phe Ala Asp Gly Val Pro Arg Glu Gly Leu Ser Arg Gln Gln Val
    1475                1480                1485

Leu Thr Arg Ile Gly Val Met Ser Leu Val Lys Lys Lys Val Gln
    1490                1495                1500

Glu Phe Glu His Ile Asn Gly Arg Trp Ser Met Pro Glu Leu Met
    1505                1510                1515

Pro Asp Pro Ser Ala Asp Ser Lys Arg Ser Ser Arg Ala Ser Ser
    1520                1525                1530

Pro Thr Lys Thr Ser Pro Thr Thr Pro Glu Ala Ser Ala Thr Asn
    1535                1540                1545

Ser Pro Cys Thr Ser Lys Pro Ala Thr Pro Ala Pro Ser Glu Lys
    1550                1555                1560

Gly Glu Gly Ile Arg Thr Pro Leu Glu Lys Glu Ala Glu Asn
    1565                1570                1575

Gln Glu Glu Lys Pro Glu Lys Asn Ser Arg Ile Gly Glu Lys Met
    1580                1585                1590

Glu Thr Glu Ala Asp Ala Pro Ser Pro Ala Pro Ser Leu Gly Glu
    1595                1600                1605

Arg Leu Glu Pro Arg Lys Ile Pro Leu Glu Asp Glu Val Pro Gly
    1610                1615                1620

Val Pro Gly Glu Met Glu Pro Glu Pro Gly Tyr Arg Gly Asp Arg
    1625                1630                1635

Glu Lys Ser Ala Thr Glu Ser Thr Pro Gly Glu Arg Gly Glu Glu
```

-continued

```
             1640                1645                1650
Lys Pro Leu Asp Gly Gln Glu His Arg Glu Arg Pro Glu Gly Glu
     1655                1660                1665

Thr Gly Asp Leu Gly Lys Arg Glu Asp Val Lys Gly Asp Arg Glu
     1670                1675                1680

Leu Arg Pro Gly Pro Arg Asp Glu Pro Arg Ser Asn Gly Arg Arg
     1685                1690                1695

Glu Glu Lys Thr Glu Asn Pro Arg Phe Met Phe Asn Ile Ala Asp
     1700                1705                1710

Gly Gly Phe Thr Glu Leu His Thr Leu Trp Gln Asn Glu Glu Arg
     1715                1720                1725

Ala Ala Ile Ser Ser Gly Lys Leu Asn Glu Ile Trp His Arg Arg
     1730                1735                1740

His Asp Tyr Trp Leu Leu Ala Gly Ile Val Leu His Gly Tyr Ala
     1745                1750                1755

Arg Trp Gln Asp Ile Gln Asn Asp Ala Gln Phe Ala Ile Ile Asn
     1760                1765                1770

Glu Pro Phe Lys Thr Glu Ala Asn Lys Gly Asn Phe Leu Glu Met
     1775                1780                1785

Lys Asn Lys Phe Leu Ala Arg Arg Phe Lys Leu Leu Glu Gln Ala
     1790                1795                1800

Leu Val Ile Glu Glu Gln Leu Arg Arg Ala Ala Tyr Leu Asn Leu
     1805                1810                1815

Ser Gln Glu Pro Ala His Pro Ala Met Ala Leu His Ala Arg Phe
     1820                1825                1830

Ala Glu Ala Glu Cys Leu Ala Glu Ser His Gln His Leu Ser Lys
     1835                1840                1845

Glu Ser Leu Ala Gly Asn Lys Pro Ala Asn Ala Val Leu His Lys
     1850                1855                1860

Val Leu Asn Gln Leu Glu Glu Leu Leu Ser Asp Met Lys Ala Asp
     1865                1870                1875

Val Thr Arg Leu Pro Ala Thr Leu Ser Arg Ile Pro Pro Ile Ala
     1880                1885                1890

Ala Arg Leu Gln Met Ser Glu Arg Ser Ile Leu Ser Arg Leu Ala
     1895                1900                1905

Ser Lys Gly Thr Glu Pro His Pro Thr Pro Ala Tyr Pro Pro Gly
     1910                1915                1920

Pro Tyr Ala Thr Pro Pro Gly Tyr Gly Ala Ala Phe Ser Ala Ala
     1925                1930                1935

Pro Val Gly Ala Leu Ala Ala Ala Gly Ala Asn Tyr Ser Gln Met
     1940                1945                1950

Pro Ala Gly Ser Phe Ile Thr Ala Ala Thr Asn Gly Pro Pro Val
     1955                1960                1965

Leu Val Lys Lys Glu Lys Glu Met Val Gly Ala Leu Val Ser Asp
     1970                1975                1980

Gly Leu Asp Arg Lys Glu Pro Arg Ala Gly Glu Val Ile Cys Ile
     1985                1990                1995

Asp Asp
     2000

<210> SEQ ID NO 9
<211> LENGTH: 913
<212> TYPE: PRT
<213> ORGANISM: Homo sapiens
```

<400> SEQUENCE: 9

```
Met Ser Arg Phe Phe Thr Thr Gly Ser Asp Ser Glu Ser Glu Ser Ser
1               5                   10                  15

Leu Ser Gly Glu Glu Leu Val Thr Lys Pro Val Gly Gly Asn Tyr Gly
            20                  25                  30

Lys Gln Pro Leu Leu Leu Ser Glu Asp Glu Glu Asp Thr Lys Arg Val
        35                  40                  45

Val Arg Ser Ala Lys Asp Lys Arg Phe Glu Glu Leu Thr Asn Leu Ile
    50                  55                  60

Arg Thr Ile Arg Asn Ala Met Lys Ile Arg Asp Val Thr Lys Cys Leu
65                  70                  75                  80

Glu Glu Phe Glu Leu Leu Gly Lys Ala Tyr Gly Lys Ala Lys Ser Ile
                85                  90                  95

Val Asp Lys Glu Gly Val Pro Arg Phe Tyr Ile Arg Ile Leu Ala Asp
            100                 105                 110

Leu Glu Asp Tyr Leu Asn Glu Leu Trp Glu Asp Lys Glu Gly Lys Lys
        115                 120                 125

Lys Met Asn Lys Asn Asn Ala Lys Ala Leu Ser Thr Leu Arg Gln Lys
    130                 135                 140

Ile Arg Lys Tyr Asn Arg Asp Phe Glu Ser His Ile Thr Ser Tyr Lys
145                 150                 155                 160

Gln Asn Pro Glu Gln Ser Ala Asp Glu Asp Ala Glu Lys Asn Glu Glu
                165                 170                 175

Asp Ser Glu Gly Ser Ser Asp Glu Asp Glu Asp Glu Asp Gly Val Ser
            180                 185                 190

Ala Ala Thr Phe Leu Lys Lys Ser Glu Ala Pro Ser Gly Glu Ser
        195                 200                 205

Arg Lys Phe Leu Lys Lys Met Asp Asp Glu Asp Glu Asp Ser Glu Asp
    210                 215                 220

Ser Glu Asp Asp Glu Asp Trp Asp Thr Gly Ser Thr Ser Ser Asp Ser
225                 230                 235                 240

Asp Ser Glu Glu Glu Glu Gly Lys Gln Thr Ala Leu Ala Ser Arg Phe
                245                 250                 255

Leu Lys Lys Ala Pro Thr Thr Asp Glu Asp Lys Lys Ala Ala Glu Lys
            260                 265                 270

Lys Arg Glu Asp Lys Ala Lys Lys Lys His Asp Arg Lys Ser Lys Arg
    275                 280                 285

Leu Asp Glu Glu Glu Glu Asp Asn Glu Gly Gly Glu Trp Glu Arg Val
    290                 295                 300

Arg Gly Gly Val Pro Leu Val Lys Glu Lys Pro Lys Met Phe Ala Lys
305                 310                 315                 320

Gly Thr Glu Ile Thr His Ala Val Val Ile Lys Lys Leu Asn Glu Ile
                325                 330                 335

Leu Gln Ala Arg Gly Lys Lys Gly Thr Asp Arg Ala Ala Gln Ile Glu
            340                 345                 350

Leu Leu Gln Leu Leu Val Gln Ile Ala Ala Glu Asn Asn Leu Gly Glu
        355                 360                 365

Gly Val Ile Val Lys Ile Lys Phe Asn Ile Ala Ser Leu Tyr Asp
    370                 375                 380

Tyr Asn Pro Asn Leu Ala Thr Tyr Met Lys Pro Glu Met Trp Gly Lys
385                 390                 395                 400

Cys Leu Asp Cys Ile Asn Glu Leu Met Asp Ile Leu Phe Ala Asn Pro
```

-continued

```
            405                 410                 415
Asn Ile Phe Val Gly Glu Asn Ile Leu Glu Glu Ser Glu Asn Leu His
                420                 425                 430
Asn Ala Asp Gln Pro Leu Arg Val Arg Gly Cys Ile Leu Thr Leu Val
                435                 440                 445
Glu Arg Met Asp Glu Glu Phe Thr Lys Ile Met Gln Asn Thr Asp Pro
    450                 455                 460
His Ser Gln Glu Tyr Val Glu His Leu Lys Asp Glu Ala Gln Val Cys
465                 470                 475                 480
Ala Ile Ile Glu Arg Val Gln Arg Tyr Leu Glu Glu Lys Gly Thr Thr
                485                 490                 495
Glu Glu Val Cys Arg Ile Tyr Leu Leu Arg Ile Leu His Thr Tyr Tyr
                500                 505                 510
Lys Phe Asp Tyr Lys Ala His Gln Arg Gln Leu Thr Pro Pro Glu Gly
            515                 520                 525
Ser Ser Lys Ser Glu Gln Asp Gln Ala Glu Asn Glu Gly Glu Asp Ser
            530                 535                 540
Ala Val Leu Met Glu Arg Leu Cys Lys Tyr Ile Tyr Ala Lys Asp Arg
545                 550                 555                 560
Thr Asp Arg Ile Arg Thr Cys Ala Ile Leu Cys His Ile Tyr His His
                565                 570                 575
Ala Leu His Ser Arg Trp Tyr Gln Ala Arg Asp Leu Met Leu Met Ser
                580                 585                 590
His Leu Gln Asp Asn Ile Gln His Ala Asp Pro Val Gln Ile Leu
                595                 600                 605
Tyr Asn Arg Thr Met Val Gln Leu Gly Ile Cys Ala Phe Arg Gln Gly
    610                 615                 620
Leu Thr Lys Asp Ala His Asn Ala Leu Leu Asp Ile Gln Ser Ser Gly
625                 630                 635                 640
Arg Ala Lys Glu Leu Leu Gly Gln Gly Leu Leu Arg Ser Leu Gln
                645                 650                 655
Glu Arg Asn Gln Glu Gln Glu Lys Val Glu Arg Arg Gln Val Pro
    660                 665                 670
Phe His Leu His Ile Asn Leu Glu Leu Leu Glu Cys Val Tyr Leu Val
                675                 680                 685
Ser Ala Met Leu Leu Glu Ile Pro Tyr Met Ala Ala His Glu Ser Asp
            690                 695                 700
Ala Arg Arg Arg Met Ile Ser Lys Gln Phe His His Gln Leu Arg Val
705                 710                 715                 720
Gly Glu Arg Gln Pro Leu Leu Gly Pro Pro Glu Ser Met Arg Glu His
                725                 730                 735
Val Val Ala Ala Ser Lys Ala Met Lys Met Gly Asp Trp Lys Thr Cys
                740                 745                 750
His Ser Phe Ile Ile Asn Glu Lys Met Asn Gly Lys Val Trp Asp Leu
            755                 760                 765
Phe Pro Glu Ala Asp Lys Val Arg Thr Met Leu Val Arg Lys Ile Gln
    770                 775                 780
Glu Glu Ser Leu Arg Thr Tyr Leu Phe Thr Tyr Ser Ser Val Tyr Asp
785                 790                 795                 800
Ser Ile Ser Met Glu Thr Leu Ser Asp Met Phe Glu Leu Asp Leu Pro
            805                 810                 815
Thr Val His Ser Ile Ile Ser Lys Met Ile Ile Asn Glu Glu Leu Met
            820                 825                 830
```

Ala Ser Leu Asp Gln Pro Thr Gln Thr Val Met His Arg Thr Glu
            835                 840                 845

Pro Thr Ala Gln Gln Asn Leu Ala Leu Gln Leu Ala Glu Lys Leu Gly
    850                 855                 860

Ser Leu Val Glu Asn Asn Glu Arg Val Phe Asp His Lys Gln Gly Thr
865                 870                 875                 880

Tyr Gly Gly Tyr Phe Arg Asp Gln Lys Asp Gly Tyr Arg Lys Asn Glu
                885                 890                 895

Gly Tyr Met Arg Arg Gly Gly Tyr Arg Gln Gln Gln Ser Gln Thr Ala
            900                 905                 910

Tyr

<210> SEQ ID NO 10
<211> LENGTH: 325
<212> TYPE: PRT
<213> ORGANISM: Homo sapiens

<400> SEQUENCE: 10

Met Leu Met Ser His Leu Gln Asp Asn Ile Gln His Ala Asp Pro Pro
1               5                   10                  15

Val Gln Ile Leu Tyr Asn Arg Thr Met Val Gln Leu Gly Ile Cys Ala
                20                  25                  30

Phe Arg Gln Gly Leu Thr Lys Asp Ala His Asn Ala Leu Leu Asp Ile
            35                  40                  45

Gln Ser Ser Gly Arg Ala Lys Glu Leu Leu Gly Gln Gly Leu Leu Leu
    50                  55                  60

Arg Ser Leu Gln Glu Arg Asn Gln Glu Gln Glu Lys Val Glu Arg Arg
65                  70                  75                  80

Arg Gln Val Pro Phe His Leu His Ile Asn Leu Glu Leu Leu Glu Cys
                85                  90                  95

Val Tyr Leu Val Ser Ala Met Leu Leu Glu Ile Pro Tyr Met Ala Ala
            100                 105                 110

His Glu Ser Asp Ala Arg Arg Arg Met Ile Ser Lys Gln Phe His His
    115                 120                 125

Gln Leu Arg Val Gly Glu Arg Gln Pro Leu Leu Gly Pro Pro Glu Ser
    130                 135                 140

Met Arg Glu His Val Val Ala Ala Ser Lys Ala Met Lys Met Gly Asp
145                 150                 155                 160

Trp Lys Thr Cys His Ser Phe Ile Ile Asn Glu Lys Met Asn Gly Lys
                165                 170                 175

Val Trp Asp Leu Phe Pro Glu Ala Asp Lys Val Arg Thr Met Leu Val
            180                 185                 190

Arg Lys Ile Gln Glu Glu Ser Leu Arg Thr Tyr Leu Phe Thr Tyr Ser
    195                 200                 205

Ser Val Tyr Asp Ser Ile Ser Met Glu Thr Leu Ser Asp Met Phe Glu
    210                 215                 220

Leu Asp Leu Pro Thr Val His Ser Ile Ile Ser Lys Met Ile Ile Asn
225                 230                 235                 240

Glu Glu Leu Met Ala Ser Leu Asp Gln Pro Thr Gln Thr Val Val Met
                245                 250                 255

His Arg Thr Glu Pro Thr Ala Gln Gln Asn Leu Ala Leu Gln Leu Ala
            260                 265                 270

Glu Lys Leu Gly Ser Leu Val Glu Asn Asn Glu Arg Val Phe Asp His
    275                 280                 285

```
Lys Gln Gly Thr Tyr Gly Gly Tyr Phe Arg Asp Gln Lys Asp Gly Tyr
    290                 295                 300

Arg Lys Asn Glu Gly Tyr Met Arg Arg Gly Gly Tyr Arg Gln Gln Gln
305                 310                 315                 320

Ser Gln Thr Ala Tyr
                325

<210> SEQ ID NO 11
<211> LENGTH: 392
<212> TYPE: DNA
<213> ORGANISM: Homo sapiens

<400> SEQUENCE: 11
ttcccctttg gaagagagag cagtgttaga tccttcaaag tcaagataaa agcagaggat      60
tgcaattagg gcatgagtca ccagcgagcc tcagaaaacc ctactgggat gcttccgaaa     120
ggccagtgct gtgcagggggg cgagacactt cagggagcgg gaggctccaa ggacagagct    180
tttaaagcag cagcagaagc ctgggatgtg aagatctct gtctactctc ctattcctga     240
tgggagcagt cgggcaaagc acccgctct tgactctgct ctacaggcca ttcacataac     300
agcaaattgc tgggtttcct tcatgtccct attaggaaag caaaacatac cacaaagtat    360 acccttctc actaaccccc tgcagtggac ct                                    392

<210> SEQ ID NO 12
<211> LENGTH: 250
<212> TYPE: DNA
<213> ORGANISM: Homo sapiens

<400> SEQUENCE: 12
ttcagaggag gggagagaaa gagtactcag tagggactga gcactaaatg cttattttaa      60
aagaaatgta aagagcagaa agcaattcag gctaccctgc cttttgtgct ggctagcact     120
ccggtcggtg tcagcagcac gtggcattga acattgcaat gtggagccca aaccacagaa    180
aatggggtga aattggccaa ctttctatta acttatgttg gcaattttgc caccaacagt     240
aagctggccc                                                            250

<210> SEQ ID NO 13
<211> LENGTH: 359
<212> TYPE: DNA
<213> ORGANISM: Homo sapiens

<400> SEQUENCE: 13
tgcacgtcag tgtcctcagt tgcatcctgg ttccggtccg acagccgagc gatggcctca      60
ttgtcataat gaatcacact gctgtcctcc tccttgttct cccctcgtt ttcatccttg     120 aatagctctt cagtgccaaa tttgagaatg tcgtcaagct cctgcttgga catggagcct    180
gccttggagc ccagcccagg ccgcacaacc aggtgtgtca gcatcatctt tctcttggcc    240
acttgtgtga ttcgctcttc cactgacgcg cgagtcacaa accggtaaat catcactttg    300
ttggcctggc caatccgatg agcccggcta aaggcctgga tgtcattatg ggggttcca     359

<210> SEQ ID NO 14
<211> LENGTH: 167
<212> TYPE: DNA
<213> ORGANISM: Homo sapiens

<400> SEQUENCE: 14
caggcgggaa acagagtgga gagctcagta ggccgtctga gactgctgct ggcggtagcc      60
```

```
accgcggcgc atgtagccct cgttttgcg gtagccgtcc ttctggtctc ggaagtagcc    120
cccgtaggtg ccctgcttgt ggtcaaacac ccgttcgttg ttctcca               167

<210> SEQ ID NO 15
<211> LENGTH: 5852
<212> TYPE: DNA
<213> ORGANISM: Homo sapiens

<400> SEQUENCE: 15
tcaatattgg ccattagcca tattattcat tggttatata gcataaatca atattggcta    60
ttggccattg catacgttgt atctatatca taatatgtac atttatattg gctcatgtcc   120
aatatgaccg ccatgttggc attgattatt gactagttat taatagtaat caattacggg   180
gtcattagtt catagcccat atatggagtt ccgcgttaca taacttacgg taaatggccc   240
gcctggctga ccgcccaacg accccgcccc attgacgtca ataatgacgt atgttcccat   300
agtaacgcca atagggactt tccattgacg tcaatgggtg gagtatttac ggtaaactgc   360
ccacttggca gtacatcaag tgtatcatat gccaagtccg cccctattg acgtcaatga   420 cggtaaatgg cccgcctggc attatgccca gtacatgacc ttacgggact tcctacttg   480 gcagtacatc tacgtattag tcatcgctat taccatggtg atgcggtttt ggcagtacac   540
caatgggcgt ggatagcggt ttgactcacg gggatttcca agtctccacc ccattgacgt   600
caatgggagt ttgttttggc accaaaatca acgggacttt ccaaaatgtc gtaacaactg   660
cgatcgcccg cccgttgac gcaaatgggc ggtaggcgtg tacggtggga ggtctatata   720
agcagagctc gtttagtgaa ccgtcagatc actagaagct ttattgcggt agtttatcac   780
agttaaattg ctaacgcagt cagtgcttct gacacaacag tctcgaactt aagctgcagt   840
gactctctta aggtagcctt gcagaagttg gtcgtgaggc actgggcagg taagtatcaa   900
ggttacaaga caggtttaag gagaccaata gaaactgggc ttgtcgagac agagaagact   960
cttgcgtttc tgataggcac ctattggtct tactgacatc cactttgcct ttctctccac  1020
aggtgtccac tcccagttca attacagctc ttaaggctag agtacttaat acgactcact  1080
ataggctagc ctcgagaatt cacgcgtttc ccctttggaa gagagagcag tgttagatcc  1140
ttcaaagtca agataaaagc agaggattgc aattagggca tgagtcacca gcagcctca   1200 gaaaaccta ctgggatgct tccgaaaggc cagtgctgtg caggggggcga gacacttcag  1260 ggagcgggag gctccaagga cagagctttt aaagcagcag cagaagcctg ggatgtggaa  1320
gatctctgtc tactctccta ttcctgatgg gagcagtcgg gcaaagcaca ccgctcttga  1380
ctctgctcta caggccattc acataacagc aaattgctgg gtttccttca tgtccctatt  1440
aggaaagcaa acataccac aaagtatacc ctttctcact aaccccctgc agtggacctg  1500
tcgacccggg cggccgcttc cctttagtga gggttaatgc ttcgagcaga catgataaga  1560
tacattgatg agtttggaca accacaact agaatgcagt gaaaaaaatg ctttatttgt  1620
gaaatttgtg atgctattgc tttatttgta accattataa gctgcaataa acaagttaac  1680
aacaacaatt gcattcattt tatgtttcag gttcaggggg agatgtggga ggttttttaa  1740
agcaagtaaa acctctacaa atgtggtaaa atccgataag gatcgatccg gctggcgta   1800 atagcgaaga ggcccgcacc gatcgccctt cccaacagtt gcgcagcctg aatggcgaat  1860
ggacgcgccc tgtagcggcg cattaagcgc ggcgggtgtg gtggttacgc gcagcgtgac  1920
cgctacactt gccagcgccc tagcgcccgc tcctttcgct ttcttccctt cctttctcgc  1980
```

```
cacgttcgcc ggctttcccc gtcaagctct aaatcggggg ctcccttag ggttccgatt    2040 tagtgcttta cggcacctcg accccaaaaa acttgattag ggtgatggtt cacgtagtgg    2100
gccatcgccc tgatagacgg ttttcgccc tttgacgttg gagtccacgt tctttaatag    2160
tggactcttg ttccaaactg aacaacact caaccctatc tcggtctatt cttttgattt    2220
ataagggatt ttgccgattt cggcctattg gttaaaaaat gagctgattt aacaaaaatt    2280
taacgcgaat tttaacaaaa tattaacgct tacaatttcc tgatgcggta ttttctcctt    2340
acgcatctgt gcggtatttc acaccgcata cgcggatctg cgcagcacca tggcctgaaa    2400
taacctctga agaggaact tggttaggta ccttctgagg cggaaagaac cagctgtgga    2460
atgtgtgtca gttagggtgt ggaaagtccc caggctcccc agcaggcaga agtatgcaaa    2520
gcatgcatct caattagtca gcaaccaggt gtggaaagtc cccaggctcc ccagcaggca    2580
gaagtatgca aagcatgcat ctcaattagt cagcaaccat agtcccgccc ctaactccgc    2640
ccatcccgcc cctaactccg cccagttccg cccattctcc gccccatggc tgactaattt    2700
tttttattta tgcagaggcc gaggccgcct cggcctctga gctattccag aagtagtgag    2760
gaggcttttt tggaggccta ggcttttgca aaaagcttga ttcttctgac acaacagtct    2820
cgaacttaag gctagagcca ccatgattga acaagatgga ttgcacgcag gttctccggc    2880
cgcttgggtg gagaggctat tcggctatga ctgggcacaa cagacaatcg gctgctctga    2940
tgccgccgtg ttccggctgt cagcgcaggg gcgcccggtt cttttttgtca agaccgacct    3000 gtccggtgcc ctgaatgaac tgcaggacga ggcagcgcgg ctatcgtggc tggccacgac    3060
gggcgttcct tgcgcagctg tgctcgacgt tgtcactgaa gcgggaaggg actggctgct    3120
attgggcgaa gtgccgggc aggatctcct gtcatctcac cttgctcctg ccgagaaagt    3180
atccatcatg gctgatgcaa tgcggcggct gcatacgctt gatccggcta cctgcccatt    3240
cgaccaccaa gcgaaacatc gcatcgagcg agcacgtact cggatggaag ccggtcttgt    3300
cgatcaggat gatctggacg aagagcatca ggggctcgcg ccagccgaac tgttcgccag    3360
gctcaaggcg cgcatgcccg acggcgagga tctcgtcgtg acccatggcg atgcctgctt    3420
gccgaatatc atggtggaaa atggccgctt ttctggattc atcgactgtg gccggctggg    3480
tgtggcggac cgctatcagg acatagcgtt ggctacccgt gatattgctg aagagcttgg    3540
cggcgaatgg gctgaccgct tcctcgtgct ttacggtatc gccgctcccg attcgcagcg    3600
catcgccttc tatcgccttc ttgacgagtt cttctgagcg ggactctggg gttcgaaatg    3660
accgaccaag cgacgcccaa cctgccatca cgatggccgc aataaaatat ctttattttc    3720
attacatctg tgtgttggtt ttttgtgtga atcgatagcg ataaggatcc gcgtatggtg    3780
cactctcagt acaatctgct ctgatgccgc atagttaagc cagccccgac acccgccaac    3840
acccgctgac gcgccctgac gggcttgtct gctcccggca tccgcttaca gacaagctgt    3900
gaccgtctcc gggagctgca tgtgtcagag gttttcaccg tcatcaccga aacgcgcgag    3960
acgaaagggc ctcgtgatac gcctattttt ataggttaat gtcatgataa taatggtttc    4020
ttagacgtca ggtggcactt ttcggggaaa tgtgcgcgga accctattt gtttattttt    4080 ctaaatacat tcaaatatgt atccgctcat gagacaataa ccctgataaa tgcttcaata    4140
atattgaaaa aggaagagta tgagtattca acatttccgt gtcgccctta ttcccttttt    4200
tgcggcattt tgccttcctg tttttgctca cccagaaacg ctggtgaaag taaaagatgc    4260
tgaagatcag ttgggtgcac gagtgggtta catcgaactg gatctcaaca gcggtaagat    4320
ccttgagagt tttcgccccg aagaacgttt tccaatgatg agcacttta aagttctgct    4380
```

```
atgtggcgcg gtattatccc gtattgacgc cgggcaagag caactcggtc gccgcataca    4440
ctattctcag aatgacttgg ttgagtactc accagtcaca gaaaagcatc ttacggatgg    4500
catgacagta agagaattat gcagtgctgc cataaccatg agtgataaca ctgcggccaa    4560
cttacttctg acaacgatcg gaggaccgaa ggagctaacc gcttttttgc acaacatggg    4620
ggatcatgta actcgccttg atcgttggga accggagctg aatgaagcca taccaaacga    4680
cgagcgtgac accacgatgc ctgtagcaat ggcaacaacg ttgcgcaaac tattaactgg    4740
cgaactactt actctagctt cccggcaaca attaatagac tggatggagg cggataaagt    4800
tgcaggacca cttctgcgct cggcccttcc ggctggctgg tttattgctg ataaatctgg    4860
agccggtgag cgtgggtctc gcggtatcat tgcagcactg gggccagatg gtaagccctc    4920
ccgtatcgta gttatctaca cgacggggag tcaggcaact atggatgaac gaaatagaca    4980
gatcgctgag ataggtgcct cactgattaa gcattggtaa ctgtcagacc aagtttactc    5040
atatatactt tagattgatt taaaacttca tttttaattt aaaaggatct aggtgaagat    5100
cctttttgat aatctcatga ccaaaatccc ttaacgtgag ttttcgttcc actgagcgtc    5160
agaccccgta gaaaagatca aaggatcttc ttgagatcct ttttttctgc gcgtaatctg    5220
ctgcttgcaa acaaaaaaac caccgctacc agcggtggtt tgtttgccgg atcaagagct    5280
accaactctt tttccgaagg taactggctt cagcagagcg cagataccaa atactgttct    5340
tctagtgtag ccgtagttag gccaccactt caagaactct gtagcaccgc ctacatacct    5400
cgctctgcta atcctgttac cagtggctgc tgccagtggc gataagtcgt gtcttaccgg    5460
gttggactca agacgatagt taccggataa ggcgcagcgg tcgggctgaa cggggggttc    5520
gtgcacacag cccagcttgg agcgaacgac ctacaccgaa ctgagatacc tacagcgtga    5580
gctatgagaa agcgccacgc ttcccgaagg gagaaaggcg gacaggtatc cggtaagcgg    5640
cagggtcgga acaggagagc gcacgaggga gcttccaggg ggaaacgcct ggtatcttta    5700
tagtcctgtc gggtttcgcc acctctgact tgagcgtcga ttttgtgat gctcgtcagg    5760
ggggcggagc ctatgaaaa acgccagcaa cgcggccttt ttacggttcc tggccttttg    5820
ctggcctttt gctcacatgg ctcgacagat ct                                  5852
```

<210> SEQ ID NO 16
<211> LENGTH: 5710
<212> TYPE: DNA
<213> ORGANISM: Homo sapiens

<400> SEQUENCE: 16

```
tcaatattgg ccattagcca tattattcat tggttatata gcataaatca atattggcta      60
ttggccattg catacgttgt atctatatca taatatgtac atttatattg gctcatgtcc     120
aatatgaccg cctatgttgg cattgattat tgactagtta taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccctattg acgtcaatga     420
cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg gggatttcca agtctccacc ccattgacgt     600
```

```
caatgggagt ttgttttggc accaaaatca acgggacttt ccaaaatgtc gtaacaactg      660
cgatcgcccg ccccgttgac gcaaatgggc ggtaggcgtg tacggtggga ggtctatata      720
agcagagctc gtttagtgaa ccgtcagatc actagaagct ttattgcggt agtttatcac      780
agttaaattg ctaacgcagt cagtgcttct gacacaacag tctcgaactt aagctgcagt      840
gactctctta aggtagcctt gcagaagttg gtcgtgaggc actgggcagg taagtatcaa      900
ggttacaaga caggtttaag gagaccaata gaaactgggc ttgtcgagac agagaagact      960
cttgcgtttc tgataggcac ctattggtct tactgacatc cactttgcct ttctctccac     1020
aggtgtccac tcccagttca attacagctc ttaaggctag agtacttaat acgactcact     1080
ataggctagc ctcgagaatt cacgcgtttc agaggagggg agagaaagag tactcagtag     1140
ggactgagca ctaaatgctt attttaaaag aaatgtaaag agcagaaagc aattcaggct     1200
accctgcctt ttgtgctggc tagcactccg gtcggtgtca gcagcacgtg gcattgaaca     1260
ttgcaatgtg gagcccaaac cacagaaaat ggggtgaaat tggccaactt tctattaact     1320
tatgttggca attttgccac caacagtaag ctggcccgtc gacccgggcg gccgcttccc     1380
tttagtgagg gttaatgctt cgagcagaca tgataagata cattgatgag tttggacaaa     1440
ccacaactag aatgcagtga aaaaaatgct ttatttgtga aatttgtgat gctattgctt     1500
tatttgtaac cattataagc tgcaataaac aagttaacaa caacaattgc attcatttta     1560
tgtttcaggt tcaggggggag atgtgggagg ttttttaaag caagtaaaac ctctacaaat     1620
gtggtaaaat ccgataagga tcgatccggg ctggcgtaat agcgaagagg cccgcaccga     1680
tcgcccttcc caacagttgc gcagcctgaa tggcgaatgg acgcgccctg tagcggcgca     1740
ttaagcgcgg cgggtgtggt ggttacgcgc agcgtgaccg ctacacttgc cagcgcccta     1800
gcgcccgctc ctttcgcttt cttcccttcc tttctcgcca cgttcgccgg ctttccccgt     1860
caagctctaa atcgggggct ccctttaggg ttccgattta gtgctttacg gcacctcgac     1920
cccaaaaaac ttgattaggg tgatggttca cgtagtgggc catcgccctg atagacggtt     1980
tttcgccctt tgacgttgga gtccacgttc tttaatagtg gactcttgtt ccaaactgga     2040
acaacactca accctatctc ggtctattct tttgatttat aagggatttt gccgatttcg     2100
gcctattggt taaaaaatga gctgatttaa caaaaattta acgcgaattt taacaaaata     2160
ttaacgctta caatttcctg atgcggtatt ttctccttac gcatctgtgc ggtatttcac     2220
accgcatacg cggatctgcg cagcaccatg gcctgaaata acctctgaaa gaggaacttg     2280
gttaggtacc ttctgaggcg gaaagaacca gctgtggaat gtgtgtcagt tagggtgtgg     2340
aaagtcccca ggctccccag caggcagaag tatgcaaagc atgcatctca attagtcagc     2400
aaccaggtgt ggaaagtccc caggctcccc agcaggcaga agtatgcaaa gcatgcatct     2460
caattagtca gcaaccatag tcccgcccct aactccgccc atcccgcccc taactccgcc     2520
cagttccgcc cattctccgc cccatggctg actaattttt tttatttatg cagaggccga     2580
ggccgcctcg gcctctgagc tattccagaa gtagtgagga ggcttttttg gaggcctagg     2640
cttttgcaaa aagcttgatt cttctgacac aacagtctcg aacttaaggc tagagccacc     2700
atgattgaac aagatggatt gcacgcaggt tctccggccg cttgggtgga gaggctattc     2760
ggctatgact gggcacaaca gacaatcggc tgctctgatg ccgccgtgtt ccggctgtca     2820
gcgcaggggc gcccggttct ttttgtcaag accgacctgt ccggtgccct gaatgaactg     2880
caggacgagg cagcgcggct atcgtggctg gccacgacgg gcgttccttg cgcagctgtg     2940
ctcgacgttg tcactgaagc gggaagggac tggctgctat tgggcgaagt gccggggcag     3000
```

```
gatctcctgt catctcacct tgctcctgcc gagaaagtat ccatcatggc tgatgcaatg    3060
cggcggctgc atacgcttga tccggctacc tgcccattcg accaccaagc gaaacatcgc    3120
atcgagcgag cacgtactcg gatggaagcc ggtcttgtcg atcaggatga tctggacgaa    3180
gagcatcagg ggctcgcgcc agccgaactg ttcgccaggc tcaaggcgcg catgcccgac    3240
ggcgaggatc tcgtcgtgac ccatggcgat gcctgcttgc cgaatatcat ggtgaaaat    3300 ggccgctttt ctggattcat cgactgtggc cggctgggtg tggcggaccg ctatcaggac    3360
atagcgttgg ctacccgtga tattgctgaa gagcttggcg gcgaatgggc tgaccgcttc    3420
ctcgtgcttt acggtatcgc cgctcccgat tcgcagcgca tcgccttcta tcgccttctt    3480
gacgagttct tctgagcggg actctggggt tcgaaatgac cgaccaagcg acgcccaacc    3540
tgccatcacg atggccgcaa taaaatatct ttattttcat tacatctgtg tgttggtttt    3600
ttgtgtgaat cgatagcgat aaggatccgc gtatggtgca ctctcagtac aatctgctct    3660
gatgccgcat agttaagcca gccccgacac ccgccaacac ccgctgacgc gccctgacgg    3720
gcttgtctgc tcccggcatc cgcttacaga caagctgtga ccgtctccgg gagctgcatg    3780
tgtcagaggt tttcaccgtc atcaccgaaa cgcgcgagac gaaagggcct cgtgatacgc    3840
ctatttttat aggttaatgt catgataata atggtttctt agacgtcagg tggcactttt    3900
cggggaaatg tgcgcggaac ccctatttgt ttattttct aaatacattc aaatatgtat    3960
ccgctcatga caataaacc ctgataaatg cttcaataat attgaaaaag gaagagtatg    4020
agtattcaac atttccgtgt cgcccttatt ccctttttg cggcattttg ccttcctgtt    4080
tttgctcacc cagaaacgct ggtgaaagta aaagatgctg aagatcagtt gggtgcacga    4140
gtgggttaca tcgaactgga tctcaacagc ggtaagatcc ttgagagttt tcgccccgaa    4200
gaacgttttc caatgatgag cacttttaaa gttctgctat gtggcgcggt attatcccgt    4260
attgacgccg ggcaagagca actcggtcgc cgcatacact attctcagaa tgacttggtt    4320
gagtactcac cagtcacaga aaagcatctt acggatggca tgacagtaag agaattatgc    4380
agtgctgcca taaccatgag tgataacact gcggccaact tacttctgac aacgatcgga    4440
ggaccgaagg agctaaccgc ttttttgcac aacatggggg atcatgtaac tcgccttgat    4500
cgttgggaac cggagctgaa tgaagccata ccaaacgacg agcgtgacac cacgatgcct    4560
gtagcaatgg caacaacgtt gcgcaaacta ttaactggcg aactacttac tctagcttcc    4620
cggcaacaat taatagactg gatggaggcg gataaagttg caggaccact tctgcgctcg    4680
gcccttccgg ctggctggtt tattgctgat aaatctggag ccggtgagcg tgggtctcgc    4740
ggtatcattg cagcactggg gccagatggt aagccctccc gtatcgtagt tatctacacg    4800
acggggagtc aggcaactat ggatgaacga atagacaga tcgctgagat aggtgcctca    4860
ctgattaagc attggtaact gtcagaccaa gtttactcat atatacttta gattgattta    4920
aaacttcatt tttaatttaa aaggatctag gtgaagatcc ttttttgataa tctcatgacc    4980 aaaatccctt aacgtgagtt ttcgttccac tgagcgtcag accccgtaga aaagatcaaa    5040
ggatcttctt gagatccttt ttttctgcgc gtaatctgct gcttgcaaac aaaaaaacca    5100
ccgctaccag cggtggtttg tttgccggat caagagctac caactctttt tccgaaggta    5160
actggcttca gcagagcgca gataccaaat actgttcttc tagtgtagcc gtagttaggc    5220
caccacttca agaactctgt agcaccgcct acatacctcg ctctgctaat cctgttacca    5280
gtggctgctg ccagtggcga taagtcgtgt cttaccgggt tggactcaag acgatagtta    5340
```

-continued

| | |
|---|---|
| ccggataagg cgcagcggtc gggctgaacg gggggttcgt gcacacagcc cagcttggag | 5400 |
| cgaacgacct acaccgaact gagataccta cagcgtgagc tatgagaaag cgccacgctt | 5460 |
| cccgaaggga gaaaggcgga caggtatccg gtaagcggca gggtcggaac aggagagcgc | 5520 |
| acgagggagc ttccaggggg aaacgcctgg tatctttata gtcctgtcgg gtttcgccac | 5580 |
| ctctgacttg agcgtcgatt tttgtgatgc tcgtcagggg ggcggagcct atggaaaaac | 5640 |
| gccagcaacg cggccttttt acggttcctg gccttttgct ggccttttgc tcacatggct | 5700 |
| cgacagatct | 5710 |

<210> SEQ ID NO 17
<211> LENGTH: 5819
<212> TYPE: DNA
<213> ORGANISM: Homo sapiens

<400> SEQUENCE: 17

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg accccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg cccctattg acgtcaatga | 420 |
| cggtaaatgg cccgcctggc attatgccca gtacatgacc ttacgggact ttcctacttg | 480 |
| gcagtacatc tacgtattag tcatcgctat taccatggtg atgcggtttt ggcagtacac | 540 |
| caatgggcgt ggatagcggt ttgactcacg gggatttcca agtctccacc ccattgacgt | 600 |
| caatgggagt ttgttttggc accaaaatca acgggacttt ccaaaatgtc gtaacaactg | 660 |
| cgatcgcccg ccccgttgac gcaaatgggc ggtaggcgtg tacggtggga ggtctatata | 720 |
| agcagagctc gtttagtgaa ccgtcagatc actagaagct ttattgcggt agtttatcac | 780 |
| agttaaattg ctaacgcagt cagtgcttct gacacaacag tctcgaactt aagctgcagt | 840 |
| gactctctta aggtagcctt gcagaagttg gtcgtgaggc actgggcagg taagtatcaa | 900 |
| ggttacaaga caggtttaag gagaccaata gaaactgggc ttgtcgagac agagaagact | 960 |
| cttgcgtttc tgataggcac ctattggtct tactgacatc cactttgcct ttctctccac | 1020 |
| aggtgtccac tcccagttca attacagctc ttaaggctag agtacttaat acgactcact | 1080 |
| ataggctagc ctcgagaatt cacgcgttgc acgtcagtgt cctcagttgc atcctggttc | 1140 |
| cggtccgaca gccgagcgat ggcctcattg tcataatgaa tcacactgct gtcctcctcc | 1200 |
| ttgttctccc cctcgttttc atccttgaat agctcttcag tgccaaattt gagaatgtcg | 1260 |
| tcaagctcct gcttggacat ggagcctgcc ttggagccca gccaggccg cacaaccagg | 1320 |
| tgtgtcagca tcatctttct cttggccact tgtgtgattc gctcttccac tgacgcgcga | 1380 |
| gtcacaaacc ggtaaatcat cactttgttg gcctggccaa tccgatgagc ccggctaaag | 1440 |
| gcctggatgt cattatgggg gttccagtcg acccggcgg ccgcttccct ttagtgaggg | 1500 |
| ttaatgcttc gagcagacat gataagatac attgatgagt ttggacaaac cacaactaga | 1560 |
| atgcagtgaa aaaaatgctt tatttgtgaa atttgtgatg ctattgcttt atttgtaacc | 1620 |
| attataagct gcaataaaca agttaacaac aacaattgca ttcatttat gtttcaggtt | 1680 |
| caggggggaga tgtgggaggt tttttaaagc aagtaaaacc tctacaaatg tggtaaaatc | 1740 |

```
cgataaggat cgatccgggc tggcgtaata gcgaagaggc ccgcaccgat cgcccttccc    1800
aacagttgcg cagcctgaat ggcgaatgga cgcgccctgt agcggcgcat taagcgcggc    1860
gggtgtggtg gttacgcgca gcgtgaccgc tacacttgcc agcgccctag cgcccgctcc    1920
tttcgctttc ttcccttcct ttctcgccac gttcgccggc tttccccgtc aagctctaaa    1980 tcggggctc cctttagggt tccgatttag tgctttacgg cacctcgacc ccaaaaaact    2040
tgattagggt gatggttcac gtagtgggcc atcgccctga tagacggttt tcgcccttt    2100 gacgttggag tccacgttct ttaatagtgg actcttgttc caaactggaa caacactcaa    2160
ccctatctcg gtctattctt tgatttata agggattttg ccgatttcgg cctattggtt    2220
aaaaaatgag ctgatttaac aaaaatttaa cgcgaatttt aacaaaatat taacgcttac    2280
aatttcctga tgcggtattt tctccttacg catctgtgcg gtatttcaca ccgcatacgc    2340
ggatctgcgc agcaccatgg cctgaaataa cctctgaaag aggaacttgg ttaggtacct    2400
tctgaggcgg aaagaaccag ctgtggaatg tgtgtcagtt agggtgtgga agtccccag    2460 gctccccagc aggcagaagt atgcaaagca tgcatctcaa ttagtcagca accaggtgtg    2520
gaaagtcccc aggctcccca gcaggcagaa gtatgcaaag catgcatctc aattagtcag    2580
caaccatagt cccgccccta actccgccca tcccgcccct aactccgccc agttccgccc    2640
attctccgcc ccatggctga ctaatttttt ttatttatgc agaggccgag gccgcctcgg    2700
cctctgagct attccagaag tagtgaggag gcttttttgg aggcctaggc ttttgcaaaa    2760
agcttgattc ttctgacaca acagtctcga acttaaggct agagccacca tgattgaaca    2820
agatggattg cacgcaggtt ctccggccgc ttgggtggag aggctattcg gctatgactg    2880
ggcacaacag acaatcggct gctctgatgc cgccgtgttc cggctgtcag cgcaggggcg    2940
cccggttctt tttgtcaaga ccgacctgtc cggtgccctg aatgaactgc aggacgaggc    3000
agcgcggcta tcgtggctgg ccacgacggg cgttccttgc gcagctgtgc tcgacgttgt    3060
cactgaagcg ggaagggact ggctgctatt gggcgaagtg ccggggcagg atctcctgtc    3120
atctcacctt gctcctgccg agaaagtatc catcatggct gatgcaatgc ggcggctgca    3180
tacgcttgat ccggctacct gcccattcga ccaccaagcg aaacatcgca tcgagcgagc    3240
acgtactcgg atggaagccg gtcttgtcga tcaggatgat ctggacgaag agcatcaggg    3300
gctcgcgcca gccgaactgt tcgccaggct caaggcgcgc atgcccgacg gcgaggatct    3360
cgtcgtgacc catggcgatg cctgcttgcc gaatatcatg gtggaaaatg gccgcttttc    3420
tggattcatc gactgtggcc ggctgggtgt ggcggaccgc tatcaggaca tagcgttggc    3480
tacccgtgat attgctgaag agcttggcgg cgaatgggct gaccgcttcc tcgtgcttta    3540
cggtatcgcc gctcccgatt cgcagcgcat cgccttctat cgccttcttg acgagttctt    3600
ctgagcggga ctctgggtt cgaaatgacc gaccaagcga cgcccaacct gccatcacga    3660
tggccgcaat aaaatatctt tattttcatt acatctgtgt gttggttttt tgtgtgaatc    3720
gatagcgata aggatccgcg tatggtgcac tctcagtaca atctgctctg atgccgcata    3780
gttaagccag ccccgacacc cgccaacacc cgctgacgcg ccctgacggg cttgtctgct    3840
cccggcatcc gcttacagac aagctgtgac cgtctccggg agctgcatgt gtcagaggtt    3900
ttcaccgtca tcaccgaaac gcgcgagacg aaagggcctc gtgatacgcc tatttttata    3960
ggttaatgtc atgataataa tggtttctta cgtcaggt ggcactttc ggggaaatgt    4020 gcgcggaacc cctatttgtt tatttttcta aatacattca aatatgtatc cgctcatgag    4080
```

-continued

| | |
|---|---|
| acaataaccc tgataaatgc ttcaataata ttgaaaaagg aagagtatga gtattcaaca | 4140 |
| tttccgtgtc gcccttattc ccttttttgc ggcattttgc cttcctgttt ttgctcaccc | 4200 |
| agaaacgctg gtgaaagtaa aagatgctga agatcagttg ggtgcacgag tgggttacat | 4260 |
| cgaactggat ctcaacagcg gtaagatcct tgagagtttt cgccccgaag aacgttttcc | 4320 |
| aatgatgagc acttttaaag ttctgctatg tggcgcggta ttatcccgta ttgacgccgg | 4380 |
| gcaagagcaa ctcggtcgcc gcatacacta ttctcagaat gacttggttg agtactcacc | 4440 |
| agtcacagaa aagcatctta cggatggcat gacagtaaga gaattatgca gtgctgccat | 4500 |
| aaccatgagt gataacactg cggccaactt acttctgaca acgatcggag gaccgaagga | 4560 |
| gctaaccgct tttttgcaca acatggggga tcatgtaact cgccttgatc gttgggaacc | 4620 |
| ggagctgaat gaagccatac caaacgacga gcgtgacacc acgatgcctg tagcaatggc | 4680 |
| aacaacgttg cgcaaactat taactggcga actacttact ctagcttccc ggcaacaatt | 4740 |
| aatagactgg atggaggcgg ataaagttgc aggaccactt ctgcgctcgg cccttccggc | 4800 |
| tggctggttt attgctgata aatctggagc cggtgagcgt gggtctcgcg gtatcattgc | 4860 |
| agcactgggg ccagatggta agccctcccg tatcgtagtt atctacacga cggggagtca | 4920 |
| ggcaactatg gatgaacgaa atagacagat cgctgagata ggtgcctcac tgattaagca | 4980 |
| ttggtaactg tcagaccaag tttactcata tatactttag attgatttaa aacttcattt | 5040 |
| ttaatttaaa aggatctagg tgaagatcct ttttgataat ctcatgacca aaatccctta | 5100 |
| acgtgagttt tcgttccact gagcgtcaga ccccgtagaa aagatcaaag gatcttcttg | 5160 |
| agatcctttt tttctgcgcg taatctgctg cttgcaaaca aaaaaaccac cgctaccagc | 5220 |
| ggtggtttgt ttgccggatc aagagctacc aactcttttt ccgaaggtaa ctggcttcag | 5280 |
| cagagcgcag ataccaaata ctgttcttct agtgtagccg tagttaggcc accacttcaa | 5340 |
| gaactctgta gcaccgccta catacctcgc tctgctaatc ctgttaccag tggctgctgc | 5400 |
| cagtggcgat aagtcgtgtc ttaccgggtt ggactcaaga cgatagttac cggataaggc | 5460 |
| gcagcggtcg ggctgaacgg ggggttcgtg cacacagccc agcttggagc gaacgaccta | 5520 |
| caccgaactg agatacctac agcgtgagct atgagaaagc gccacgcttc ccgaagggag | 5580 |
| aaaggcggac aggtatccgg taagcggcag ggtcggaaca ggagagcgca cgagggagct | 5640 |
| tccaggggga aacgcctggt atctttatag tcctgtcggg tttcgccacc tctgacttga | 5700 |
| gcgtcgattt ttgtgatgct cgtcaggggg gcggagccta tggaaaaacg ccagcaacgc | 5760 |
| ggccttttta cggttcctgg ccttttgctg gccttttgct cacatggctc gacagatct | 5819 |

<210> SEQ ID NO 18
<211> LENGTH: 5627
<212> TYPE: DNA
<213> ORGANISM: Homo sapiens

<400> SEQUENCE: 18

| | |
|---|---|
| tcaatattgg ccattagcca tattattcat tggttatata gcataaatca atattggcta | 60 |
| ttggccattg catacgttgt atctatatca taatatgtac atttatattg gctcatgtcc | 120 |
| aatatgaccg ccatgttggc attgattatt gactagttat taatagtaat caattacggg | 180 |
| gtcattagtt catagcccat atatggagtt ccgcgttaca taacttacgg taaatggccc | 240 |
| gcctggctga ccgcccaacg acccccgccc attgacgtca ataatgacgt atgttcccat | 300 |
| agtaacgcca atagggactt tccattgacg tcaatgggtg gagtatttac ggtaaactgc | 360 |
| ccacttggca gtacatcaag tgtatcatat gccaagtccg ccccctattg acgtcaatga | 420 |

```
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggctag agtacttaat acgactcact   1080
ataggctagc ctcgagaatt cacgcgtcag gcgggaaaca gagtggagag ctcagtaggc   1140
cgtctgagac tgctgctggc ggtagccacc gcggcgcatg tagccctcgt ttttgcggta   1200
gccgtccttc tggtctcgga agtagccccc gtaggtgccc tgcttgtggt caaacacccg   1260
ttcgttgttc tccagtcgac ccgggcggcc gcttcccttt agtgagggtt aatgcttcga   1320
gcagacatga taagatacat tgatgagttt ggacaaacca caactagaat gcagtgaaaa   1380
aaatgcttta tttgtgaaat ttgtgatgct attgctttat tgtaaccat tataagctgc   1440 aataaacaag ttaacaacaa caattgcatt cattttatgt ttcaggttca gggggagatg   1500
tgggaggttt tttaaagcaa gtaaaacctc tacaaatgtg gtaaaatccg ataaggatcg   1560
atccgggctg cgtaatagc gaagaggccc gcaccgatcg cccttcccaa cagttgcgca   1620
gcctgaatgg cgaatggacg cgccctgtag cggcgcatta agcgcggcgg gtgtggtggt   1680
tacgcgcagc gtgaccgcta cacttgccag cgccctagcg cccgctcctt tcgctttctt   1740
cccttccttt ctcgccacgt tcgccggctt tccccgtcaa gctctaaatc gggggctccc   1800
tttagggttc cgatttagtg ctttacggca cctcgacccc aaaaaacttg attagggtga   1860
tggttcacgt agtgggccat cgccctgata acggttttt cgccctttga cgttggagtc   1920
cacgttcttt aatagtggac tcttgttcca aactggaaca acactcaacc ctatctcggt   1980
ctattctttt gatttataag ggattttgcc gatttcggcc tattggttaa aaaatgagct   2040
gatttaacaa aaatttaacg cgaattttaa caaaatatta acgcttacaa tttcctgatg   2100
cggtattttc tccttacgca tctgtgcggt atttcacacc gcatacgcgg atctgcgcag   2160
caccatggcc tgaaataacc tctgaaagag gaacttggtt aggtaccttc tgaggcggaa   2220
agaaccagct gtggaatgtg tgtcagttag ggtgtggaaa gtccccaggc tccccagcag   2280
gcagaagtat gcaaagcatg catctcaatt agtcagcaac caggtgtgga agtccccag   2340 gctccccagc aggcagaagt atgcaaagca tgcatctcaa ttagtcagca accatagtcc   2400
cgcccctaac tccgcccatc ccgccctaa ctccgcccag ttccgcccat tctccgcccc   2460
atggctgact aatttttttt atttatgcag aggccgaggc cgcctcggcc tctgagctat   2520
tccagaagta gtgaggaggc ttttttggag gcctaggctt ttgcaaaaag cttgattctt   2580
ctgacacaac agtctcgaac ttaaggctag agccaccatg attgaacaag atggattgca   2640
cgcaggttct ccggccgctt gggtggagag gctattcggc tatgactggg cacaacagac   2700
aatcggctgc tctgatgccg ccgtgttccg gctgtcagcg caggggcgcc cggttctttt   2760
```

```
tgtcaagacc gacctgtccg gtgccctgaa tgaactgcag gacgaggcag cgcggctatc    2820
gtggctggcc acgacgggcg ttccttgcgc agctgtgctc gacgttgtca ctgaagcggg    2880
aagggactgg ctgctattgg gcgaagtgcc ggggcaggat ctcctgtcat ctcaccttgc    2940
tcctgccgag aaagtatcca tcatggctga tgcaatgcgg cggctgcata cgcttgatcc    3000
ggctacctgc ccattcgacc accaagcgaa acatcgcatc gagcgagcac gtactcggat    3060
ggaagccggt cttgtcgatc aggatgatct ggacgaagag catcagggc tcgcgccagc     3120 cgaactgttc gccaggctca aggcgcgcat gcccgacggc gaggatctcg tcgtgaccca    3180
tggcgatgcc tgcttgccga atatcatggt ggaaaatggc cgcttttctg gattcatcga    3240
ctgtggccgg ctgggtgtgg cggaccgcta tcaggacata gcgttggcta cccgtgatat    3300
tgctgaagag cttggcggcg aatgggctga ccgcttcctc gtgctttacg gtatcgccgc    3360
tcccgattcg cagcgcatcg ccttctatcg ccttcttgac gagttcttct gagcgggact    3420
ctggggttcg aaatgaccga ccaagcgacg cccaacctgc catcacgatg gccgcaataa    3480
aatatcttta ttttcattac atctgtgtgt tggtttttg tgtgaatcga tagcgataag      3540
gatccgcgta tggtgcactc tcagtacaat ctgctctgat gccgcatagt taagccagcc    3600
ccgacacccg ccaacacccg ctgacgcgcc ctgacgggct tgtctgctcc cggcatccgc    3660
ttacagacaa gctgtgaccg tctccgggag ctgcatgtgt cagaggtttt caccgtcatc    3720
accgaaacgc gcgagacgaa agggcctcgt gatacgccta ttttatagg ttaatgtcat      3780 gataataatg gtttcttaga cgtcaggtgg cacttttcgg ggaaatgtgc gcggaacccc    3840
tatttgttta ttttcctaaa tacattcaaa tatgtatccg ctcatgagac aataaccctg    3900
ataaatgctt caataatatt gaaaaaggaa gagtatgagt attcaacatt tccgtgtcgc    3960
ccttattccc ttttttgcgg catttgcct tcctgttttt gctcacccag aaacgctggt      4020
gaaagtaaaa gatgctgaag atcagttggg tgcacgagtg ggttacatcg aactggatct    4080
caacagcggt aagatccttg agagttttcg ccccgaagaa cgttttccaa tgatgagcac    4140
ttttaaagtt ctgctatgtg gcgcggtatt atcccgtatt gacgccgggc aagagcaact    4200
cggtcgccgc atacactatt ctcagaatga cttggttgag tactcaccag tcacagaaaa    4260
gcatcttacg gatggcatga cagtaagaga attatgcagt gctgccataa ccatgagtga    4320
taacactgcg gccaacttac ttctgacaac gatcggagga ccgaaggagc taaccgcttt    4380
tttgcacaac atgggggatc atgtaactcg ccttgatcgt tgggaaccgg agctgaatga    4440
agccatacca aacgacgagc gtgacaccac gatgcctgta gcaatggcaa caacgttgcg    4500
caaactatta actggcgaac tacttactct agcttcccgg caacaattaa tagactggat    4560
ggaggcggat aaagttgcag gaccacttct gcgctcggcc cttccggctg gctggtttat    4620
tgctgataaa tctggagccg gtgagcgtgg gtctcgcggt atcattgcag cactggggcc    4680
agatggtaag ccctcccgta tcgtagttat ctacacgacg gggagtcagg caactatgga    4740
tgaacgaaat agacagatcg ctgagatagg tgcctcactg attaagcatt ggtaactgtc    4800
agaccaagtt tactcatata tactttagat tgatttaaaa cttcattttt aatttaaaag    4860
gatctaggtg aagatccttt ttgataatct catgaccaaa atcccttaac gtgagttttc    4920
gttccactga gcgtcagacc ccgtagaaaa gatcaaagga tcttcttgag atcctttttt    4980
tctgcgcgta atctgctgct tgcaaacaaa aaaaccaccg ctaccagcgg tggtttgttt    5040
gccggatcaa gagctaccaa ctcttttcc gaaggtaact ggcttcagca gagcgcagat     5100
accaaatact gttcttctag tgtagccgta gttaggccac cacttcaaga actctgtagc    5160
```

```
accgcctaca tacctcgctc tgctaatcct gttaccagtg gctgctgcca gtggcgataa      5220
gtcgtgtctt accgggttgg actcaagacg atagttaccg gataaggcgc agcggtcggg      5280
ctgaacgggg ggttcgtgca cacagcccag cttggagcga acgacctaca ccgaactgag      5340
atacctacag cgtgagctat gagaaagcgc cacgcttccc gaagggagaa aggcggacag      5400
gtatccggta agcggcaggg tcggaacagg agagcgcacg agggagcttc caggggggaaa     5460 cgcctggtat ctttatagtc ctgtcgggtt tcgccacctc tgacttgagc gtcgattttt      5520
gtgatgctcg tcaggggggc ggagcctatg gaaaaacgcc agcaacgcgg cctttttacg      5580
gttcctggcc ttttgctggc cttttgctca catggctcga cagatct                   5627
```

```
<210> SEQ ID NO 19
<211> LENGTH: 29
<212> TYPE: DNA
<213> ORGANISM: Homo sapiens

<400> SEQUENCE: 19
cgggtcgaca ggtccactgc aggggggtta                                         29

<210> SEQ ID NO 20
<211> LENGTH: 31
<212> TYPE: DNA
<213> ORGANISM: Homo sapiens

<400> SEQUENCE: 20
cgcacgcgtt tcccctttgg aagagagagc a                                     31

<210> SEQ ID NO 21
<211> LENGTH: 29
<212> TYPE: DNA
<213> ORGANISM: Homo sapiens

<400> SEQUENCE: 21
cgggtcgacg ggccagctta ctgttggtg                                         29

<210> SEQ ID NO 22
<211> LENGTH: 32
<212> TYPE: DNA
<213> ORGANISM: Homo sapiens

<400> SEQUENCE: 22
cgcacgcgtt tcagaggagg ggagagaaag ag                                    32

<210> SEQ ID NO 23
<211> LENGTH: 31
<212> TYPE: DNA
<213> ORGANISM: Homo sapiens

<400> SEQUENCE: 23
cgggtcgact ggaaccccca taatgacatc c                                     31

<210> SEQ ID NO 24
<211> LENGTH: 31
<212> TYPE: DNA
<213> ORGANISM: Homo sapiens

<400> SEQUENCE: 24
cgcacgcgtt gcacgtcagt gtcctcagtt g                                     31

<210> SEQ ID NO 25
```

```
<211> LENGTH: 30
<212> TYPE: DNA
<213> ORGANISM: Homo sapiens

<400> SEQUENCE: 25
cgggtcgact ggagaacaac gaacgggtgt                                         30

<210> SEQ ID NO 26
<211> LENGTH: 29
<212> TYPE: DNA
<213> ORGANISM: Homo sapiens

<400> SEQUENCE: 26
cgcacgcgtc aggcgggaaa cagagtgga                                          29

<210> SEQ ID NO 27
<211> LENGTH: 5975
<212> TYPE: DNA
<213> ORGANISM: Homo sapiens
<300> PUBLICATION INFORMATION:
<308> DATABASE ACCESSION NUMBER: GenBank/XM_040709
<309> DATABASE ENTRY DATE: 2002-02-07
<313> RELEVANT RESIDUES: (1)..(5975)

<400> SEQUENCE: 27
gctctttgcc gagggcgtgt ggtgagagtc cccacagcga ccctggttcg agtggtgggc        60
actgagctgg tcatcccctg caacgtcagt gactatgatg ccccagcga gcaaaacttt       120 gactggagct tctcatcttt ggggagcagc tttgtggagc ttgcaagcac ctgggaggtg       180
gggttcccag cccagctgta ccaggagcgg ctgcagaggg gcgagatcct gttaaggcgg       240
actgccaacg acgccgtgga gctccacata aagaacgtcc agccttcaga ccaaggccac       300
tacaaatgtt caacccccag cacagatgcc actgtccagg aaactatga ggacacagtg        360 caggttaaag tgctggccga ctccctgcac gtgggcccca gcgcgcggcc ccgccgagc        420 ctgagcctgc gggagggga gcccttcgag ctgcgctgca ccgccgcctc cgcctcgccg        480
ctgcacacgc acctggcgct gctgtgggag gtgcaccgcg gcccggccag gcggagcgtc       540
ctcgccctga cccacgaggg caggttccac ccgggcctgg ggtacgagca gcgctaccac       600
agtggggacg tgcgcctcga caccgtgggc agcgacgcct accgcctctc agtgtcccgg       660
gctctgtctg ccgaccaggg ctcctacagg tgtatcgtca gcgagtggat cgccgagcag       720
ggcaactggc aggaaatcca agaaaaggcc gtggaagttg ccaccgtggt gatccagcca       780
tcagttctgc gagcagctgt gcccaagaat gtgtctgtgg ctgaaggaaa ggaactggac       840
ctgacctgta acatcacaac agaccgagcc gatgacgtcc ggcccgaggt gacgtggtcc       900
ttcagcagga tgcctgacag cacctacct ggctcccgcg tgttggcgcg gcttgaccgt        960
gattccctgg tgcacagctc gcctcatgtt gctttgagtc atgtggatgc acgctcctac      1020
catttactgg ttcgggatgt tagcaaagaa aactctggct actattactg ccacgtgtcc      1080
ctgtgggcac ccggacacaa caggagctgg cacaaagtgg cagaggccgt gtcttcccca      1140
gctggtgtgg gtgtgacctg ctagaaacca gactaccagg tgtacctgaa tgcttccaag      1200
gtccccgggt ttgcggatga ccccacagag ctggcatgcc gggtggtgga cacgaagagt      1260
ggggaggcga atgtccgatt cacgtttcg tggtactaca ggatgaaccg gcgcagcgac       1320
aatgtggtga ccagcgagct gcttgcagtc atggacgggg actggacgct aaaatatgga      1380
gagaggagca agcagcgggc ccaggatgga gactttattt tttctaagga acatacagac      1440
acgttcaatt tccggatcca aaggactaca gaggaagaca gaggcaatta ttactgtgtt      1500
```

```
gtgtctgcct ggaccaaaca gcggaacaac agctgggtga aaagcaagga tgtcttctcc    1560
aagcctgtta acatattttg ggcattagaa gattccgtgc ttgtggtgaa ggcgaggcag    1620
ccaaagcctt tctttgctgc cggaaataca tttgagatga cttgcaaagt atcttccaag    1680
aatattaagt cgccacgcta ctctgttctc atcatggctg agaagcctgt cggcgacctc    1740
tccagtccca atgaaacgaa gtacatcatc tctctggacc aggattctgt ggtgaagctg    1800
gagaattgga cagatgcatc acgggtggat ggcgttgttt tagaaaaagt gcaggaggat    1860
gagttccgct atcgaatgta ccagactcag gtctcagacg cagggctgta ccgctgcatg    1920
gtgacagcct ggtctcctgt caggggcagc ctttggcgag aagcagcaac cagtctctcc    1980
aatcctattg agatagactt ccaaacctca ggtcctatat ttaatgcttc tgtgcattca    2040
gacacaccat cagtaattcg gggagatctg atcaaattgt tctgtatcat cactgtcgag    2100
ggagcagcac tggatccaga tgacatggcc tttgatgtgt cctggtttgc ggtgcactct    2160
tttggcctgg acaaggctcc tgtgctcctg tcttccctgg atcggaaggg catcgtgacc    2220
acctcccgga gggactggaa gagcgacctc agcctggagc gcgtgagtgt gctggaattc    2280
ttgctgcaag tgcatggctc cgaggaccag gactttggca actactactg ttccgtgact    2340
ccatgggtga agtcaccaac aggttcctgg cagaaggagg cagagatcca ctccaagccc    2400
gtttttataa ctgtgaagat ggatgtgctg aacgccttca gtatccctt gctgatcggc    2460 gtcggtctgt ccacggtcat cgggctcctg tcctgtctca tcgggtactg cagctcccac    2520
tggtgttgta agaaggaggt tcaggagaca cggcgcgagc cgcaggct catgtcgatg    2580 gagatggact aggctggccc gggaggggag tgacagaggg acgttctagg agcaattggg    2640
gcaagaagag gacagtgata ttttaaaaca agtgtgtta cactaaaaac cagtcctctc    2700
taatctcagg tgggacttgg cgctctctct tttctgcatg tcaagttctg agcgcggaca    2760
tgtttaccag cacacggctc ttcttcccac ggcactttct gatgtaacaa tcgagtgtgt    2820
gttttcccaa ctgcagcttt ttaatggtta accttcatct aattttttt ctcccactgg    2880 tttatagatc ctctgacttg tgtgtgttta tagcttttgt ttcgcggggt tgtggtgagg    2940 aagggtgat ggcatgcgga gttctttatc ttcagtgaga atgtgcctgc ccgcctgaga    3000
gccagcttcc gcgttggagg cacgtgttca gagagctgct gagcgccacc ctctacccgg    3060
ctgacagaca acacagacct gtgccgaagg ctaatttgtg gcttttacga ccctaccca    3120 cccctgttt tcagggtttt agactacatt tgaaatccaa acttggagta tataacttct    3180
tattgagccc aactgctttt ttttttttt tttttgcttc tctgcccctt ttccatttct    3240
tttgtatttg ttttctgtga gagcactgaa atggcagccc tggaatctac aatttggctc    3300
tccactgagc accttatctt gccaccttag ccttaagaat gaatatgaag aaaaatacac    3360
agccacctct gtccagggca gtaagaaggg ctgcaaggaa gggaggatg gggacaagga    3420 aaggatcaga tacctgctcc agtagttgtg aggccactgt gtctcagggg actccaggag    3480
gagcagaaga gggatcccac gaagttattc ttacgcagct ggggccagga gggtcagagt    3540
ggtgccaggt gcaagttagg ctaaagaagc caccactatt cctctctctt gcccattgtg    3600
gggggcaaag gcattggtca ccaagagtct gcaggggga cccacagata tgccatgtcc    3660
ttcacacgtg cttgggctcc ttaacctgaa ggcaaattgc tacttgcaag actgactgac    3720
ttcaaggaat cagaaattac ctagaagcac catgtttttt ctatgaccct ttcagtcctt    3780
caggtcattt taaggtccac tgcagggggt tagtgagaaa gggtatactt tgtggtatgt    3840
```

```
tttgctttcc taatagggac atgaaggaaa cccagcaatt tgctgttatg tgaatggcct    3900
gtagagcaga gtcaagagcg gtgtgctttg cccgactgct cccatcagga ataggagagt    3960
agacagagat cttccacatc ccaggcttct gctgctgctt taaaagctct gtccttggag    4020
cctcccgctc cctgaagtgt ctcgcccct gcacagcact ggcctttcgg aagcatccca     4080
gtagggtttt ctgaggctcg ctggtgactc atgccctaat tgcaatcctc tgcttttatc    4140
ttgactttga aggatctaac actgctctct cttccaaagg ggaaaaaaag attcatttgt    4200
tttgagcaat aaactaatac aaaatgatgg ccattcatgt gcagctcttt gtcaccatgg    4260
gccggatgag ttgtgctcct cctggctcac catttccccc tgctccccca cagccggttc    4320
tgcacttatc accgagtcgc ccctggaagc agattcccat tgagttttcc ccaccaaggg    4380
gaccatgcac atggtagaaa cattagattc tgcattgaca gtagcctttc cttgcccgg     4440 gcctgtggtg ggaagacggg caacaagtat accccaccag ggcctgagtg actagaggaa    4500
gaggacgagg ccttgttggc actagatttg ggtattttct gcatgtcata acatatccta    4560
actgctattt cagaagaggc agcttgtagg tgattgtaca agtgagaatt aaagagagaa    4620
cagatattta aacaggtgct gtattagtaa cagccagtgc cctttcagcc cttgcatcta    4680
ttaaaaggag attcaggatt ttattggcac aggcccttct tagtaggaag aaagggtgct    4740
tagctttgga cctgaccggg tgtgtgtaaa accatggact gagtcacagc agacactcga    4800
tggtggtaaa tgtgatgggt gcttacacac tgtaccttt cctttcatac tgatgctgca     4860
gttcagggct ggagttgtta aggcattgac ctccacccac ctgccccatg tccactgggc    4920
tgcccaagct gcatgtcacc tgagggctgg caggaagggg cgagaaatcc cagggcattg    4980
taccaaggac ctagttcctt ctagggtatat aaatttccag gaatgtgtat ttttaatgtg    5040
gtgagatgca ctcttttgtt gtaccaaata gggctcccca ccccaccct gcgacaagtg     5100 ctcttctaga acaggttcct accagcagca ctggtgtgaa tgaaagagag acccagccgc    5160
gtctcacaca ggtggaattg cacttcttaa caaaaaggaa ctttataaaa gtttgggatt    5220 tttttttccta atcataaaaa tagccccaga aagagcctaa gctatgttca gatagaagcc    5280
tcgaaattcc tgtaaattgt ttactttatg atgtttacat acacgtttca ctttgaaaaa    5340
aaatgcaaat cgactttta acaactgttg agatgtttca tgggacagta gaactctgac      5400
tcaccaactg ggctaaattt taatttaaaa atgtatttat ttgagtgtct ttccccccct    5460
caccctcacc atctgagggg ctccctgaga tcttggtaga ggaggcccct cctgcccaga    5520
ccttcgtttg ttccccggt ggcccttgct tcttgctttg cagactgcct gcagccatga      5580
ttttgtcact gacatctgtg agccaaagac tgagccttt tggcaggaat aataagcaat     5640
actacacaac ttgctacttt cagaaaactt ttttttagct tcaccgatga caacagagga    5700
agaagggaac tgggatttgg gtaagttctc ctccactgtt tgaccaaatt ctcagtgata    5760
aatatgtgtg cagatcccta gaagagaaaa cgctgacttc ttttttaagt gtggcacata    5820
aggatctgca gaattttccg tagacaaaga aaggatcttg tgtattttg tccatatcca      5880 atgttatatg aactaattgt attgttttat actgtgacca caaatattat gcaatgcacc    5940
atttgttttt tatttcatta aaggaagttt aattt                               5975
```

<210> SEQ ID NO 28
<211> LENGTH: 2197
<212> TYPE: DNA
<213> ORGANISM: Homo sapiens
<220> FEATURE:
<221> NAME/KEY: misc_feature
<222> LOCATION: (1037)..(1037)
<223> OTHER INFORMATION: a, t, c or g
<220> FEATURE:
<221> NAME/KEY: misc_feature
<222> LOCATION: (1236)..(1236)
<223> OTHER INFORMATION: a, t, c or g
<300> PUBLICATION INFORMATION:
<308> DATABASE ACCESSION NUMBER: GenBank/AB014734
<309> DATABASE ENTRY DATE: 2001-01-06
<313> RELEVANT RESIDUES: (1)..(2197)

<400> SEQUENCE: 28

```
gtgcattcag acacaccatc agtaattcgg ggagatctga tcaaattgtt ctgtatcatc      60
actgtcgagg gagcagcact ggatccagat gacatggcct ttgatgtgtc ctggtttgcg     120
gtgcactctt ttggcctgga caaggctcct gtgctcctgt cttccctgga tcggaagggc     180
atcgtgacca cctcccggag ggactggaag agcgacctca gcctggagcg cgtgagtgtg     240
ctggaattct tgctgcaagt gcatggctcc gaggaccagg actttggcaa ctactactgt     300
tccgtgactc catgggtgaa gtcaccaaca ggttcctggc agaaggaggc agagatccac     360
tccaagcccg tttttataac tgtgaagatg gatgtgctga cgccttcaa gtatcccttg      420
ctgatcggcg tcggtctgtc cacggtcatc gggctcctgt cctgtctcat cgggtactgc     480
agctcccact ggtgttgtaa gaaggaggtt caggagacac ggcgcgagcg ccgcaggctc     540
atgtcgatgg agatggacta ggctggcccg ggaggggagt gacagaggga cgttctagga     600
gcaattgggg caagaagagg acagtgtatat tttaaaacaa agtgtgttac actaaaaacc     660
agtcctctct aatctcaggt gggacttggc gctctctctt ttctgcatgt caagttctga     720
gcgcggacat gtttaccagc acacggctct tcttcccacg gcactttctg atgtaacaat     780
cgagtgtgtg ttttcccaac tgcagctttt taatggttaa ccttcatcta atttttttc      840
tcccactggt ttatagatcc tctgacttgt gtgtgtttat agcttttgtt tcgcggggtt     900
gtggtgagga aggggtgatg gcatgcggag ttctttatct tcagtgagaa tgtgcctgcc     960
cgcctgagag ccagcttccg cgttggaggc acgtgttcag agagctgctg agcgccaccc    1020
tctacccggc tgacagncaa cacagacctg tgccgaaggc taatttgtgg cttttacgac    1080
cctaccccac ccctgttttt caggggttta gactacattt gaaatccaaa cttggagtat    1140
ataacttctt attgagccca actgcttttt tttttttttt tttttgctt ctctgcccct     1200
tttccatttc ttttgtattt gttttctgtg agagcnctga aatggcagcc ctggaatcta    1260
caatttggct ctccactgag caccttatct tgccaccta gccttaagaa tgaatatgaa     1320
gaaaaataca cagccacctc tgtccagggc agtaagaagg gctgcaagga aggggaggat    1380
ggggacaagg aaaggatcag atacctgctc cagtagttgt gaggccactg tgtctcaggg    1440
gactccagga ggagcagaag agggatccca cgaagttatt cttacgcagc tggggccagg    1500
agggtcagag tggtgccagg tgcaagttag gctaaagaag ccaccactat tcctctctct    1560
tgcccattgt gggggcaaa ggcattggtc accaagagtc ttgcaggggg acccacagat     1620
atgccatgtc cttcacacgt gcttgggctc cttaacctga aggcaaattg ctacttgcaa    1680
gactgactga cttcaaggaa tcagaaatta cctagaagca ccatgttttt tctatgacct    1740
tttcagtcct tcaggtcatt ttaaggtcca ctgcagggg ttagtgagaa agggtatact     1800
ttgtggtatg ttttgctttc ctaatagggg catgaaggaa acccagcaat ttgctgttat    1860
gtgaatggcc tgtagagcag agtcaagagc ggtgtgcttt gccgactgc tcccatcagg     1920
aataggagag tagacagaga tcttccacat cccaggcttc tgctgctgct ttaaaagctc    1980
```

-continued

```
tgtccttgga gcctcccgct ccctgaagtg tctcgccccc tgcacagcac tggcctttcg    2040
gaagcatccc agtagggttt tctgaggctc gctggtgact catgccctaa ttgcaatcct    2100
ctgcttttat cttgactttg aaggatctaa cactgctctc tcttccaaag gggaaaaaaa    2160
gattcatttg ttttgagcaa taaactaata caaaatg                             2197
```

<210> SEQ ID NO 29
<211> LENGTH: 6331
<212> TYPE: DNA
<213> ORGANISM: Homo sapiens
<300> PUBLICATION INFORMATION:
<308> DATABASE ACCESSION NUMBER: GenBank/AF006515
<309> DATABASE ENTRY DATE: 1997-11-27
<313> RELEVANT RESIDUES: (1)..(6331)

<400> SEQUENCE: 29

```
atctttgttt gggtctccca tactgcgtat agatgaatgg gtcaggatat ctggaacaaa      60
atatggaggt gaagggtgag atcgggaaac aaagggtatg gccccctagt tcccaaaggg     120
agcagggaga tggaataga attgaaggta ggttttaggc tacttgggag gaggaatatt      180
taggtaattg tggagacttt ctcctgtgtg atgaaggcgg cagacactgt gatcctgtgg     240
gcaagaagta aaaatgacca gctgaggatt tcttttcctc caggactgtg ttggggtgac     300
aggatgcctg ataaggatga cattcggctg ctgccgtcag cattgggtgt gaagaagaga     360
aaacgaggac ccaagaagca gaaggagaac aagccaggaa aaccccgaaa cgcaagaag      420 cgtgacagtg aggaggaatt tggttctgag cgagatgagt accggagaa gtcagagagt      480 gggggcagtg aatatggaac cggaccgggt cggaaacgaa gaaggaagca ccgagaaaaa     540
aaggagaaga agacaaagcg gcggaaaaag ggggagggga tggggggca aaagcaagtg     600 gaacagaagt catcagcaac tctgcttctg acctggggcc tggaggatgt ggagcatgtg     660
ttctctgagg aggattacca cacgctcacc aactacaaag ccttcagcca gttcatgagg     720
cccctaattg ctaagaagaa tcctaagatc ccaatgtcta agatgatgac catccttggg     780
gccaaatgga gagagttcag tgccaacaac cccttcaagg ggtcagcagc tgctgtggcg     840
gcggcagcgg cagcagcagc agcagctgta gctgagcagg tgtcagctgc tgtctcgtcg     900
gccaccccca tagcaccctc cggacccccc gccttccac cacccctgc tgctgatatc      960 cagcccccac ccatccgaag agccaaaacc aaagagggca aaggtccagg ccataagagg    1020
cggagtaaga gccccgagt gcctgatgga cgcaagaagc ttcggggaaa gaaaatggca    1080
ccactcaaaa taaaactagg gcttctgggt ggcaagagga agaaaggagg ctcgtatgtt    1140
tttcagagcg acgaaggtcc tgaaccagag gctgaggaat cagacctgga cagtggcagt    1200
gtccacagtg cctcaggccg gcctgatggc cctgtccgca ccaagaaact aaagagaggc    1260
cggccaggaa ggaagaagaa gaaggtcctg ggctgtcctg cagtggccgg ggaggaggag    1320
gttgatggct acgagacgga tcaccaggat tactgtgagg tgtgccagca gggtgggaa     1380 attattctgt gtgacacctg ccctcgtgcc taccacctcg tctgccttga tcctgagctt    1440
gaccgggctc cagagggcaa atggagctgc cctcactgtg agaaggaggg ggtccagtgg    1500
gaggccaagg aggaagaaga agaatacgaa gaggagggag aggaagaagg ggagaaggag    1560
gaggaggatg atcacatgga gtactgccgc gtatgcaagg acggcgggga gctcctgtgc    1620
tgtgacgcgt gcatctcctc ctaccacatt cattgtctaa accctcccct gcctgacatt    1680
cccaatggtg aatggctgtg tcccgatgc acatgccccg tgctgaaggg tcgagtgcag    1740
aagatcctac attggcggtg gggggagcca cctgtagcag tgccagcccc tcaacaggca    1800
```

```
gatggaaatc cagatgtccc acccccccgt cctcttcaag gcagatcaga gcgagagttc   1860
tttgtcaagt gggtaggact atcctactgg cactgctcct gggccaagga gcttcagctg   1920
gaaatcttcc atttggttat gtatcgaaac taccagcgga agaatgacat ggatgagccc   1980
ccacccctgg actatggctc cggcgaggat gatgggaaga gcgacaagcg taaagtgaaa   2040
gacccgcact atgctgagat ggaggagaag tactatcgtt ttggcatcaa gccagagtgg   2100
atgaccgtcc accgcatcat caaccacagt gtggataaaa aggggaatta ccactatcta   2160
gtaaaatgga gggacttacc atatgaccag tccacgtggg aggaagatga aatgaatatc   2220
cctgaatacg aagaacataa gcaaagctac tggagacacc gagaactaat tatgggggaa   2280
gaccctgccc agccccgcaa gtataagaag aagaagaagg agctacaggg tgatgggcct   2340
cccagttctc ccactaatga tcctaccgtg aaatatgaga ctcagccacg gtttatcaca   2400
gccactggag gcaccctgca catgtatcag ttggaagggc tgaactggct acgcttctcc   2460
tgggcccagg gcactgacac cattctagct gatgagatgg ggctaggcaa gaccatacaa   2520
accatcgtct cctctactc actctacaag gagggccaca caaaaggtcc cttcctggtg   2580
agtgccccac tctctaccat cattaactgg gagcgggagt tccagatgtg ggcacccaaa   2640
ttctatgtgg tgacatacac gggtgacaag gacagccggg ccatcattcg tgagaatgaa   2700
ttctcctttg aggacaatgc catcaaaggg ggcaagaaag cttttaagat gaaaagggag   2760
gcacaggtga agttccatgt tctcctgaca tcgtatgagc tgatcaccat tgatcaggca   2820
gcacttggtt ccatccgctg ggcctgtctt gtggtagatg aggcccatcg actcaagaac   2880
aaccagtcca gttttttcag ggttctcaat ggttacaaga tagatcataa gttgctgctg   2940
acaggaaccc cattgcagaa taatctggag gagctcttcc atctcctgaa cttcctcacc   3000
ccagagagat taacaacttg gagggcttc ctggaggagt tgctgacat atccaaagag   3060 gaccagatca agaaactgca tgatttgctg gggccacaca tgctgcggag actcaaggca   3120
gatgtcttta agaacatgcc agccaagaca gagctcatcg ttcgggtgga gctaagcccc   3180
atgcagaaga aatactacaa atacatcctg actcgaaatt tgaggccttt gaattcacga   3240
ggtggtggga accaggtgtc gctgcttaat atcatgatgg atcttaagaa gtgctgcaac   3300
catccatacc ttttccccgt ggctgctatg gagtccccca aactcccag tggggcttat   3360 gagggtgggg cacttattaa gtcgtctggg aagctcatgc tgctccagaa gatgctgcga   3420
aagctgaagg agcaaggaca ccgagtgctc atcttctcgc agatgaccaa aatgttagac   3480
ttgcttgagg acttcttaga ctatgaaggc tacaagtatg agcgcatcga tggtggtatc   3540
acgggtgccc tgaggcagga ggccatcgat cggtttaatg ctcctgggc caacaattc   3600 tgcttcctcc tgtccacccg agctggggc ctgggcatca atctggccac tgctgacact   3660
gtcatcatct tgattctga ctggaacccc cataatgaca tccaggcctt tagccgggct   3720
catcggattg ccaggccaa caaagtgatg atttaccggt ttgtgactcg cgcgtcagtg   3780
gaagagcgaa tcacacaagt ggccaagaga aagatgatgc tgacacacct ggttgtgcgg   3840
cctgggctgg gctccaaggc aggctccatg tccaagcagg agcttgacga cattctcaaa   3900
tttggcactg aagagctatt caaggatgaa aacgaggggg agaacaagga ggaggacagc   3960
agtgtgattc attatgacaa tgaggccatc gctcggctgt tggaccggaa ccaggatgca   4020
actgaggaca ctgacgtgca gaacatgaat gagtatctca gctccttcaa ggtggcacag   4080
tacgtcgtgc gggaagaaga caagattgag gaaattgagc gagagatcat caagcaggag   4140
```

-continued

```
gagaatgtgg accctgacta ctgggagaag ctgctgaggc atcactatga gcaacagcag    4200
gaagacctag cccggaatct aggcaagggc aagcgggttc gcaagcaagt taactacaat    4260
gatgctgctc aggaagacca agacaaccag tcagagtact cggtgggttc agaggaggag    4320
gatgaagact tcgatgaacg tcctgaaggg cgtagacagt caaagaggca gctccggaat    4380
gagaaagata agccactgcc tccactgctg gcccgagtcg ggggcaacat tgaggtgctg    4440
ggcttcaaca cccgtcagcg gaaggctttc ctcaatgctg tgatgcgctg ggggatgcca    4500
ccacaggatg ccttcaccac acagtggctg gtgcgggacc tgaggggcaa gactgagaag    4560
gagtttaagg cctatgtgtc tttgttcatg cgccatctgt gtgagcctgg ggcagacggc    4620
tctgaaacct tgccgatggg ggtccctcgg gagggactga gtcgccagca ggtgttgacc    4680
cgcattggag tcatgtctct cgtcaaaaag aaggtgcagg agtttgagca catcaatggg    4740
cgttggtcaa tgccggaact gatgcctgac cccagcgccg attctaagcg ctcctccaga    4800
gcctcctctc ctaccaaaac gtctcccacc actcctgagg cttctgctac caacagtccc    4860
tgcacctcta aacctgctac tccagctcca agtgagaaag agaaggcat aaggacacct    4920 cttgagaagg aggaagctga aaaccaggag gaaaagccag agaagaacag cagaattggg    4980
gagaagatgg agacagaggc tgatgccccc agcccagccc catcacttgg ggagcggctg    5040
gagccaagga agattcctct agaggatgag gtgccagggg tgcctggaga gatggagcct    5100
gaacctgggt accgtgggga cagagagaag tcagaagatg taaaaggtga ccgggagctt    5160
cgaccagggc ctcgagatga gccacggtcc aatgggcgac gagaggaaaa gacagagaag    5220
ccccggttca tgttcaatat cgccgatggt ggcttcacag agcttcacac actgtggcag    5280
aatgaggaac gggcagctat ttcctcgggg aaactcaatg agatctggca cagaagacat    5340
gactattggc ttctggctgg gattgtcctc catggctatg cacggtggca ggacatccag    5400
aatgatgctc aatttgccat tatcaacgag ccatttaaaa ctgaagccaa taaggggaac    5460
tttctggaga tgaaaaataa gttcctggcc cggaggttca agctcctgga gcaggcgctg    5520
gtgattgagg agcagctgcg gcgggcggcc tacctgaacc tgtcgcagga gccggcgcac    5580
cccgccatgg ccctccacgc ccgcttcgcc gaggccgagt gcctggccga gagccaccag    5640
cacctctcca aggagtcgct ggcggggaac aagccggcca acgccgtcct gcacaaggtt    5700
ctgaaccagc tggaggagtt gctgagcgac atgaaggcgg acgtgacccg cctgccagcc    5760
acgctgtccc gaataccccc catcgcagcc cgccttcaga tgtccgagcg cagcatcctc    5820
agccggctgg ccagcaaggg cacggagcct caccccacac cggcctaccc gccgggtccc    5880
tacgctacac ctccggggta cggggcggcc ttcagcgccg cacccgtagg ggccctggcc    5940
gccgcaggcg ccaattacag ccagatgcct gcagggtcct tcatcacagc cgccaccaac    6000
ggcccaattc accgattttt taaaaaagtt ccagaaatcc agtgacgaat gtggtataca    6060
aaaaaatata taaattcttt caacttagaa taattaagtc ataaaataca tagggtacaa    6120
ataccacatt ccgttctaaa atgatatctt aggatcatca aagaaaaag aggatttgga    6180 ttatgcaaaa aatgattcct atatatataa tcaattatct aactgacatt tttgcaaatc    6240
taccacaact tcgccttttta ttgcatatgc taaacaagca gatgctaagt ctgtaaactg    6300
tgaattaacc tcctttttaa ttaattgttc g                                    6331
```

<210> SEQ ID NO 30
<211> LENGTH: 6331
<212> TYPE: DNA
<213> ORGANISM: Homo sapiens <300> PUBLICATION INFORMATION:
<308> DATABASE ACCESSION NUMBER: GenBank/NM_001272
<309> DATABASE ENTRY DATE: 2001-02-03
<313> RELEVANT RESIDUES: (1)..(6331)

<400> SEQUENCE: 30

| | | | | | |
|---|---|---|---|---|---|
| atctttgttt | gggtctccca | tactgcgtat | agatgaatgg | gtcaggatat | ctggaacaaa | 60 |
| atatggaggt | gaagggtgag | atcgggaaac | aaagggtatg | gccccctagt | tcccaaaggg | 120 |
| agcagggaga | tgggaataga | attgaaggta | ggttttaggc | tacttgggag | gaggaatatt | 180 |
| taggtaattg | tggagacttt | ctcctgtgtg | atgaaggcgg | cagacactgt | gatcctgtgg | 240 |
| gcaagaagta | aaaatgacca | gctgaggatt | tcttttcctc | caggactgtg | ttggggtgac | 300 |
| aggatgcctg | ataaggatga | cattcggctg | ctgccgtcag | cattgggtgt | gaagaagaga | 360 |
| aaacgaggac | ccaagaagca | gaaggagaac | aagccaggaa | aaccccgaaa | acgcaagaag | 420 |
| cgtgacagtg | aggaggaatt | tggttctgag | cgagatgagt | accgggagaa | gtcagagagt | 480 |
| gggggcagtg | aatatggaac | cggaccgggt | cggaaacgaa | gaggaagcca | ccgagaaaaa | 540 |
| aaggagaaga | agacaaagcg | gcggaaaaag | gggagggga | atgggggca | aaagcaagtg | 600 |
| gaacagaagt | catcagcaac | tctgcttctg | acctggggcc | tggaggatgt | ggagcatgtg | 660 |
| ttctctgagg | aggattacca | cacgctcacc | aactacaaag | ccttcagcca | gttcatgagg | 720 |
| cccctaattg | ctaagaagaa | tcctaagatc | ccaatgtcta | agatgatgac | catccttggg | 780 |
| gccaaatgga | gagagttcag | tgccaacaac | cccttcaagg | ggtcagcagc | tgctgtggcg | 840 |
| gcggcagcgg | cagcagcagc | agcagctgta | gctgagcagg | tgtcagctgc | tgtctcgtcg | 900 |
| gccaccccca | tagcaccctc | cggacccccc | gccttccac | caccccctgc | tgctgatatc | 960 |
| cagcccccac | ccatccgaag | agccaaaacc | aaagagggca | aagtccagg | ccataagagg | 1020 |
| cggagtaaga | gcccccgagt | gcctgatgga | cgcaagaagc | ttcggggaaa | gaaaatggca | 1080 |
| ccactcaaaa | taaaactagg | gcttctgggt | ggcaagagga | agaaaggagg | ctcgtatgtt | 1140 |
| tttcagagcg | acgaaggtcc | tgaaccagag | gctgaggaat | cagacctgga | cagtggcagt | 1200 |
| gtccacagtg | cctcaggccg | gcctgatggc | cctgtccgca | ccaagaaact | aaagagaggc | 1260 |
| cggccaggaa | ggaagaagaa | gaaggtcctg | ggctgtcctg | cagtggccgg | ggaggaggag | 1320 |
| gttgatggct | acgagacgga | tcaccaggat | tactgtgagg | tgtgccagca | gggtgggga | 1380 |
| attattctgt | gtgacacctg | ccctcgtgcc | taccacctcg | tctgccttga | tcctgagctt | 1440 |
| gaccgggctc | cagagggcaa | atggagctgc | cctcactgtg | agaaggaggg | ggtccagtgg | 1500 |
| gaggccaagg | aggaagaaga | agaatacgaa | gaggagggag | aggaagaagg | ggagaaggag | 1560 |
| gaggaggatg | atcacatgga | gtactgccgc | gtatgcaagg | acggcgggga | gctcctgtgc | 1620 |
| tgtgacgcgt | gcatctcctc | ctaccacatt | cattgtctaa | accctcccct | gcctgacatt | 1680 |
| cccaatggtg | aatggctgtg | tccccgatgc | acatgcccg | tgctgaaggg | tcgagtgcag | 1740 |
| aagatcctac | attggcggtg | gggggagcca | cctgtagcag | tgccagcccc | tcaacaggca | 1800 |
| gatggaaatc | cagatgtccc | acccccccgt | cctcttcaag | gcagatcaga | gcgagagttc | 1860 |
| tttgtcaagt | gggtaggact | atcctactgg | cactgctcct | gggccaagga | gcttcagctg | 1920 |
| gaaatcttcc | atttggttat | gtatcgaaac | taccagcgga | agaatgacat | ggatgagccc | 1980 |
| ccaccccctgg | actatggctc | cggcgaggat | gatgggaaga | gcgacaagcg | taaagtgaaa | 2040 |
| gacccgcact | atgctgagat | ggaggagaag | tactatcgtt | ttggcatcaa | gccagagtgg | 2100 |
| atgaccgtcc | accgcatcat | caaccacagt | gtggataaaa | aggggaatta | ccactatcta | 2160 |

```
gtaaaatgga gggacttacc atatgaccag tccacgtggg aggaagatga aatgaatatc    2220
cctgaatacg aagaacataa gcaaagctac tggagacacc gagaactaat tatgggggaa    2280
gaccctgccc agccccgcaa gtataagaag aagaagaagg agctacaggg tgatgggcct    2340
cccagttctc ccactaatga tcctaccgtg aaatatgaga ctcagccacg gtttatcaca    2400
gccactggag gcaccctgca catgtatcag ttggaagggc tgaactggct acgcttctcc    2460
tgggcccagg gcactgacac cattctagct gatgagatgg ggctaggcaa gaccatacaa    2520
accatcgtct tcctctactc actctacaag gagggccaca caaaaggtcc cttcctggtg    2580
agtgccccac tctctaccat cattaactgg gagcgggagt ccagatgtg  ggcacccaaa    2640 ttctatgtgg tgacatacac gggtgacaag gacagccggg ccatcattcg tgagaatgaa    2700
ttctcctttg aggacaatgc catcaaaggg gcaagaaag  cttttaagat gaaaagggag    2760
gcacaggtga agttccatgt tctcctgaca tcgtatgagc tgatcaccat tgatcaggca    2820
gcacttggtt ccatccgctg gcctgtcctt gtggtagatg aggcccatcg actcaagaac    2880
aaccagtcca agttttttcag ggttctcaat ggttacaaga tagatcataa gttgctgctg    2940
acaggaaccc cattgcagaa taatctggag gagctcttcc atctcctgaa cttcctcacc    3000
ccagagagat ttaacaactt ggagggcttc ctggaggagt ttgctgacat atccaaagag    3060
gaccagatca agaaactgca tgatttgctg gggccacaca tgctgcggag actcaaggca    3120
gatgtcttta agaacatgcc agccaagaca gagctcatcg ttcgggtgga gctaagcccc    3180
atgcagaaga aatactacaa atacatcctg actcgaaatt ttgaggcctt gaattcacga    3240
ggtggtggga ccaggtgtc  gctgcttaat atcatgatgg atcttaagaa gtgctgcaac    3300
catccatacc ttttcccgt  ggctgctatg gagtccccca aactcccag  tggggcttat    3360 gagggtgggg cacttattaa gtcgtctggg aagctcatgc tgctccagaa gatgctgcga    3420
aagctgaagg agcaaggaca ccgagtgctc atcttctcgc agatgaccaa aatgttagac    3480
ttgcttgagg acttcttaga ctatgaaggc tacaagtatg agcgcatcga tggtggtatc    3540
acgggtgccc tgaggcagga ggccatcgat cggtttaatg ctcctggggc ccaacaattc    3600
tgcttcctcc tgtccacccg agctgggggc ctgggcatca atctggccac tgctgacact    3660
gtcatcatct ttgattctga ctggaacccc cataatgaca tccaggcctt tagccgggct    3720
catcggattg ccaggccaa  caaagtgatg atttaccggt ttgtgactcg cgcgtcagtg    3780
gaagagcgaa tcacacaagt ggccaagaga aagatgatgc tgacacacct ggttgtgcgg    3840
cctgggctgg gctccaaggc aggctccatg tccaagcagg agcttgacga cattctcaaa    3900
tttggcactg aagagctatt caaggatgaa aacgaggggg agaacaagga ggaggacagc    3960
agtgtgattc attatgacaa tgaggccatc gctcggctgt tggaccggaa ccaggatgca    4020
actgaggaca ctgacgtgca gaacatgaat gagtatctca gctccttcaa ggtggcacag    4080
tacgtcgtgc gggaagaaga caagattgag gaaattgagc gagagatcat caagcaggag    4140
gagaatgtgg accctgacta ctgggagaag ctgctgaggc atcactatga gcaacagcag    4200
gaagacctag cccggaatct aggcaaggc  aagcgggttc gcaagcaagt taactacaat    4260
gatgctgctc aggaagacca agacaaccag tcagagtact cggtgggttc agaggaggag    4320
gatgaagact cgatgaacg  tcctgaaggg cgtagacagt caaagaggca gctccggaat    4380
gagaaagata agccactgcc tccactgctg gcccgagtcg ggggcaacat tgaggtgctg    4440
ggcttcaaca cccgtcagcg gaaggctttc ctcaatgctg tgatgcgctg ggggatgcca    4500
ccacaggatg ccttcaccac acagtggctg gtgcgggacc tgagggggcaa gactgagaag    4560
```

-continued

```
gagtttaagg cctatgtgtc tttgttcatg cgccatctgt gtgagcctgg ggcagacggc    4620
tctgaaacct tgccgatgg ggtccctcgg gagggactga gtcgccagca ggtgttgacc    4680
cgcattggag tcatgtctct cgtcaaaaag aaggtgcagg agtttgagca catcaatggg    4740
cgttggtcaa tgccggaact gatgcctgac cccagcgccg attctaagcg ctcctccaga    4800
gcctcctctc ctaccaaaac gtctcccacc actcctgagg cttctgctac caacagtccc    4860
tgcacctcta aacctgctac tccagctcca agtgagaaag agaaggcat aaggacacct     4920 cttgagaagg aggaagctga aaaccaggag gaaaagccag agaagaacag cagaattggg    4980
gagaagatgg agacagaggc tgatgcccc agcccagccc catcacttgg ggagcggctg     5040
gagccaagga agattcctct agaggatgag gtgccagggg tgcctggaga gatggagcct    5100
gaacctgggt accgtgggga cagagagaag tcagaagatg taaaaggtga ccgggagctt    5160
cgaccagggc ctcgagatga gccacggtcc aatgggcgac gagaggaaaa gacagagaag    5220
ccccggttca tgttcaatat cgccgatggt ggcttcacag agcttcacac actgtggcag    5280
aatgaggaac gggcagctat ttcctcgggg aaactcaatg agatctggca cagaagacat    5340
gactattggc ttctggctgg gattgtcctc catggctatg cacggtggca ggacatccag    5400
aatgatgctc aatttgccat tatcaacgag ccatttaaaa ctgaagccaa taaggggaac    5460
tttctggaga tgaaaaataa gttcctggcc cggaggttca agctcctgga gcaggcgctg    5520
gtgattgagg agcagctgcg gcgggcggcc tacctgaacc tgtcgcagga gccggcgcac    5580
cccgccatgg ccctccacgc ccgcttcgcc gaggccgagt gcctggccga gagccaccag    5640
cacctctcca aggagtcgct ggcggggaac aagccggcca acgccgtcct gcacaaggtt    5700
ctgaaccagc tggaggagtt gctgagcgac atgaaggcgg acgtgacccg cctgccagcc    5760
acgctgtccc gaataccccc catcgcagcc cgccttcaga tgtccgagcg cagcatcctc    5820
agccggctgg ccagcaaggg cacggagcct cacccacac cggcctaccc gccgggtccc    5880
tacgctacac ctccggggta cggggcggcc ttcagcgccg cacccgtagg ggccctggcc    5940
gccgcaggcg ccaattacag ccagatgcct gcagggtcct tcatcacagc cgccaccaac    6000
ggcccaattc accgattttt taaaaaagtt ccagaaatcc agtgacgaat gtggtataca    6060
aaaaaatata taaattcttt caacttagaa taattaagtc ataaaataca tagggtacaa    6120
ataccacatt ccgttctaaa atgatatctt aggatcatca aagaaaaag aggatttgga     6180 ttatgcaaaa aatgattcct atatatataa tcaattatct aactgacatt tttgcaaatc    6240
taccacaact tcgcctttta ttgcatatgc taaacaagca gatgctaagt ctgtaaactg    6300
tgaattaacc tcctttttaa ttaattgttc g                                   6331
```

<210> SEQ ID NO 31
<211> LENGTH: 560
<212> TYPE: PRT
<213> ORGANISM: Homo sapiens

<400> SEQUENCE: 31

Met Pro Asp Ser Thr Leu Pro Gly Ser Arg Val Leu Ala Arg Leu Asp
1               5                   10                  15

Arg Asp Ser Leu Val His Ser Ser Pro His Val Ala Leu Ser His Val
                20                  25                  30

Asp Ala Arg Ser Tyr His Leu Leu Val Arg Asp Val Ser Lys Glu Asn
            35                  40                  45

Ser Gly Tyr Tyr Tyr Cys His Val Ser Leu Trp Ala Pro Gly His Asn

-continued

```
            50                  55                  60
Arg Ser Trp His Lys Val Ala Glu Ala Val Ser Ser Pro Ala Gly Val
 65                  70                  75                  80

Gly Val Thr Trp Leu Glu Pro Asp Tyr Gln Val Tyr Leu Asn Ala Ser
                 85                  90                  95

Lys Val Pro Gly Phe Ala Asp Pro Thr Glu Leu Ala Cys Arg Val
                100                 105                 110

Val Asp Thr Lys Ser Gly Glu Ala Asn Val Arg Phe Thr Val Ser Trp
                115                 120                 125

Tyr Tyr Arg Met Asn Arg Arg Ser Asp Asn Val Val Thr Ser Glu Leu
130                 135                 140

Leu Ala Val Met Asp Gly Asp Trp Thr Leu Lys Tyr Gly Glu Arg Ser
145                 150                 155                 160

Lys Gln Arg Ala Gln Asp Gly Asp Phe Ile Phe Ser Lys Glu His Thr
                165                 170                 175

Asp Thr Phe Asn Phe Arg Ile Gln Arg Thr Thr Glu Glu Asp Arg Gly
                180                 185                 190

Asn Tyr Tyr Cys Val Val Ser Ala Trp Thr Lys Gln Arg Asn Asn Ser
                195                 200                 205

Trp Val Lys Ser Lys Asp Val Phe Ser Lys Pro Val Asn Ile Phe Trp
                210                 215                 220

Ala Leu Glu Asp Ser Val Leu Val Val Lys Ala Arg Gln Pro Lys Pro
225                 230                 235                 240

Phe Phe Ala Ala Gly Asn Thr Phe Glu Met Thr Cys Lys Val Ser Ser
                245                 250                 255

Lys Asn Ile Lys Ser Pro Arg Tyr Ser Val Leu Ile Met Ala Glu Lys
                260                 265                 270

Pro Val Gly Asp Leu Ser Ser Pro Asn Glu Thr Lys Tyr Ile Ile Ser
                275                 280                 285

Leu Asp Gln Asp Ser Val Val Lys Leu Glu Asn Trp Thr Asp Ala Ser
                290                 295                 300

Arg Val Asp Gly Val Val Leu Glu Lys Val Gln Glu Asp Glu Phe Arg
305                 310                 315                 320

Tyr Arg Met Tyr Gln Thr Gln Val Ser Asp Ala Gly Leu Tyr Arg Cys
                325                 330                 335

Met Val Thr Ala Trp Ser Pro Val Arg Gly Ser Leu Trp Arg Glu Ala
                340                 345                 350

Ala Thr Ser Leu Ser Asn Pro Ile Glu Ile Asp Phe Gln Thr Ser Gly
                355                 360                 365

Pro Ile Phe Asn Ala Ser Val His Ser Asp Thr Pro Ser Val Ile Arg
                370                 375                 380

Gly Asp Leu Ile Lys Leu Phe Cys Ile Ile Thr Val Glu Gly Ala Ala
385                 390                 395                 400

Leu Asp Pro Asp Asp Met Ala Phe Asp Val Ser Trp Phe Ala Val His
                405                 410                 415

Ser Phe Gly Leu Asp Lys Ala Pro Val Leu Leu Ser Ser Leu Asp Arg
                420                 425                 430

Lys Gly Ile Val Thr Thr Ser Arg Arg Asp Trp Lys Ser Asp Leu Ser
                435                 440                 445

Leu Glu Arg Val Ser Val Leu Glu Phe Leu Leu Gln Val His Gly Ser
                450                 455                 460

Glu Asp Gln Asp Phe Gly Asn Tyr Tyr Cys Ser Val Thr Pro Trp Val
465                 470                 475                 480
```

```
Lys Ser Pro Thr Gly Ser Trp Gln Lys Glu Ala Glu Ile His Ser Lys
                485                 490                 495

Pro Val Phe Ile Thr Val Lys Met Asp Val Leu Asn Ala Phe Lys Tyr
            500                 505                 510

Pro Leu Leu Ile Gly Val Gly Leu Ser Thr Val Ile Gly Leu Leu Ser
            515                 520                 525

Cys Leu Ile Gly Tyr Cys Ser Ser His Trp Cys Cys Lys Lys Glu Val
            530                 535                 540

Gln Glu Thr Arg Arg Glu Arg Arg Leu Met Ser Met Glu Met Asp
545                 550                 555                 560

<210> SEQ ID NO 32
<211> LENGTH: 186
<212> TYPE: PRT
<213> ORGANISM: Homo sapiens

<400> SEQUENCE: 32

Val His Ser Asp Thr Pro Ser Val Ile Arg Gly Asp Leu Ile Lys Leu
1               5                   10                  15

Phe Cys Ile Ile Thr Val Glu Gly Ala Ala Leu Asp Pro Asp Asp Met
            20                  25                  30

Ala Phe Asp Val Ser Trp Phe Ala Val His Ser Phe Gly Leu Asp Lys
        35                  40                  45

Ala Pro Val Leu Leu Ser Ser Leu Asp Arg Lys Gly Ile Val Thr Thr
    50                  55                  60

Ser Arg Arg Asp Trp Lys Ser Asp Leu Ser Leu Glu Arg Val Ser Val
65                  70                  75                  80

Leu Glu Phe Leu Leu Gln Val His Gly Ser Glu Asp Gln Asp Phe Gly
                85                  90                  95

Asn Tyr Tyr Cys Ser Val Thr Pro Trp Val Lys Ser Pro Thr Gly Ser
            100                 105                 110

Trp Gln Lys Glu Ala Glu Ile His Ser Lys Pro Val Phe Ile Thr Val
        115                 120                 125

Lys Met Asp Val Leu Asn Ala Phe Lys Tyr Pro Leu Leu Ile Gly Val
    130                 135                 140

Gly Leu Ser Thr Val Ile Gly Leu Leu Ser Cys Leu Ile Gly Tyr Cys
145                 150                 155                 160

Ser Ser His Trp Cys Cys Lys Lys Glu Val Gln Glu Thr Arg Arg Glu
                165                 170                 175

Arg Arg Arg Leu Met Ser Met Glu Met Asp
            180                 185

<210> SEQ ID NO 33
<211> LENGTH: 1944
<212> TYPE: PRT
<213> ORGANISM: Homo sapiens

<400> SEQUENCE: 33

Met Lys Ala Ala Asp Thr Val Ile Leu Trp Ala Arg Ser Lys Asn Asp
1               5                   10                  15

Gln Leu Arg Ile Ser Phe Pro Pro Gly Leu Cys Trp Gly Asp Arg Met
            20                  25                  30

Pro Asp Lys Asp Asp Ile Arg Leu Leu Pro Ser Ala Leu Gly Val Lys
        35                  40                  45

Lys Arg Lys Arg Gly Pro Lys Lys Gln Lys Glu Asn Lys Pro Gly Lys
    50                  55                  60
```

-continued

```
Pro Arg Lys Arg Lys Lys Arg Asp Ser Glu Glu Glu Phe Gly Ser Glu
 65                  70                  75                  80

Arg Asp Glu Tyr Arg Glu Lys Ser Glu Ser Gly Gly Ser Glu Tyr Gly
                 85                  90                  95

Thr Gly Pro Gly Arg Lys Arg Arg Lys His Arg Glu Lys Lys Glu
            100                 105                 110

Lys Lys Thr Lys Arg Arg Lys Lys Gly Glu Gly Asp Gly Gly Gln Lys
            115                 120                 125

Gln Val Glu Gln Lys Ser Ser Ala Thr Leu Leu Leu Thr Trp Gly Leu
130                 135                 140

Glu Asp Val Glu His Val Phe Ser Glu Glu Asp Tyr His Thr Leu Thr
145                 150                 155                 160

Asn Tyr Lys Ala Phe Ser Gln Phe Met Arg Pro Leu Ile Ala Lys Lys
                165                 170                 175

Asn Pro Lys Ile Pro Met Ser Lys Met Met Thr Ile Leu Gly Ala Lys
            180                 185                 190

Trp Arg Glu Phe Ser Ala Asn Asn Pro Phe Lys Gly Ser Ala Ala Ala
        195                 200                 205

Val Ala Ala Ala Ala Ala Ala Ala Ala Val Ala Glu Gln Val
    210                 215                 220

Ser Ala Ala Val Ser Ser Ala Thr Pro Ile Ala Pro Ser Gly Pro Pro
225                 230                 235                 240

Ala Leu Pro Pro Pro Ala Ala Asp Ile Gln Pro Pro Ile Arg
                245                 250                 255

Arg Ala Lys Thr Lys Glu Gly Lys Gly Pro Gly His Lys Arg Arg Ser
            260                 265                 270

Lys Ser Pro Arg Val Pro Asp Gly Arg Lys Lys Leu Arg Gly Lys Lys
        275                 280                 285

Met Ala Pro Leu Lys Ile Lys Leu Gly Leu Leu Gly Gly Lys Arg Lys
    290                 295                 300

Lys Gly Gly Ser Tyr Val Phe Gln Ser Asp Glu Gly Pro Glu Pro Glu
305                 310                 315                 320

Ala Glu Glu Ser Asp Leu Asp Ser Gly Ser Val His Ser Ala Ser Gly
                325                 330                 335

Arg Pro Asp Gly Pro Val Arg Thr Lys Lys Leu Lys Arg Gly Arg Pro
            340                 345                 350

Gly Arg Lys Lys Lys Lys Val Leu Gly Cys Pro Ala Val Ala Gly Glu
        355                 360                 365

Glu Glu Val Asp Gly Tyr Glu Thr Asp His Gln Asp Tyr Cys Glu Val
    370                 375                 380

Cys Gln Gln Gly Gly Glu Ile Ile Leu Cys Asp Thr Cys Pro Arg Ala
385                 390                 395                 400

Tyr His Leu Val Cys Leu Asp Pro Glu Leu Asp Arg Ala Pro Glu Gly
                405                 410                 415

Lys Trp Ser Cys Pro His Cys Glu Lys Glu Gly Val Gln Trp Glu Ala
            420                 425                 430

Lys Glu Glu Glu Glu Glu Tyr Glu Glu Glu Glu Glu Glu Glu Gly Glu
        435                 440                 445

Lys Glu Glu Glu Asp Asp His Met Glu Tyr Cys Arg Val Cys Lys Asp
    450                 455                 460

Gly Gly Glu Leu Leu Cys Cys Asp Ala Cys Ile Ser Ser Tyr His Ile
465                 470                 475                 480
```

```
His Cys Leu Asn Pro Pro Leu Pro Asp Ile Pro Asn Gly Glu Trp Leu
                485                 490                 495

Cys Pro Arg Cys Thr Cys Pro Val Leu Lys Gly Arg Val Gln Lys Ile
            500                 505                 510

Leu His Trp Arg Trp Gly Glu Pro Pro Val Ala Val Pro Ala Pro Gln
        515                 520                 525

Gln Ala Asp Gly Asn Pro Asp Val Pro Pro Arg Pro Leu Gln Gly
    530                 535                 540

Arg Ser Glu Arg Glu Phe Phe Val Lys Trp Val Gly Leu Ser Tyr Trp
545                 550                 555                 560

His Cys Ser Trp Ala Lys Glu Leu Gln Leu Glu Ile Phe His Leu Val
                565                 570                 575

Met Tyr Arg Asn Tyr Gln Arg Lys Asn Asp Met Asp Glu Pro Pro Pro
            580                 585                 590

Leu Asp Tyr Gly Ser Gly Glu Asp Asp Gly Lys Ser Asp Lys Arg Lys
        595                 600                 605

Val Lys Asp Pro His Tyr Ala Glu Met Glu Glu Lys Tyr Tyr Arg Phe
    610                 615                 620

Gly Ile Lys Pro Glu Trp Met Thr Val His Arg Ile Ile Asn His Ser
625                 630                 635                 640

Val Asp Lys Lys Gly Asn Tyr His Tyr Leu Val Lys Trp Arg Asp Leu
                645                 650                 655

Pro Tyr Asp Gln Ser Thr Trp Glu Glu Asp Glu Met Asn Ile Pro Glu
            660                 665                 670

Tyr Glu Glu His Lys Gln Ser Tyr Trp Arg His Arg Glu Leu Ile Met
        675                 680                 685

Gly Glu Asp Pro Ala Gln Pro Arg Lys Tyr Lys Lys Lys Lys Glu
    690                 695                 700

Leu Gln Gly Asp Gly Pro Pro Ser Ser Pro Thr Asn Asp Pro Thr Val
705                 710                 715                 720

Lys Tyr Glu Thr Gln Pro Arg Phe Ile Thr Ala Thr Gly Gly Thr Leu
                725                 730                 735

His Met Tyr Gln Leu Glu Gly Leu Asn Trp Leu Arg Phe Ser Trp Ala
            740                 745                 750

Gln Gly Thr Asp Thr Ile Leu Ala Asp Glu Met Gly Leu Gly Lys Thr
        755                 760                 765

Ile Gln Thr Ile Val Phe Leu Tyr Ser Leu Tyr Lys Glu Gly His Thr
    770                 775                 780

Lys Gly Pro Phe Leu Val Ser Ala Pro Leu Ser Thr Ile Ile Asn Trp
785                 790                 795                 800

Glu Arg Glu Phe Gln Met Trp Ala Pro Lys Phe Tyr Val Val Thr Tyr
                805                 810                 815

Thr Gly Asp Lys Asp Ser Arg Ala Ile Ile Arg Glu Asn Glu Phe Ser
            820                 825                 830

Phe Glu Asp Asn Ala Ile Lys Gly Gly Lys Ala Phe Lys Met Lys
        835                 840                 845

Arg Glu Ala Gln Val Lys Phe His Val Leu Leu Thr Ser Tyr Glu Leu
    850                 855                 860

Ile Thr Ile Asp Gln Ala Ala Leu Gly Ser Ile Arg Trp Ala Cys Leu
865                 870                 875                 880

Val Val Asp Glu Ala His Arg Leu Lys Asn Asn Gln Ser Lys Phe Phe
                885                 890                 895

Arg Val Leu Asn Gly Tyr Lys Ile Asp His Lys Leu Leu Leu Thr Gly
```

-continued

```
              900             905             910
Thr Pro Leu Gln Asn Asn Leu Glu Glu Leu Phe His Leu Leu Asn Phe
            915             920             925

Leu Thr Pro Glu Arg Phe Asn Asn Leu Glu Gly Phe Leu Glu Glu Phe
        930             935             940

Ala Asp Ile Ser Lys Glu Asp Gln Ile Lys Lys Leu His Asp Leu Leu
945             950             955             960

Gly Pro His Met Leu Arg Arg Leu Lys Ala Asp Val Phe Lys Asn Met
            965             970             975

Pro Ala Lys Thr Glu Leu Ile Val Arg Val Glu Leu Ser Pro Met Gln
            980             985             990

Lys Lys Tyr Tyr Lys Tyr Ile Leu Thr Arg Asn Phe Glu Ala Leu Asn
        995             1000            1005

Ser Arg Gly Gly Gly Asn Gln Val Ser Leu Leu Asn Ile Met Met
    1010            1015            1020

Asp Leu Lys Lys Cys Cys Asn His Pro Tyr Leu Phe Pro Val Ala
    1025            1030            1035

Ala Met Glu Ser Pro Lys Leu Pro Ser Gly Ala Tyr Glu Gly Gly
    1040            1045            1050

Ala Leu Ile Lys Ser Ser Gly Lys Leu Met Leu Leu Gln Lys Met
    1055            1060            1065

Leu Arg Lys Leu Lys Glu Gln Gly His Arg Val Leu Ile Phe Ser
    1070            1075            1080

Gln Met Thr Lys Met Leu Asp Leu Leu Glu Asp Phe Leu Asp Tyr
    1085            1090            1095

Glu Gly Tyr Lys Tyr Glu Arg Ile Asp Gly Gly Ile Thr Gly Ala
    1100            1105            1110

Leu Arg Gln Glu Ala Ile Asp Arg Phe Asn Ala Pro Gly Ala Gln
    1115            1120            1125

Gln Phe Cys Phe Leu Leu Ser Thr Arg Ala Gly Gly Leu Gly Ile
    1130            1135            1140

Asn Leu Ala Thr Ala Asp Thr Val Ile Ile Phe Asp Ser Asp Trp
    1145            1150            1155

Asn Pro His Asn Asp Ile Gln Ala Phe Ser Arg Ala His Arg Ile
    1160            1165            1170

Gly Gln Ala Asn Lys Val Met Ile Tyr Arg Phe Val Thr Arg Ala
    1175            1180            1185

Ser Val Glu Glu Arg Ile Thr Gln Val Ala Lys Arg Lys Met Met
    1190            1195            1200

Leu Thr His Leu Val Val Arg Pro Gly Leu Gly Ser Lys Ala Gly
    1205            1210            1215

Ser Met Ser Lys Gln Glu Leu Asp Asp Ile Leu Lys Phe Gly Thr
    1220            1225            1230

Glu Glu Leu Phe Lys Asp Glu Asn Glu Gly Glu Asn Lys Glu Glu
    1235            1240            1245

Asp Ser Ser Val Ile His Tyr Asp Asn Glu Ala Ile Ala Arg Leu
    1250            1255            1260

Leu Asp Arg Asn Gln Asp Ala Thr Glu Asp Thr Asp Val Gln Asn
    1265            1270            1275

Met Asn Glu Tyr Leu Ser Ser Phe Lys Val Ala Gln Tyr Val Val
    1280            1285            1290

Arg Glu Glu Asp Lys Ile Glu Ile Glu Arg Glu Ile Ile Lys
    1295            1300            1305
```

```
Gln Glu Glu Asn Val Asp Pro Asp Tyr Trp Glu Lys Leu Leu Arg
    1310                1315                1320

His His Tyr Glu Gln Gln Glu Asp Leu Ala Arg Asn Leu Gly
    1325                1330                1335

Lys Gly Lys Arg Val Arg Lys Gln Val Asn Tyr Asn Asp Ala Ala
    1340                1345                1350

Gln Glu Asp Gln Asp Asn Gln Ser Glu Tyr Ser Val Gly Ser Glu
    1355                1360                1365

Glu Glu Asp Glu Asp Phe Asp Glu Arg Pro Glu Gly Arg Arg Gln
    1370                1375                1380

Ser Lys Arg Gln Leu Arg Asn Glu Lys Asp Lys Pro Leu Pro Pro
    1385                1390                1395

Leu Leu Ala Arg Val Gly Gly Asn Ile Glu Val Leu Gly Phe Asn
    1400                1405                1410

Thr Arg Gln Arg Lys Ala Phe Leu Asn Ala Val Met Arg Trp Gly
    1415                1420                1425

Met Pro Pro Gln Asp Ala Phe Thr Thr Gln Trp Leu Val Arg Asp
    1430                1435                1440

Leu Arg Gly Lys Thr Glu Lys Glu Phe Lys Ala Tyr Val Ser Leu
    1445                1450                1455

Phe Met Arg His Leu Cys Glu Pro Gly Ala Asp Gly Ser Glu Thr
    1460                1465                1470

Phe Ala Asp Gly Val Pro Arg Glu Gly Leu Ser Arg Gln Gln Val
    1475                1480                1485

Leu Thr Arg Ile Gly Val Met Ser Leu Val Lys Lys Lys Val Gln
    1490                1495                1500

Glu Phe Glu His Ile Asn Gly Arg Trp Ser Met Pro Glu Leu Met
    1505                1510                1515

Pro Asp Pro Ser Ala Asp Ser Lys Arg Ser Ser Arg Ala Ser Ser
    1520                1525                1530

Pro Thr Lys Thr Ser Pro Thr Thr Pro Glu Ala Ser Ala Thr Asn
    1535                1540                1545

Ser Pro Cys Thr Ser Lys Pro Ala Thr Pro Ala Pro Ser Glu Lys
    1550                1555                1560

Gly Glu Gly Ile Arg Thr Pro Leu Glu Lys Glu Glu Ala Glu Asn
    1565                1570                1575

Gln Glu Glu Lys Pro Glu Lys Asn Ser Arg Ile Gly Glu Lys Met
    1580                1585                1590

Glu Thr Glu Ala Asp Ala Pro Ser Pro Ala Pro Ser Leu Gly Glu
    1595                1600                1605

Arg Leu Glu Pro Arg Lys Ile Pro Leu Glu Asp Glu Val Pro Gly
    1610                1615                1620

Val Pro Gly Glu Met Glu Pro Glu Pro Gly Tyr Arg Gly Asp Arg
    1625                1630                1635

Glu Lys Ser Glu Asp Val Lys Gly Asp Arg Glu Leu Arg Pro Gly
    1640                1645                1650

Pro Arg Asp Glu Pro Arg Ser Asn Gly Arg Arg Glu Glu Lys Thr
    1655                1660                1665

Glu Lys Pro Arg Phe Met Phe Asn Ile Ala Asp Gly Gly Phe Thr
    1670                1675                1680

Glu Leu His Thr Leu Trp Gln Asn Glu Glu Arg Ala Ala Ile Ser
    1685                1690                1695
```

```
Ser Gly Lys Leu Asn Glu Ile Trp His Arg Arg His Asp Tyr Trp
1700                1705                1710

Leu Leu Ala Gly Ile Val Leu His Gly Tyr Ala Arg Trp Gln Asp
    1715                1720                1725

Ile Gln Asn Asp Ala Gln Phe Ala Ile Ile Asn Glu Pro Phe Lys
1730                1735                1740

Thr Glu Ala Asn Lys Gly Asn Phe Leu Glu Met Lys Asn Lys Phe
    1745                1750                1755

Leu Ala Arg Arg Phe Lys Leu Leu Glu Gln Ala Leu Val Ile Glu
1760                1765                1770

Glu Gln Leu Arg Arg Ala Ala Tyr Leu Asn Leu Ser Gln Glu Pro
    1775                1780                1785

Ala His Pro Ala Met Ala Leu His Ala Arg Phe Ala Glu Ala Glu
1790                1795                1800

Cys Leu Ala Glu Ser His Gln His Leu Ser Lys Glu Ser Leu Ala
    1805                1810                1815

Gly Asn Lys Pro Ala Asn Ala Val Leu His Lys Val Leu Asn Gln
1820                1825                1830

Leu Glu Glu Leu Leu Ser Asp Met Lys Ala Asp Val Thr Arg Leu
    1835                1840                1845

Pro Ala Thr Leu Ser Arg Ile Pro Pro Ile Ala Ala Arg Leu Gln
1850                1855                1860

Met Ser Glu Arg Ser Ile Leu Ser Arg Leu Ala Ser Lys Gly Thr
    1865                1870                1875

Glu Pro His Pro Thr Pro Ala Tyr Pro Pro Gly Pro Tyr Ala Thr
1880                1885                1890

Pro Pro Gly Tyr Gly Ala Ala Phe Ser Ala Ala Pro Val Gly Ala
    1895                1900                1905

Leu Ala Ala Gly Ala Asn Tyr Ser Gln Met Pro Ala Gly Ser
1910                1915                1920

Phe Ile Thr Ala Ala Thr Asn Gly Pro Ile His Arg Phe Phe Lys
1925                1930                1935

Lys Val Pro Glu Ile Gln
    1940

<210> SEQ ID NO 34
<211> LENGTH: 1944
<212> TYPE: PRT
<213> ORGANISM: Homo sapiens

<400> SEQUENCE: 34

Met Lys Ala Ala Asp Thr Val Ile Leu Trp Ala Arg Ser Lys Asn Asp
1               5                   10                  15

Gln Leu Arg Ile Ser Phe Pro Pro Gly Leu Cys Trp Gly Asp Arg Met
            20                  25                  30

Pro Asp Lys Asp Asp Ile Arg Leu Leu Pro Ser Ala Leu Gly Val Lys
        35                  40                  45

Lys Arg Lys Arg Gly Pro Lys Lys Gln Lys Glu Asn Lys Pro Gly Lys
    50                  55                  60

Pro Arg Lys Arg Lys Lys Arg Asp Ser Glu Glu Phe Gly Ser Glu
65                  70                  75                  80

Arg Asp Glu Tyr Arg Glu Lys Ser Glu Ser Gly Ser Glu Tyr Gly
            85                  90                  95

Thr Gly Pro Gly Arg Lys Arg Arg Arg Lys His Arg Glu Lys Lys Glu
            100                 105                 110
```

-continued

```
Lys Lys Thr Lys Arg Arg Lys Lys Gly Glu Gly Asp Gly Gly Gln Lys
        115                 120                 125
Gln Val Glu Gln Lys Ser Ser Ala Thr Leu Leu Thr Trp Gly Leu
    130                 135                 140
Glu Asp Val Glu His Val Phe Ser Glu Glu Asp Tyr His Thr Leu Thr
145                 150                 155                 160
Asn Tyr Lys Ala Phe Ser Gln Phe Met Arg Pro Leu Ile Ala Lys Lys
                165                 170                 175
Asn Pro Lys Ile Pro Met Ser Lys Met Met Thr Ile Leu Gly Ala Lys
                180                 185                 190
Trp Arg Glu Phe Ser Ala Asn Asn Pro Phe Lys Gly Ser Ala Ala Ala
            195                 200                 205
Val Ala Ala Ala Ala Ala Ala Ala Ala Val Ala Glu Gln Val
        210                 215                 220
Ser Ala Ala Val Ser Ser Ala Thr Pro Ile Ala Pro Ser Gly Pro Pro
225                 230                 235                 240
Ala Leu Pro Pro Pro Ala Ala Asp Ile Gln Pro Pro Ile Arg
                245                 250                 255
Arg Ala Lys Thr Lys Glu Gly Lys Gly Pro Gly His Lys Arg Arg Ser
                260                 265                 270
Lys Ser Pro Arg Val Pro Asp Gly Arg Lys Leu Arg Gly Lys Lys
            275                 280                 285
Met Ala Pro Leu Lys Ile Lys Leu Gly Leu Leu Gly Lys Arg Lys
        290                 295                 300
Lys Gly Gly Ser Tyr Val Phe Gln Ser Asp Glu Gly Pro Glu Pro Glu
305                 310                 315                 320
Ala Glu Glu Ser Asp Leu Asp Ser Gly Ser Val His Ser Ala Ser Gly
                325                 330                 335
Arg Pro Asp Gly Pro Val Arg Thr Lys Lys Leu Lys Arg Gly Arg Pro
                340                 345                 350
Gly Arg Lys Lys Lys Lys Val Leu Gly Cys Pro Ala Val Ala Gly Glu
            355                 360                 365
Glu Glu Val Asp Gly Tyr Glu Thr Asp His Gln Asp Tyr Cys Glu Val
370                 375                 380
Cys Gln Gln Gly Gly Glu Ile Ile Leu Cys Asp Thr Cys Pro Arg Ala
385                 390                 395                 400
Tyr His Leu Val Cys Leu Asp Pro Glu Leu Asp Arg Ala Pro Glu Gly
                405                 410                 415
Lys Trp Ser Cys Pro His Cys Glu Lys Glu Gly Val Gln Trp Glu Ala
                420                 425                 430
Lys Glu Glu Glu Glu Tyr Glu Glu Gly Glu Glu Gly Glu
            435                 440                 445
Lys Glu Glu Glu Asp Asp His Met Glu Tyr Cys Arg Val Cys Lys Asp
            450                 455                 460
Gly Gly Glu Leu Leu Cys Cys Asp Ala Cys Ile Ser Ser Tyr His Ile
465                 470                 475                 480
His Cys Leu Asn Pro Pro Leu Pro Asp Ile Pro Asn Gly Glu Trp Leu
                485                 490                 495
Cys Pro Arg Cys Thr Cys Pro Val Leu Lys Gly Arg Val Gln Lys Ile
            500                 505                 510
Leu His Trp Arg Trp Gly Glu Pro Pro Val Ala Val Pro Ala Pro Gln
        515                 520                 525
```

-continued

```
Gln Ala Asp Gly Asn Pro Asp Val Pro Pro Arg Pro Leu Gln Gly
    530                 535                 540
Arg Ser Glu Arg Glu Phe Val Lys Trp Val Gly Leu Ser Tyr Trp
545                 550                 555                 560
His Cys Ser Trp Ala Lys Glu Leu Gln Leu Glu Ile Phe His Leu Val
                565                 570                 575
Met Tyr Arg Asn Tyr Gln Arg Lys Asn Asp Met Asp Glu Pro Pro Pro
            580                 585                 590
Leu Asp Tyr Gly Ser Gly Glu Asp Gly Lys Ser Asp Lys Arg Lys
            595                 600                 605
Val Lys Asp Pro His Tyr Ala Glu Met Glu Glu Lys Tyr Tyr Arg Phe
    610                 615                 620
Gly Ile Lys Pro Glu Trp Met Thr Val His Arg Ile Ile Asn His Ser
625                 630                 635                 640
Val Asp Lys Lys Gly Asn Tyr His Tyr Leu Val Lys Trp Arg Asp Leu
                645                 650                 655
Pro Tyr Asp Gln Ser Thr Trp Glu Glu Asp Glu Met Asn Ile Pro Glu
            660                 665                 670
Tyr Glu Glu His Lys Gln Ser Tyr Trp Arg His Arg Glu Leu Ile Met
            675                 680                 685
Gly Glu Asp Pro Ala Gln Pro Arg Lys Tyr Lys Lys Lys Lys Glu
    690                 695                 700
Leu Gln Gly Asp Gly Pro Ser Ser Pro Thr Asn Asp Pro Thr Val
705                 710                 715                 720
Lys Tyr Glu Thr Gln Pro Arg Phe Ile Thr Ala Thr Gly Gly Thr Leu
                725                 730                 735
His Met Tyr Gln Leu Glu Gly Leu Asn Trp Leu Arg Phe Ser Trp Ala
            740                 745                 750
Gln Gly Thr Asp Thr Ile Leu Ala Asp Glu Met Gly Leu Gly Lys Thr
            755                 760                 765
Ile Gln Thr Ile Val Phe Leu Tyr Ser Leu Tyr Lys Glu Gly His Thr
    770                 775                 780
Lys Gly Pro Phe Leu Val Ser Ala Pro Leu Ser Thr Ile Ile Asn Trp
785                 790                 795                 800
Glu Arg Glu Phe Gln Met Trp Ala Pro Lys Phe Tyr Val Val Thr Tyr
                805                 810                 815
Thr Gly Asp Lys Asp Ser Arg Ala Ile Ile Arg Glu Asn Glu Phe Ser
            820                 825                 830
Phe Glu Asp Asn Ala Ile Lys Gly Gly Lys Lys Ala Phe Lys Met Lys
            835                 840                 845
Arg Glu Ala Gln Val Lys Phe His Val Leu Leu Thr Ser Tyr Glu Leu
    850                 855                 860
Ile Thr Ile Asp Gln Ala Ala Leu Gly Ser Ile Arg Trp Ala Cys Leu
865                 870                 875                 880
Val Val Asp Glu Ala His Arg Leu Lys Asn Asn Gln Ser Lys Phe Phe
                885                 890                 895
Arg Val Leu Asn Gly Tyr Lys Ile Asp His Lys Leu Leu Leu Thr Gly
            900                 905                 910
Thr Pro Leu Gln Asn Asn Leu Glu Glu Leu Phe His Leu Leu Asn Phe
            915                 920                 925
Leu Thr Pro Glu Arg Phe Asn Asn Leu Glu Gly Phe Leu Glu Glu Phe
    930                 935                 940
Ala Asp Ile Ser Lys Glu Asp Gln Ile Lys Lys Leu His Asp Leu Leu
```

-continued

```
            945                 950                 955                 960
Gly Pro His Met Leu Arg Arg Leu Lys Ala Asp Val Phe Lys Asn Met
                    965                 970                 975
Pro Ala Lys Thr Glu Leu Ile Val Arg Val Glu Leu Ser Pro Met Gln
                    980                 985                 990
Lys Lys Tyr Tyr Lys Tyr Ile Leu Thr Arg Asn Phe Glu Ala Leu Asn
                    995                 1000                1005
Ser Arg Gly Gly Gly Asn Gln Val Ser Leu Leu Asn Ile Met Met
    1010                1015                1020
Asp Leu Lys Lys Cys Cys Asn His Pro Tyr Leu Phe Pro Val Ala
    1025                1030                1035
Ala Met Glu Ser Pro Lys Leu Pro Ser Gly Ala Tyr Glu Gly Gly
    1040                1045                1050
Ala Leu Ile Lys Ser Ser Gly Lys Leu Met Leu Leu Gln Lys Met
    1055                1060                1065
Leu Arg Lys Leu Lys Glu Gln Gly His Arg Val Leu Ile Phe Ser
    1070                1075                1080
Gln Met Thr Lys Met Leu Asp Leu Leu Glu Asp Phe Leu Asp Tyr
    1085                1090                1095
Glu Gly Tyr Lys Tyr Glu Arg Ile Asp Gly Gly Ile Thr Gly Ala
    1100                1105                1110
Leu Arg Gln Glu Ala Ile Asp Arg Phe Asn Ala Pro Gly Ala Gln
    1115                1120                1125
Gln Phe Cys Phe Leu Leu Ser Thr Arg Ala Gly Gly Leu Gly Ile
    1130                1135                1140
Asn Leu Ala Thr Ala Asp Thr Val Ile Ile Phe Asp Ser Asp Trp
    1145                1150                1155
Asn Pro His Asn Asp Ile Gln Ala Phe Ser Arg Ala His Arg Ile
    1160                1165                1170
Gly Gln Ala Asn Lys Val Met Ile Tyr Arg Phe Val Thr Arg Ala
    1175                1180                1185
Ser Val Glu Glu Arg Ile Thr Gln Val Ala Lys Arg Lys Met Met
    1190                1195                1200
Leu Thr His Leu Val Val Arg Pro Gly Leu Gly Ser Lys Ala Gly
    1205                1210                1215
Ser Met Ser Lys Gln Glu Leu Asp Asp Ile Leu Lys Phe Gly Thr
    1220                1225                1230
Glu Glu Leu Phe Lys Asp Glu Asn Glu Gly Glu Asn Lys Glu Glu
    1235                1240                1245
Asp Ser Ser Val Ile His Tyr Asp Asn Glu Ala Ile Ala Arg Leu
    1250                1255                1260
Leu Asp Arg Asn Gln Asp Ala Thr Glu Asp Thr Asp Val Gln Asn
    1265                1270                1275
Met Asn Glu Tyr Leu Ser Ser Phe Lys Val Ala Gln Tyr Val Val
    1280                1285                1290
Arg Glu Glu Asp Lys Ile Glu Glu Ile Glu Arg Glu Ile Ile Lys
    1295                1300                1305
Gln Glu Glu Asn Val Asp Pro Asp Tyr Trp Glu Lys Leu Leu Arg
    1310                1315                1320
His His Tyr Glu Gln Gln Gln Glu Asp Leu Ala Arg Asn Leu Gly
    1325                1330                1335
Lys Gly Lys Arg Val Arg Lys Gln Val Asn Tyr Asn Asp Ala Ala
    1340                1345                1350
```

-continued

```
Gln Glu Asp Gln Asp Asn Gln Ser Glu Tyr Ser Val Gly Ser Glu
    1355                1360                1365
Glu Glu Asp Glu Asp Phe Asp Glu Arg Pro Glu Gly Arg Arg Gln
    1370                1375                1380
Ser Lys Arg Gln Leu Arg Asn Glu Lys Asp Lys Pro Leu Pro Pro
    1385                1390                1395
Leu Leu Ala Arg Val Gly Gly Asn Ile Glu Val Leu Gly Phe Asn
    1400                1405                1410
Thr Arg Gln Arg Lys Ala Phe Leu Asn Ala Val Met Arg Trp Gly
    1415                1420                1425
Met Pro Pro Gln Asp Ala Phe Thr Thr Gln Trp Leu Val Arg Asp
    1430                1435                1440
Leu Arg Gly Lys Thr Glu Lys Glu Phe Lys Ala Tyr Val Ser Leu
    1445                1450                1455
Phe Met Arg His Leu Cys Glu Pro Gly Ala Asp Gly Ser Glu Thr
    1460                1465                1470
Phe Ala Asp Gly Val Pro Arg Glu Gly Leu Ser Arg Gln Gln Val
    1475                1480                1485
Leu Thr Arg Ile Gly Val Met Ser Leu Val Lys Lys Lys Val Gln
    1490                1495                1500
Glu Phe Glu His Ile Asn Gly Arg Trp Ser Met Pro Glu Leu Met
    1505                1510                1515
Pro Asp Pro Ser Ala Asp Ser Lys Arg Ser Ser Arg Ala Ser Ser
    1520                1525                1530
Pro Thr Lys Thr Ser Pro Thr Thr Pro Glu Ala Ser Ala Thr Asn
    1535                1540                1545
Ser Pro Cys Thr Ser Lys Pro Ala Thr Pro Ala Pro Ser Glu Lys
    1550                1555                1560
Gly Glu Gly Ile Arg Thr Pro Leu Glu Lys Glu Glu Ala Glu Asn
    1565                1570                1575
Gln Glu Glu Lys Pro Glu Lys Asn Ser Arg Ile Gly Glu Lys Met
    1580                1585                1590
Glu Thr Glu Ala Asp Ala Pro Ser Pro Ala Pro Ser Leu Gly Glu
    1595                1600                1605
Arg Leu Glu Pro Arg Lys Ile Pro Leu Glu Asp Glu Val Pro Gly
    1610                1615                1620
Val Pro Gly Glu Met Glu Pro Glu Pro Gly Tyr Arg Gly Asp Arg
    1625                1630                1635
Glu Lys Ser Glu Asp Val Lys Gly Asp Arg Glu Leu Arg Pro Gly
    1640                1645                1650
Pro Arg Asp Glu Pro Arg Ser Asn Gly Arg Arg Glu Glu Lys Thr
    1655                1660                1665
Glu Lys Pro Arg Phe Met Phe Asn Ile Ala Asp Gly Gly Phe Thr
    1670                1675                1680
Glu Leu His Thr Leu Trp Gln Asn Glu Glu Arg Ala Ala Ile Ser
    1685                1690                1695
Ser Gly Lys Leu Asn Glu Ile Trp His Arg Arg His Asp Tyr Trp
    1700                1705                1710
Leu Leu Ala Gly Ile Val Leu His Gly Tyr Ala Arg Trp Gln Asp
    1715                1720                1725
Ile Gln Asn Asp Ala Gln Phe Ala Ile Ile Asn Glu Pro Phe Lys
    1730                1735                1740
```

-continued

```
Thr Glu Ala Asn Lys Gly Asn Phe Leu Glu Met Lys Asn Lys Phe
    1745            1750            1755

Leu Ala Arg Arg Phe Lys Leu Leu Glu Gln Ala Leu Val Ile Glu
    1760            1765            1770

Glu Gln Leu Arg Arg Ala Ala Tyr Leu Asn Leu Ser Gln Glu Pro
    1775            1780            1785

Ala His Pro Ala Met Ala Leu His Ala Arg Phe Ala Glu Ala Glu
    1790            1795            1800

Cys Leu Ala Glu Ser His Gln His Leu Ser Lys Glu Ser Leu Ala
    1805            1810            1815

Gly Asn Lys Pro Ala Asn Ala Val Leu His Lys Val Leu Asn Gln
    1820            1825            1830

Leu Glu Glu Leu Leu Ser Asp Met Lys Ala Asp Val Thr Arg Leu
    1835            1840            1845

Pro Ala Thr Leu Ser Arg Ile Pro Pro Ile Ala Ala Arg Leu Gln
    1850            1855            1860

Met Ser Glu Arg Ser Ile Leu Ser Arg Leu Ala Ser Lys Gly Thr
    1865            1870            1875

Glu Pro His Pro Thr Pro Ala Tyr Pro Pro Gly Pro Tyr Ala Thr
    1880            1885            1890

Pro Pro Gly Tyr Gly Ala Ala Phe Ser Ala Ala Pro Val Gly Ala
    1895            1900            1905

Leu Ala Ala Ala Gly Ala Asn Tyr Ser Gln Met Pro Ala Gly Ser
    1910            1915            1920

Phe Ile Thr Ala Ala Thr Asn Gly Pro Ile His Arg Phe Phe Lys
    1925            1930            1935

Lys Val Pro Glu Ile Gln
    1940
```

COMPOSITION COMPRISING AN ANGIOGENESIS RELATED PROTEIN

RELATED APPLICATION

This is a continuation of International Application No. PCT/FR03/00912, with an international filing date of Mar. 21, 2003 (WO 03/080105, published Oct. 2, 2003), which is based on French Patent Application No. 02/03655, filed Mar. 22, 2002.

TECHNICAL FIELD

The disclosure pertains to the treatment, of angiogenic disorders, in particular to pharmaceutical compositions that are useful for the treatment of pathologies resulting from a deregulation of the angiogenesis mechanism.

BACKGROUND

Angiogenesis is a fundamental process by means of which new blood vessels are formed. This process is essential in many normal physiological phenomena such as reproduction, development and cicatrization. Angiogenesis is under strict control in these normal biological phenomena; i.e., it is triggered during a brief period of several days and then completely inhibited. However, many pathologies are linked to invasive, uncontrolled angiogenesis. Arthritis, for example, is a pathology caused by damage caused to cartilage by invasive neovessels. In diabetic retinopathy, the invasion of the retina by neovessels results in the patients going blind; neovascularization of the ocular apparatus is the major cause of blindness and this neovascularization dominates at least twenty diseases of the eye. Lastly, the growth and metastasis of many tumors are directly dependent on angiogenesis. The tumor stimulates the growth of the neovessels for its own use. Furthermore, these neovessels present escape routes by means of which the tumors can reach the blood circulatory system and cause metastases in remote sites such as the liver, lungs or bones.

Angiogenesis can present an important therapeutic basis in other pathologies such as cardiovascular diseases, diseases of the peripheral arteries and vascular or cerebral lesions. In fact, the promotion of angiogenesis in damaged areas can lead to the formation of lateral blood neovessels as alternatives to the damaged vessels, thereby providing the damaged area with oxygen and other nutritive and biological factors necessary for the survival of the tissues in question.

The formation of neovessels by endothelial cells involves the migration, growth and differentiation of endothelial cells. Regulation of these biological phenomena is directly linked to genetic expression. An increasing number of studies have shown that the regulation of angiogenesis is implemented via an equilibrium among the factors acting directly on the endothelial cells. These factors can be stimulatory on the one hand, such as (among others) VEGF, FGFs, IL-8, HGF/SF and PDGF. The factors can also be inhibitory, such as (among others) IL-10, IL-12, gro-α and gro-β, platelet factor 4, angiostatin, the human chondrocyte derivative inhibitor, thrombospondin and the leukemia inhibitor. (Jensen, 1998 Surg. Neural., 49, 189-195; Tamatani et al., 1999, Carcinogenesis, 20, 957-962; Tanaka et al., 1998, Cancer Res., 58, 3362-3369; Ghe et al., 1997, Cancer Res., 57, 3733-3740; Kawahara et al., 1998, Hepatology, 28, 1512-1517; Chandhuni et al., 1997, Cancer Res., 57, 1814-1819; Jendraschak and Sage, 1996, Semin. Cancer Biol., 7, 139-146; Majewski et al., 1996, J. Invest. Dermatol., 106, 1114-1119.)

The regulation of angiogenesis as described at present is implemented via an equilibrium of two types of factors:
  the angiogenic factors (extracellular polypeptides, primarily mitogenic) acting directly on endothelial cells inducing angiogenesis; and
  the angiostatic factors (extracellular polypeptides, also mostly mitogenic and acting on mitogenesis), also acting directly on endothelial cells so as to inhibit angiogenesis.

The equilibrium between these two types of extracellular factors regulates angiogenesis. It should be noted at this stage that the control of angiogenesis is implemented via the production of angiogenic and angiostatic factors. For example, it has already been shown that the stimulation of the endothelial cell by an angiogenic factor induces the expression of 1) urokinase plasminogen activator (uPA) and its inhibitor PAI-I (Pepper et al., 1990, J. Cell Biol. 111(2), 743-44; Pepper et al., 1996, Enzyme Protein, 49 (1-3), 138-62); 2) matrix metalloproteinases (MMPs) and physiological inhibitors of the activity of these MMPs (TIMPs) (Cornelius et al., 1995, J. Invest. Dermatol., 105(2), 170-6; Jackson and Nguyen, 1997, Int. J. Biochem. Cell Biol., 29(10), 1167-77); 3) inhibitors such as angiopoietin-2 (Ang-2) or thrombospondin-1 (TSP-1) (Mandriota and Pepper, 1998, Circ. Res. 83, 852-859; Oh et al., 1999, J. Biol. Chem. 274(22), 15732-9; Suzuma et al., 1999, American Journal of Pathology, 154, 343-354.) It thus appears that an endothelial cell in the angiogenic state normally produces not only angiogenic factors but also produces angiostatic factors as well. The production of these angiostatic factors enables control of angiogenesis.

Parallel to this operation, endothelial cells stimulated by an angiostatic factor produce not only angiostatic factors, but also produce angiogenic factors for controlling the angiostatic state. This phenomenon has already been described for other types of cells that produce factors implicated in angiogenesis when they are stimulated by an angiostatic factor such as interferon-gamma (Kobayashi et al., 1995, Immunopharmacology, 31(1), 93-101; Arkins et al., 1995, Mol. Endocrinol., 9(3), 350-60; Kodelja et al., 1997, Immunobiology, 197(5), 478-93).

Angiopartnerine is homologous with the negative regulator of the prostaglandin F2 receptor (PTGFRN), (access no. XM_040709, nucleic sequence: 5975 bp, protein sequence: 560 aa), with the protein 6 associated with the human smooth muscle cell (SMAP6) (accession no. AB014734, nucleic sequence: 2197 bp, partial protein sequence: 186 aa), identified by the numbers SEQ ID No. 27 and SEQ ID No. 28 respectively in the attached sequence listing, itself being similar to the regulatory protein of the prostaglandin F2 alpha (FPRP) also designated CD9P-1 and renamed EWI-F by Stipp et al. (2001, J. Biol. Chem., 276, 44, 40545-40554). The sequence GS-N1 comprises the sequences SEQ ID No. 27 and SEQ ID No. 28, presenting 99% of homology with them.

FPRP is a type 1 transmembrane glycoprotein containing 6 extracellular immunoglobulin domains. It was originally identified and characterized by its capacity to combine with prostaglandin F2 alpha and inhibit the binding of this prostaglandin with its receptor. It can also combine with other receptors that are coupled to G protein and contain 7 transmembrane domains, and reduce the ligand-receptor interaction (Orlicky and Nordeen, 1996, Prostaglandins Leukot. Essent. Fatty Acids, 55: 261-268; Orlicky et al., 1998, J. Lip. Res., Vol. 39, 1152-1161). The augmentation of the expression of FPLP has already been associated with cell differentiation, notably that of adipocytes (Orlicky et al., 1998, J. Lip. Res., Vol. 39, 1152-1161). Different studies have shown that CD9P-1 or FPLP is a major partner of two member of the tetraspanin family (also called TM4SF), CD9 and CD81 in protein complexes, combining specifically either with CD81 or with CD9 and CD81 (Charrin S. et al., 2001, J. Biol. Chem.; Stipp et al. (2001, J. Biol. Chem., 276, 7, 4854-4862). The tetraspanins have been implicated in many cellular functions such as adhesion, migration, co-stimulation, transduction of the signal and differentiation, the various functions attributed to the tetraspanins can be linked to their specific combination with the specific partner molecules (Le Naour et al., 2000, Science, 287, 319-321).

The protein CD9 has a broad tissue distribution; it has notably been found in various types of tumors (Si and Hersey, 1993, Int. J. Cancer, 54: 37-43; Miyake et al., 1996, Cancer Res., 56: 1244-1249) as well as in the vessels formed by endothelial cells (Zola et al., 1989, Immunol. Cell Biol.; 67: 63-70). This protein has been implicated in functions such as transduction of the signal, cell adhesion, motility, tumor progression (Ozaki et al., 1995, J. Biol. Chem., 270: 15119-15124; Forsyth, 1991, Immunology, 72: 292-296; Anton et al., 1995, J. Neurosci., 15: 584-595; Shaw et al., 1995, J. Biol. Chem., 270: 24092-24099; Ikeyama et al., 1993, J. Exp. Med., 177: 1231-1237) and notably the adhesion and migration of endothelial cells during angiogenesis (Klein-Soyer et al., 2000, Arterioscler. Thromb. Vasc. Biol., 20: 360-9). The overexpression of CD9 in adenocarcinoma cells suppresses their motility and metastatic potential (Ikeyama et al., 1993, J. Exp. Med., 177: 1231-1237); its expression is inversely correlated with the primary tumors and the appearance of metastases in melanomas, lung cancer, colon cancer and breast cancer (Si and Hersey, 1993, Int. J. Cancer, 54, 37-43; Miyake et al., 1995, Cancer Res., 55: 4127-4131; Adachi et al., 1998, J. Clin. Oncol., 15, 1397-1406; Mori et al., 1998, Clin. Cancer Res., 4, 1507-1510).

The protein CD9P-1 (or FPLP) was identified as being the major partner molecule of CD9 in cancer lines (Serru et al., 1999, Biochem. J., 340, 103-111).

It has also been reported that the protein CD81 is implicated in various functions such as cell signalization and activation of the B lymphocytes (Fearon and Carter, 1995), regulation of the proliferation of the T lymphocytes (Miyazaki et al., 1997, EMBO J., 16, 4217-4225); it could also play a role in cancer because CD81 is a possible receptor for hepatitis C virus, a major cause of hepatic carcinoma (Pileri et al., 1998, Science, 282, 938-941).

Although the exact role of CD9P-1 or FPRP has yet to be defined, its association with CD9 or CD81 can suggest a role in the regulation functions of the CD9 or CD81 receptors. However, no role in the regulation of angiogenesis has been reported to date for the protein called angiopartnerine, identified by the number SEQ ID No. 6 in attached sequence listing, nor for the proteins PTGFRN, CD9P-1/FPRP.

The protein NKX3.1 is a member of the NK class of Homeobox proteins, closely linked to the protein NK-3 of *Drosophila* (Kim, Y. and Nirenberg, 1989, Proc. Natl. Acad. Sci. USA, 86, 7716-7720; He et al., 1997, Genomics, 43, 69-77). Studies on the mouse showed the expression of the gene NKX3.1 in the fetus and embryo in development in a variety of tissue types such as the mesoderm, vascular smooth muscle, epithelium and regions of the central nervous system (Kos et al., 1998, Mech. Dev., 70, 25-34; Tanaka et al., 1999, Mech. Dev., 85, 179-182; Bhatia-Gaur et al., 1999, Genes Dev., 13, 966-977). In the adult, the protein NKX3.1 is localized predominantly in the prostate, more particularly in the epithelial cells, and its expression is regulated by the androgens (He et al., 1997, Genomics, 43, 69-77; Prescott et al., 1998, Prostate, 35, 71-80; Sciavolino et al., 1997, Dev. Dyn., 209, 127-138; Ornstein et al., 2001, J. Urol., 165(4): 1329-34). It appears to play an essential role in the function of the prostate and regulates the proliferation of the epithelial cells of the prostate; the gene NKX3.1 was proposed to be a suppressor gene of the specific tumors of the prostate (Bhatia-Gaur et al., 1999, Genes Dev., 13(8): 966-966). The loss of expression of NKX3.1 in the human cancers of the prostate was recently correlated with the progression of tumors (Bowen et al., 2000, Cancer Res., 60(21): 6111-5). Moreover, it has already been reported that the homeobox proteins are implicated in the regulation of angiogenesis (review: Gorski and Walsh, 2000, Circulation Research, 87: 865-872).

However, no role for the homeobox protein NKX3.1 has been reported to date in the regulation of angiogenesis.

The protein hZFH (human zinc-finger helicase) belongs to the family of Snf2 type helicases known to act as transcriptional regulators for multiple genes (Aubry et al., 1998, Eur. J. Biochem., 243(3): 558-64). It also contains a chromodomain and is homologous with the protein CHD3 ("chromodomain helicase DNA binding protein 3") identified by the sequence SEQ ID No. 29 and SEQ ID No. 30 in the attached sequence listing. It has been reported that the CHD3 proteins could regulate the expression of genes by repressing transcription via an alteration of the structure of chromatin (Zhang et al., 1998, Cell, 95, 279-289; Kehle et al., 1998, Science, 282, 1898-1900). No role has been reported to date in the regulation of the expression of the genes implicated in angiogenesis either for the protein hZFH or for the protein CHD3.

Factor 3 of initiation of eukaryote translation (EIF3), the largest initiation factor of protein synthesis, with a size of 650 kDa, is composed of at least nine peptide subunits (Hershey et al., 1996, Biochimie, 78, 903-907), including subunit 8 (p110) (Asano et al., 1997, J. Biol. Chem., 272, 1101-1109). EIF3 plays a central role in the initiation process of protein biosynthesis notably in the binding of the initiator methionyl-tRNA and mRNA to the ribosome subunit 40S so as to form the initiation complex 40S (Merrick and Hershey, 1996, The pathway and mechanisms of eukaryotic protein synthesis. In: Hershey J W B, Mathews M B, Sonenberg N, eds. Translational Control. Cold Spring Harbor, N.Y.: Cold Spring Harbor Press; 1996; 31-67). EIF3 appears to play a central role in the initiation by interaction with numerous other translational components (Vornlocher et al., 1999, J. Biol. Chem., Vol. 274, Issue 24, 16802-16812). The functions of each subunit are still poorly understood. High levels of expression of certain subunits are detected in tumors such as p150, p170; it has been proposed that p170 plays another role in addition to its functions in the initiation of translation (Lin et al., 2001, J. Cell Biochem., 80(4): 483-90; Pincheira et al., 2000, Eur. J. Cell Biol., 80(6): 410-8). Overexpression of subunit 8 (p110) has also been demonstrated in a tumor of the germinal cells by Roche et al. (2000, American Journal of Pathology, 157: 1597-1604) which suggests a role of this subunit in the development of the tumor by augmenting translation in general, leading to augmented growth and cell division.

No implication in the regulation of angiogenesis of subunit 8 of EIF3 nor of its similar protein have been reported to date.

The control of angiogenesis thus represents a strategic axis both for fundamental research (in order to improve the comprehension of numerous pathological phenomena linked to angiogenesis) and for the development of new therapies intended to treat pathologies linked to angiogenesis.

In order to control angiogenesis, multiple pharmaceutical groups have therefore developed therapeutic strategies based directly on the use of paracrine stimulatory and inhibitory factors as agents for promoting or inhibiting angiogenesis. These strategies are based essentially on the use of such factors in their polypeptide form as stimulatory or inhibitory agents of angiogenesis, or more recently in the form of expression vectors coding for the selected factors.

SUMMARY

The disclosure pertains to compositions comprising sequences of new genes, the function of which had not been identified to date. The implication of these genes in the angiogenesis mechanism has been demonstrated for the first time by the Applicant. Other gene sequences, at least one function of which had been previously identified, but for which the implication in the angiogenesis mechanism was demonstrated for the first time by the Applicant are also described. These genes are identified by their nucleotide sequences in the attached sequence listing. The disclosure also pertains to the polypeptide sequences of the factors coded by said genes, which find their application in the clinical study of the angiogenesis process, the prognosis, diagnosis and treatment of pathologies linked to this process, as well as in the implementation of pharmacological, pharmacogenomic, and drug identification trials.

We thus provide to a pharmaceutical composition comprising a pharmaceutically acceptable carrier and an active agent, comprising at least one substance selected from the group consisting of (i) a nucleic acid molecule, the expression of which is induced in an endothelial cell by an angiostatic agent, or a complementary sequence or a fragment of the nucleic acid molecule; (ii) a polypeptide sequence coded by the nucleic acid molecule or a fragment thereof; (iii) an antisense nucleic acid molecule that inhibits the expression of a nucleic acid molecule according to (i); and (iv) an antibody capable of binding to a polypeptide sequence according to (ii).

We also provide an antibody that has an affinity for one or more of the polypeptide sequences identified by SEQ ID No. 6 to SEQ ID No. 10 or by SEQ ID No. 31 to SEQ. ID No. 34, or fragments thereof.

We further provide a pharmaceutical composition comprising a pharmaceutically acceptable carrier and an active compound comprising one or more antibodies.

We still further provide an antisense nucleic acid sequence comprising at least 10 contiguous nucleotides of a nucleotide sequence selected from among the sequences identified by the numbers SEQ. ID No. 1 to SEQ II) No. 5, SEQ ID No. 12 to SEQ ID No. 14, and SEQ ID No. 27 to SEQ ID No. 30.

We also further provide a mammalian expression vector comprising at least one antisense sequence.

We also provide a method for the preparation of a genetically modified cell underexpressing a gene implicated in an angiogenic disorder, comprising inserting the vector into a mammalian cell.

We also provide a genetically modified cell, wherein the cell overexpresses at least one gene implicated in angiogenesis, and wherein the gene is identified by a nucleotide sequence selected from among the group of sequences identified by the numbers SEQ ID No. 1 to SEQ ID No. 5 and SEQ ID No. 27 to SEQ ID No, 30, or fragments thereof.

This disclosure further still relates to a pharmaceutical composition comprising a genetically modified cell and a pharmaceutically acceptable carrier.

We also provide a method for the preparation of a recombinant protein, comprising the steps of a) constructing an expression vector comprising at least one sequence selected from those identified by the numbers SEQ ID No. 1 to SEQ ID No. 5 and SEQ ID No. 27 to SEQ ID No. 30, or fragments thereof; b) introducing the vector into a cellular host; c) culturing the cells in a suitable medium; and d) purifying, the expressed protein so that the recombinant protein or a fragment thereof is expressed.

We also provides a method for the diagnosis and/or prognosis of an angiogenic pathology in a mammal, comprising detecting in cells isolated from the mammal the overexpression or the underexpression of one or more polypeptide sequences identified by the numbers SEQ ID No. 6 to SEQ ID No. 10 or SEQ ID No. 31 to SEQ ID No. 34, or fragments thereof.

We also provide a method for the verification of the therapeutic efficacy of an angiogenic treatment in a mammal, including identifying in vitro in a cell population from the mammal, the overexpression or the underexpression of at least one gene implicated in an angiogenic disorder, wherein, the gene is identified by one of the nucleotide sequences identified by the numbers SEQ ID No. 1 to SEQ ID No. 5 and SEQ ID No. 27 to SEQ ID No. 30.

We also provide a method for screening for compounds useful for the treatment of an angiogenic disorder of a mammal, comprising a) detecting the expression of at least one nucleotide sequence identified by SEQ ID No. 1 to SEQ ID No. 5 and SEQ ID No. 27 to SEQ ID No. 30 in a mammalian cell population contacted with a test compound; b) detecting the expression of the at least one nucleotide sequence in a reference cell population, the angiogenic state of which is known; and c) identifying the differences in the level of expression of the nucleotide sequences in the mammalian and reference cell populations, wherein a difference in expression of the nucleotide sequences in the mammalian and reference cell population indicates that the test compound has a therapeutic effect on an angiogenic disorder.

We also provide a device comprising a support comprising one or more specific probes of one or more nucleotide sequences identified by the numbers SEQ ID No. 1 to SEQ ID No. 5 and SEQ ID No. 27 to SEQ ID No. 30.

We also provide a kit for measuring the differential display of genes implicated in angiogenic disorders, comprising a device comprising a support comprising one or more specific probes of one or more nucleotide sequences; and specific primers and accessories required for the amplification of nucleotide sequences extracted from a sample, hybridization of such nucleotide sequences with the probes, and the performance of differential display measurements.

Figure 1A:
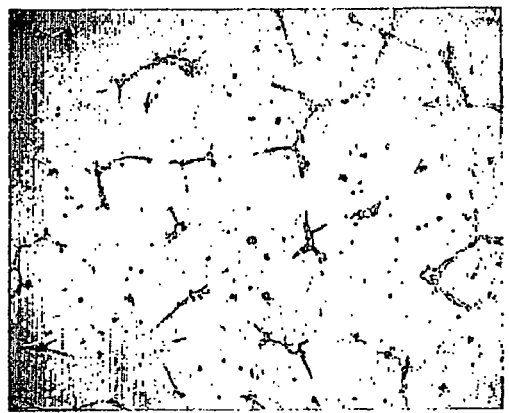
FIGS. 1A-E are a photomicrographs of a human endothelial cell cultures showing capillary tube formation upon transfection of cells with the following expression vectors.

1A) GS-V1 coding for the specific antisense transcript of GS-N1;

1B) GS-V2 coding for the specific antisense transcript of GS-N2;

1C) GS-V3 coding for the specific antisense transcript of GS-N3;

1D) GS-V4 coding for the specific antisense transcript of GS-N4 and its homologue GS-N5; and 1E) empty vector (control).

DETAILED DESCRIPTION

A method for the identification of new genes implicated in the regulation of angiogenesis has been developed. This method was the object of a French patent application published as FR no. 2798674 and of an International patent application published as WO 01/218312, the entire disclosures of which are herein incorporated by reference. This method has the distinctive characteristic of faithfully translating the innermost mechanisms regulating angiogenesis, taking into account all of the extracellular factors described as regulatory agents of angiogenesis; the angiogenic factors and angiostatic factors as well as the different components of the extracellular matrix. This method consists of bringing to bear these different extracellular factors via four clearly defined experimental conditions, in which endothelial cells are cultured on a component and/or on a clearly defined mixture of multiple components of the extracellular matrix and placed under the four experimental conditions, i.e.:

A control condition in which the endothelial cells are not stimulated.

An angiogenic condition in which the endothelial cells are stimulated by one or more angiogenic factors.

An angiogenesis inhibition condition in which the endothelial cells are stimulated by one or more angiogenic factors and brought into the presence of one or more angiostatic conditions.

Another control condition in which the endothelial cells are stimulated by one or more angiostatic factors.

By means of these four conditions, it is possible to obtain mRNA preparations specific of angiogenesis, i.e., of the angiogenic state and/or the inhibition of angiogenesis, and to make it possible to detect genes coding for the cellular constituents implicated in the regulation of angiogenesis, including positive regulators and negative regulators. Thus, the method described above enables the systematic screening of all of the angiogenic and angiostatic factors, as well as the different components of the extracellular matrix, for the purpose of revealing and identifying the genes coding for the cellular constituents implicated in the regulation of angiogenesis. Moreover, given that the gene expression can be analyzed all along the pathway of the formation of neovessels by endothelial cells, this approach constitutes an in vitro methodology making it possible to link the gene expression with the biological functional parameters of angiogenesis.

The identification of the five genes reported below was performed according to the above-described method, using the angiogenic and angiostatic factors as well as type I collagen as component of the extracellular matrix, in order to reproduce the four experimental conditions.

The five genes identified by the sequences SEQ ID No. 1 to SEQ ID No. 5 in the attached sequence listing are implicated in the regulation mechanism of angiogenesis.

We demonstrated that the stimulation of endothelial cells by an angiostatic factor leads to the expression of genes coding for the cellular constituents implicated in the promotion of angiogenesis.

Thus, the stimulation of endothelial cells by an angiogenic factor or an angiostatic factor can induce expression of both positive and negative regulators of angiogenesis in those cells.

The disclosure more particularly pertains to a pharmaceutical composition active on angiogenesis phenomena, comprising a pharmaceutically acceptable carrier and an active agent comprising at least one substance selected from among: (i) a nucleic acid molecule from a gene of an endothelial cell, the expression of which is induced by an angiostatic factor, or a complementary sequence or a fragment or derivative thereof; (ii) a polypeptide sequence coded by (i); and (iii) a molecule capable of inhibiting the expression of a nucleic acid molecule according to (i) or of binding to a polypeptide sequence according to (ii).

Pharmaceutical compositions of the disclosure can be for human or veterinary use, and are preferably sterile and pyrogen free. Pharmaceutical compositions of the disclosure comprise, in addition to at least one active ingredient, at least one pharmaceutically acceptable carrier. Suitable pharmaceutically acceptable carriers include water (e.g., sterile water for injection); saline solutions such as physiological saline or phosphate buffered saline (PBS); polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; stabilizing or preservative agents, such as sodium bisulfite, sodium sulfite and ascorbic acid, citric acid and its salts, ethylenediaminetetraacetic acid, benzalkonium chloride, methyl- or propylparaben chlorobutanol; and combinations thereof.

According to one particular embodiment, the pharmaceutical composition of the disclosure comprises as an active compound at least one nucleotide sequence selected from among the group of nucleotide sequences identified by numbers SEQ ID No. 1 to SEQ ID No. 5 and SEQ ID No. 27 to SEQ ID No. 30 in the attached sequence listing, their complementary sequences and their corresponding antisense sequences, car one of their fragments or derivatives.

In the context of our disclosure, the term "equivalent sequences" (also called "derivative sequences" or "derivatives") with respect to the present nucleic acid sequences includes nucleotide sequences presenting minor structural modifications not modifying, their function, such as deletions, mutations or additions of bases, the identity of which is at least about 90%, for example at least about 95%, at least about 98%, or at least about 99%, with the nucleotide sequences identified by the numbers SEQ ID No. 1 to SEQ ID No. 5, and SEQ ID No. 27 to SEQ ID No. 30 in the attached sequence listing. One skilled in the art can readily identify derivatives of the present nucleic acids by testing them for the ability to regulate angiogenesis in the human endothelial cell culture assays described in the "Examples" section below. As used herein, "fragments" of the present nucleic acids comprise a smaller, contiguous sequence of nucleotides found within a larger nucleic acid sequence.

According to another embodiment, the pharmaceutical composition of the disclosure comprises at least one angiogenesis inhibitory sequence.

According to one embodiment the pharmaceutical composition of the disclosure comprises one or more angiogenesis inhibitory sequences comprising an antisense sequence of at least one sequence selected from among SEQ ID No. 1, to SEQ ID No. 5 and SEQ ID No. 27 to SEQ ID No. 30 in the attached sequence listing, or fragments or derivatives thereof.

The pharmaceutical composition of the disclosure preferably comprises one or more antisense sequences selected from among SEQ ID No. 11 to SEQ ID No. 14 in the attached sequence listing.

We also provide a pharmaceutical composition intended for the diagnosis, prognosis and/or treatment of pathologies linked to angiogenesis, characterized in that it comprises at least one polypeptide sequence selected from among the polypeptide sequences identified by the numbers SEQ ID No. 6 to SEQ ID No. 10 or among the polypeptide sequences identified by the numbers SEQ ID No. 31 to SEQ ID No. 34 in the attached sequence listing, or their fragments or derivatives.

In the context the disclosure, the term "equivalent sequences" with respect to the present polypeptide sequences (also called "derivative sequences" or "derivatives") should be understood to encompass polypeptide sequences presenting minor structural modifications not modifying their function, such as deletions, mutations or additions of amino acid residues, the identity of which is at least about 85%, preferably at least about 90%, for example at least about 95%, at least about 98% or at least about 99%, with the polypeptide sequences identified by the numbers SEQ ID No. 6 to SEQ ID No. 10 or with the polypeptide sequences identified by the numbers SEQ ID No. 31 to SEQ ID No. 34 in the attached sequence listing. One skilled in the art can readily identify derivatives of the present polypeptides by testing them for the ability to regulate angiogenesis in the human endothelial cell culture assays described in the "Examples" section below. As used herein, "fragments" of the present polypeptides comprise a smaller, contiguous sequence of amino acids found within a larger polypeptide sequence.

We also provide a pharmaceutical composition intended for the diagnosis, prognosis and/or treatment of pathologies linked to angiogenesis comprising at least one antagonist of one or more of the above-mentioned polypeptide sequences.

As used herein, the term "antagonist" is understood to mean any compound inhibitory of the biological activity of said polypeptide sequences in the angiogenesis mechanism, for example as measured by the endothelial cell culture assays described in the "Examples" section below.

Suitable antagonists comprise antibodies having an affinity for the present polypeptide sequences.

The disclosure also pertains to antibodies having an affinity for each of the poly-peptide sequences identified by the numbers SEQ ID No. 6 to SEQ ID No. 10 or with the polypeptide sequences identified by the numbers SEQ ID No. 31 to SEQ ID No. 34 in the attached sequence listing, or for one of their fragments or derivatives, as well as pharmaceutical compositions containing them.

The antibodies of the disclosure can be obtained from an immunocompetent cell of an animal by any in vivo or in vitro immunization method, notably an immunocompetent cell from a vertebrate and preferably a mammal, with any one of the polypeptide sequences identified by the numbers SEQ ID No. 6 to SEQ ID No. 10 or with the polypeptide sequences identified by the numbers SEQ ID No. 31 to SEQ ID No. 34 in the attached sequence listing, or one of their fragments or derivatives conserving the immunogenicity of the total protein. Suitable immunization methods that can be used to produce antibodies of the disclosure are within the skill in the art; see, e.g., Kohler G. and Milstein C., Nature 1975 Aug. 7; 256(5517): 495-497, the entire disclosure of which is herein incorporated by reference.

The antibodies of the disclosure can be polyclonal or monoclonal antibodies.

The disclosure also pertains to a pharmaceutical or diagnostic composition comprising one or more antibodies having an affinity for one or more of the polypeptide sequences identified by the numbers SEQ ID No. 6 to SEQ ID No. 10 or with the polypeptide sequences identified by the numbers SEQ ID No. 31 to SEQ ID No. 34, or by one of their fragments or derivatives conserving this affinity or prepared as indicated above.

We also provide antisense nucleotide sequences identified by the numbers SEQ ID No. 1 to SEQ ID No. 5 and SEQ ID No. 27 to SEQ ID No. 30 in the attached sequence listing.

In the context of our disclosure, the term "antisense sequence" is understood to mean any DNA sequence of at least 10 contiguous nucleotides complementary to at least a portion of an mRNA, which inhibits its expression of that mRNA; i.e., inhibits its translation into a protein.

The antisense sequences of the disclosure can have an identity of at least about 80%, at least about 85% or at least about 90%, preferably at least about 95%, and more preferably at least about 99%, with a sequence selected from among the sequences identified by the numbers SEQ ID No. 11 to SEQ. ID No. 14 in the attached sequence listing.

We also provides provide a mammalian expression vector comprising at least one antisense sequence as defined above for expression of the antisense sequence.

According to a preferred embodiment, said mammalian expression vector comprises at least one antisense sequence of at least one of the sequences identified by the numbers SEQ ID No. 1 to SEQ ID No. 5 and SEQ ID No. 27 to SEQ ID No. 30, or fragments or derivtives thereof, in the attached sequence listing, as well as a promoter which enables expression of said antisense DNA.

Said vector is more particularly selected from among the group of vectors GS-V1 to GS-V4 identified by their sequence bearing the numbers SEQ ID No. 15 to SEQ ID No. 18 in the attached sequence listing.

Moreover, introduction of said antisense sequences identified by the numbers SEQ ID No. 11 to SEQ ID No. 14 in the attached sequence listing, or one of their derivatives, into the mammalian expression vectors and subsequent insertion of said vectors in mammalian cells enables production of cell lines underexpressing genes intervening in the angiogenesis mechanism.

We thus also provide a genetically modified cell comprising at least one of the vectors comprising antisense sequences for underexpressing at least one nucleotide sequence selected from among the sequences SEQ ID No. 1 to SEQ ID No. 5 and SEQ ID No. 27 to SEQ. ID No. 30 in the attached sequence listing.

We also provide a method for the preparation of such a genetically modified cell underexpressing a gene implicated in an angiogenic disorder, characterized in that it comprises the insertion into a mammalian cell of one of the previously described expression vectors.

Thus, for the construction of these vectors, specific primers are designated for each of the identified sequences. These primers comprise restriction sites at their ends that are not contained in the cloned fragment or present in the multiple cloning region of the expression vector.

Preferred primers are indicated in Table I and are identified by the sequence numbers SEQ ID No. 19 to SEQ ID No. 26 in the attached sequence listing.

We also provide a mammalian expression vector comprising at least one nucleotide sequence selected from among the group of sequences identified by the numbers SEQ ID No. 1 to SEQ ID No. 5 and SEQ ID No. 27 to SEQ ID No. 30 in the attached sequence listing, or one of their fragments or derivatives.

The expression vectors described above are useful for preparing therapeutic compositions intended for treatment by cell therapy of angiogenic disorders and, for verifying the efficacy of a treatment of an angiogenic disorder in a mammal, notably in a human being, or for verifying the functionality of genes possibly implicated in the angiogenesis mechanism in said mammal.

The disclosure also pertains to a method for the preparation of a genetically modified cell line stably expressing an expression vector, said vector comprising at least one antisense sequence of at least one of the sequences identified by the numbers SEQ ID No. 1 to SEQ ID No. 5 and SEQ ID No. 27 to SEQ No. 30 in the attached sequence listing or fragments or derivatives thereof, as well as a promoter which enables expression of said antisense DNA, comprising the following steps;

introducing at least one antibiotic resistance gene into said genetically modified cell;

b) culturing the cells obtained in step a in the presence of said antibiotic; and c) selecting the viable cells.

The disclosure also pertains to a genetically modified cell comprising at least one vector comprising a nucleotide sequence selected from among the group of sequences identified by the numbers SEQ ID No. 1 to SEQ ID No. 5 and SEQ ID No. 27 to SEQ ID No. 30 in the attached sequence listing, or one of their fragments or derivatives overexpressing said sequence.

The disclosure also pertains to a pharmaceutical composition intended for the diagnosis, prognosis and/or treatment of pathologies linked to angiogenesis, comprising as an active agent said genetically modified cell, and a pharmaceutically acceptable carrier, The disclosure thus pertains to a method for the preparation of a genetically modified cell line stably expressing an expression vector, said vector comprising at least one of the sequences identified by the numbers SEQ ID No. 1 to SEQ ID No. 5 and SEQ ID No. 27 to SEQ ID No. 30 in the attached sequence listing, or one of their fragments or derivatives, as well as a promoter which enable expression of said sequence, comprising the following steps:

a) introducing at least one antibiotic resistance gene into said genetically modified cell;

b) culturing the cells obtained in step a) in the presence of said antibiotic; and c) selecting the viable cells.

It is thus possible to isolate human cells and transfect them in vitro with at least one of the vectors defined above, which vectors comprise at least one of the sequences defined by the numbers SEQ ID No. 1 to SEQ ID No. 5 and SEQ ID No. 27 to SEQ ID No. 30, or one of their fragments or derivatives. These genetically modified cells can then be administered to a mammal, preferably to a human being.

The therapeutic compositions containing such cells can be administered in the form of simple cell suspensions, but they can also be encapsulated in a suitable device using, e.g., semipermeable membranes.

We also provide a method for preparing a protein encoded by at least one of the genes the sequences of which are identified by the numbers SEQ ID No. 1 to SEQ. ID No. 5 and SEQ ID No. 27 to SEQ ID No. 30 in the attached sequence listing, or one of their fragments or derivatives.

The proteins identified by the sequences SEQ ID No. 6 to SEQ ID No. 10 and SEQ ID No. 31 to SEQ ID No. 34 in the attached sequence listing, or their fragments or derivatives can be produced in the form of recombinant proteins in vitro by introducing into a suitable host a suitable expression vector. The proteins (or fragments or derivatives thereof) can then be purified and subsequently used as a therapeutic agent.

Such a method for the preparation of a recombinant protein comprises the following steps:

a) constructing an expression vector comprising at least one sequence from among those identified by the numbers SEQ ID No. 1 to SEQ ID No. 5 and SEQ ID No. 27 to SEQ ID No. 30 in the attached sequence listing or one of their fragments or derivatives;

b) introducing said vector into a cellular host;

c) culturing said cells in a suitable medium; and d) purifying the expressed proteins or one of their fragments or derivatives.

We also provide to a recombinant protein obtained by the above method.

We also provide a pharmaceutical composition comprising such a recombinant protein and a pharmaceutically acceptable carrier.

As an example, expression systems of recombinant proteins in bacteria such as $E.\ coli$ can be used for expressing non-glycosylated proteins or polypeptides.

The coding sequence or a partial sequence of the gene of interest can be amplified by PCR using specific primers of this gene preferably with different restriction enzyme sites at their ends so as to enable the orientation of the amplified gene sequence in the expression vector. The amplified DNA is purified, then digested by the restriction enzymes and inserted by ligation into the expression vector previously digested by these same restriction enzymes. A large number of different vectors can be used, such as the vector pBR322 (Bolivar et al., Gene 2 (1977) 95-113, the entire disclosure of which is herein incorporated by reference) or its derivatives, containing, e.g., the promoter of the RNA polymerase of the bacteriophage T7 for a high level of expression, or the plasmid pET3a (Studier and Moffatt, 1986, J. Mol. Biol., 189(1): 113-30, the entire disclosure of which is herein incorporated by reference), preferably containing sequences coding for the selection markers (e.g., resistance to antibiotics), a multiple cloning site containing restriction enzyme sites suitable for the insertion of DNA. The cell/host system is preferably an inducible system such as that used for the in vivo radiotagging of the growth factor FGF2 (Colin et al., 1997, Eur. J. Biochem., 249, 473-480, the entire disclosure of which is herein incorporated by reference) and previously described by Patry et al. (1994, FEBS Lett., 349(1): 23-8, the entire disclosure of which is herein incorporated by reference); it can also contain a region coding for a polyhistidine tail at the end of the polypeptide of interest in order to facilitate purification.

The amplified DNA can be ligated in the plasmid, which is then transformed into the bacterium according to the method described by Sambrook et al. (1989, Molecular Cloning: A Laboratory Manual, $2^{nd}$ ed., Cold Spring Harbor Laboratory Press, Cold Spring Harbor, N.Y.). The transformed cells were spread on LB agar medium containing the antibiotics, the colonies resistant to the antibiotics were then controlled by PCR and then analyzed on gel. The plasmid DNA can then be isolated then sequenced to confirm the construction of the vector. Other suitable methods for producing recombinant protein are known in the art. For example, the production and purification of the recombinant protein can be performed as described (Patry et al., 1994, FEBS Lett., 349(1): 23-8, 473-480, the entire disclosure of which is herein incorporated by reference).

In brief, an isolated colony is inoculated in the liquid culture medium such as LB broth medium with the addition of the antibiotics. After incubation overnight, the preculture can be used to seed a culture of a larger volume. The expression of the polypeptide was then induced, the cells developed over several hours and were then collected by centrifugation. The cellular deposit can by lysed by chemical agents known in the art or mechanically, e.g., by sonication. The protein can be purified by means of its physicochemical properties as described for the purification of recombinant FGF2 (Colin et al., 1997, Eur. J. Biochem., 249, 473-480, the entire disclosure of which is herein incorporated by reference) or, if the protein is tagged with a polyhistidine tail, it can be purified via this tail by immobilization on a metallic ion chelator support as described (Tang et al., Protein Expr. Purif. 1997 Dec. 11(3): 279-83, the entire disclosure of which is herein incorporated by reference).

As an example, eukaryotic recombinant protein expression systems (e.g., from yeasts, plants, insects) for expressing polypeptides having post-translational modifications such as glycosylation can be used.

Thus, the recombinant protein can be produced, e.g., in the yeast *Pichia pastoris* as described by Sreekrishna et al. (1988, J. Basic Microbiol., 28(4): 265-78, the entire disclosure of which is herein incorporated by reference). The amplified DNA can be introduced in the same manner described above after digestion and ligation in an expression vector of *Pichia pastoris*, preferably containing a sequence coding for a selection marker (Scorer et al., Biotechnology (NY), 1994 February; 12(2): 181-184, the entire disclosure of which is herein incorporated by reference). The protein can be either intracellular or secreted if the vector contains sequences for introducing into the expressed sequence a sequence coding for a secretion signal sequence such as, e.g., the prepropeptide factor of *Saccharomyces cerevisiae* (Cregg et al., 1993; Scorer et al., 1993, the entire disclosure of which is herein incorporated by reference). A histidine tail can also be added to one of the ends of the recombinant protein in order to facilitate purification (Mozley et al., 1997, Photochem. Photobiol., 66(5): 710-5, the entire disclosure of which is herein incorporated by reference).

Said host is preferably selected from among: a bacterium, a yeast, an insect cell, a mammal cell, and a plant cell.

The administration of pharmaceutical compositions comprising recombinant proteins as described above can be implemented, e.g., via the topical, oral, intradermal, transdermal intra-ocular or intravenous route, or any other suitable enteral or parenteral route.

In the practice of our disclosure, the fragments of said proteins can be used as antagonists of the protein from which they originate. Thus, the suitable administration to an animal of a pharmaceutical composition comprising such fragments is recommended for inducing a diminution in the activity of said protein in the angiogenesis mechanism of a given pathology.

The disclosure also pertains to a method for the diagnosis and/or prognosis of an angiogenic pathology in a mammal, notably in a human being, consisting of detecting in the cells of said mammal the overexpression or the underexpression of one or more nucleotide sequences identified by the numbers SEQ ID No. 1 to SEQ ID No. 5 and SEQ ID No. 27 to SEQ ID No. 30 in the attached sequence listing.

Such a diagnostic and/or prognostic method comprises the following steps:
 detecting the expression of one or more of said nucleotide sequences SEQ ID No. 1 to SEQ ID No. 5 and SEQ ID No. 27 to SEQ ID No. 30 in a mammalian cell population;
 detecting the expression of the nucleotide sequences in a reference cell population, the angiogenic state of which is known; and
 identifying the differences in the level of expression of the nucleotide sequences in the two cell populations, wherein a difference in the expression of more nucleotide sequences in the mammalian and reference cell populations indicates the presence of, or susceptibility to, an angiogenic pathology in the mammal.

As used herein, a "cell population of a mammal" or "mammalian cell population" is a collection of mammalian cells of a certain type or lineage, or which are obtained from the same tissue or organ. It is understood that a cell population of a mammal can comprise different cell types; for example, when the population is obtained from the same tissue (e.g., blood) or organ (e.g., the liver). A cell population of a mammal can be obtained from both in vivo and in vitro (i.e., cultured cell) sources.

As used herein, a "reference cell population" is a collection of cells of a certain type or lineage, or which are obtained from the same tissue or organ, for which the angiogenic state is known. It is understood that a "reference cell population" can comprise different cell types, and can also be obtained from both in vivo and in vitro sources.

As used herein, a gene is "overexpressed" when that gene produces an amount of RNA and/or corresponding protein in a cell population of a mammal which is greater than the amount of RNA and/or corresponding protein produced from the same gene in a reference cell population.

As used herein, a gene is "underexpressed" when that gene produces an amount of RNA and/or corresponding protein in a cell population of a mammal which is less than the amount of RNA and/or corresponding protein produced from the same gene in a reference cell population.

The disclosure also pertains to a method for the diagnosis and prognosis of an angiogenic pathology in a mammal, notably in a human being, consisting of detecting in the cells of said mammal the overexpression or underexpression of one or more polypeptides identified by the numbers SEQ ID No. 6 to SEQ ID No. 10 or by the numbers SEQ ID No. 31 to SEQ ID No. 34 in the attached sequence listing.

According to a preferred embodiment, said method comprises the following steps:
 a) detecting the expression of one or more polypeptide sequences SEQ ID No. 6 to SEQ ID No. 10 or SEQ ID No. 31 to SEQ ID No. 34 in a mammalian cell population;
 b) detecting the expression of the polypeptide sequences in a reference cell population, the angiogenic state of which is known; and
 c) identifying the differences in the level of expression of the polypeptide sequences in the two cell populations, wherein a difference in expression of the polypeptide sequences in the mammalian and reference cell populations indicates the presence of, or susceptibility to, an angiogenic pathology in the mammal.

According to one particular embodiment, in the diagnostic and prognostic method of our disclosure, the detection of expression of the sequences is performed after having contacted the endothelial cells with a biological fluid obtained from a patient.

The disclosure also pertains to a method for the verification of the therapeutic efficacy of an angiogenic treatment in a mammal, notably in a human being, by the identification of a cell population in said mammal that overexpresses or underexpresses one or more nucleotide sequences identified by the numbers SEQ ID No. 1 to SEQ ID No. 5 and SEQ ID No. 27 to SEQ ID No. 30 in the attached sequence listing.

Such a method for the verification of therapeutic efficacy can comprise the following steps:
 detecting the expression of one or more of said nucleotide sequences SEQ ID No. 1 to SEQ ID No. 5 and SEQ ID No. 27 to SEQ ID No. 30 by a cell population from a mammal contacted with a test compound intended to treat an angiogenic disorder. As used herein, such a test compound is a compound which is suspected or is capable of having, or which has, a therapeutic effect on an angiogenic pathology;
 detecting the expression of the nucleotide sequences in a reference cell population, the angiogenic state of which is known; and identifying the differences in the level of expression of the nucleotide sequences in the two cell populations, wherein a difference in expression of the nucleotide sequences in the mammalian and reference cell populations indicates that the test compound has therapeutic efficacy.

According to a preferred embodiment, the verification method is performed on a cell population from a mammal in vivo, ex-vivo or on a cell population isolated from said mammal in vitro.

According to one particular embodiment, in the verification method of the disclosure, the detection of the expression of the sequences is performed after having contacted the endothelial cells with a biological fluid from a patient.

The disclosure also pertains to a method for screening for compounds useful for the angiogenic treatment of a mammal, notably a human being.

According to one preferred embodiment, such a screening method comprises the following steps:
  detecting the expression of one or more of said nucleotide sequences SEQ ID No. 1 to SEQ ID No. 5 and SEQ ID No. 27 to SEQ ID No. 30 in a mammalian cell population contacted with a test compound suspected of or capable of having, or which has, a therapeutic effect on an angiogenic pathology;
  detecting the expression of the nucleotide sequences in a reference cell population, the angiogenic state of which is known; and
  identifying the differences in the level of expression of the nucleotide sequences in the two cell populations, wherein a difference in expression of nucleotide sequences in the mammalian and reference cell populations indicates that the test compound has a therapeutic effect on an angiogenic pathology.

According to another preferred embodiment, such a screening method also comprises the following steps:
  detecting the expression of one or more of said polypeptide sequences identified by the numbers SEQ ID No. 5 to SEQ ID No. 10 or with the polypeptide sequences identified by the numbers SEQ ID No. 31 to SEQ ID No. 34 in the attached sequence listing in a cell population contacted with a test compound suspected of or capable of having, or which has, a therapeutic effect on an angiogenic pathology;
  detecting the expression of the polypeptide sequences in a reference cell population, the angiogenic state of which is known, and
  identifying the differences in the level of expression of the polypeptide sequences in the two cell populations, wherein a difference in expression of polypeptide sequences in the mammalian and reference cell populations indicates that the test compound has a therapeutic effect on an angiogenic disorder.

According to one particular embodiment of the screening method of our disclosure, the detection of the expression of the sequences is performed after having contacted the endothelial cells with a biological fluid from a patient.

As used herein, a compound has a "therapeutic effect" or "therapeutic efficacy" on an angiogenic pathology when, upon administration of that compound to an individual suffering from an angiogenic pathology, the symptoms of the angiogenic pathology are lessened, prevented or otherwise alleviated, or the growth of new blood vessels in the region of the angiogenic pathology is slowed or halted. In the practice of the present method, it is understood that a test compound which causes a difference in the expression of nucleotide sequences between a cell population of a mammal and a reference population indicates that the test compound has a therapeutic effect on an angiogenic pathology.

The following can be cited among the angiogenic disorders (also called "angiogenic pathologies") that could be diagnosed or treated with the pharmaceutical compositions of the disclosure: tumor vascularization, retinopathies (e.g., diabetic retinopathy), rheumatoid arthritis, Crohn's disease, atherosclerosis, hyperstimulation of the ovary, psoriasis, endometriosis associated with neovascularization, restenosis due to balloon angioplasty, tissue overproduction due to cicatrization, peripheral vascular disease, hypertension, vascular inflammation, Raynaud's disease and phenomena, aneurism, arterial restenosis, thrombophlebitis, lymphangitis, lymphedema, tissue cicatrization and repair, ischemia, angina, myocardial infarction, chronic heart disease, cardiac insufficiencies such as congestive heart failure, age-related macular degeneration and osteoporosis.

We also provide a device comprising a support comprising one or more specific probes of one or more nucleotide sequences identified by the numbers SEQ ID No. 1 to SEQ ED No. 5 and SEQ ID No. 27 to SEQ ID No. 30 in the attached sequence listing, or fragments or derivatives thereof, for the implementation of the screening method.

In the framework of our disclosure, the term "probe" is understood to mean any single-stranded DNA fragment, the sequence of which is complementary to a targeted sequence: this sequence can be detected by hybridization with the tagged sequence (tagged by radioactive atoms or fluorescent groups) which play the role of a molecular "fish hook."

According to a preferred embodiment, the support of said device is selected from among a glass membrane, a metal membrane, a polymer membrane and a silica membrane.

Such devices can comprise, e.g., DNA chips comprising one or more nucleotide sequences identified by the numbers SEQ ID No. 1 to SEQ ID No. 5 and SEQ ID No. 27 to SEQ ID No. 30 in the attached sequence listing, or fragments or derivatives thereof.

We also provide a kit for measuring the differential display of genes implicated in angiogenic disorders, comprising a device as previous described, specific primers and the accessories required for the amplification of sequences extracted from a sample, their hybridization with the probes of the device, and the performance of the measurements of the differential display.

We also provide a kit intended for the measurement of the differential display of genes implicated in angiogenic disorders, comprising a line of genetically modified cells stably expressing a vector expressing at least one of the nucleotide sequences identified by the numbers SEQ ID No. 1 to SEQ ID No. 5 and SEQ ID No. 27 to SEQ ID No. 30 in the attached sequence listing, or one of their fragments, or derivatives, as a reference cell population and the means necessary for the measurement of said differential display.

We also provide a kit intended for the measurement of the differential display of genes implicated in angiogenic disorders, comprising a line of genetically modified cells stably expressing a vector expressing at least one antisense sequence of one of the nucleotide sequences identified by the numbers SEQ ID No. 1 to SEQ ID No. 5 and SEQ ID No. 27 to SEQ ID No. 30 in the attached sequence listing, or one of their fragments or derivatives, as a reference cell population, and the means necessary for the measurement of said differential display.

Verification of the implication of the five identified genes and their homologues in the angiogenesis mechanism was performed according to the methodology described in the Materials and Methods section.

This verification is further illustrated by means of the attached FIG. 1, which shows the results obtained on the formation of capillary tubes on human endothelial cells under the effect of the expression of the vectors GS-V1, GS-V2, GS-V3 and GS-V4:

FIG. 1A shows that the formation of capillary tubes is inhibited in endothelial cells transfected with the vector GS-V1 coding for the specific antisense transcript of GS-N1.

Figure 1B:
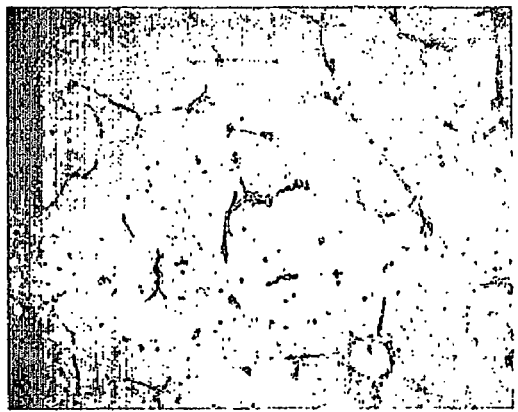

FIG. 1B shows that the formation of capillary tubes is inhibited in endothelial cells transfected with the vector GS-V2 coding for the specific antisense transcript of GS-N2.

Figure 1C:

FIG. 1C shows that the formation of capillary tubes is inhibited in endothelial cells transfected with the vector GS-V3 coding for the specific antisense transcript of GS-N3.

Figure 1D:
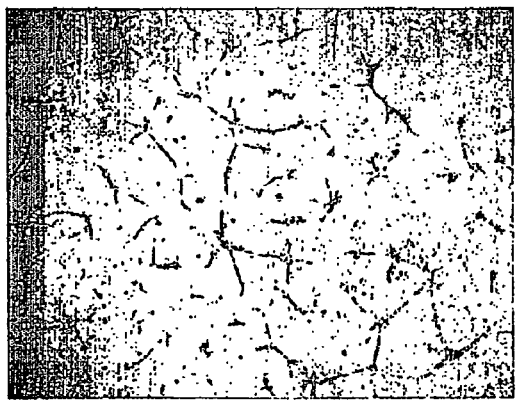

FIG. 1D shows that the formation of capillary tubes is inhibited in endothelial cells transfected with the vector GS-V4 coding for the specific antisense transcript of GS-N4 and its homologue GS-N5.

Figure 1E:
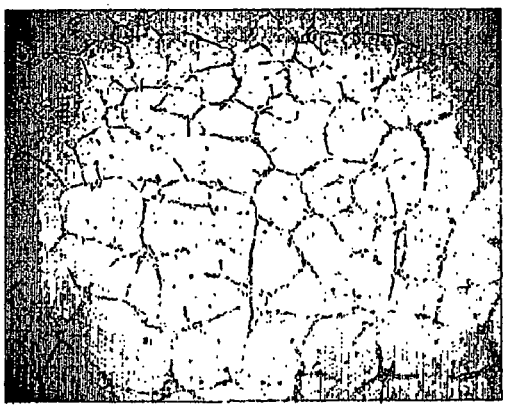

FIG. 1E shows that the formation of capillary tubes is not modified by endothelial cells transfected with the empty vector (control).

Our disclosure will now be illustrated by the following non-limiting examples. Throughout the Examples, certain suitable or preferred embodiments or elements of the disclosure beyond those which were employed in the Examples are indicated.

EXAMPLES

Material and Methods

1. Culture of the Cells and Angiogenesis Test

Human endothelial cells from umbilical veins (HUVEC) grown under the following four culture conditions (see WO 01/218312, supra) were used for identifying the genes coding for the cellular constituents implicated in the regulation of angiogenesis:

A control condition in which the endothelial cells are not stimulated.

An angiogenic condition in which the endothelial cells are stimulated by one or more angiogenic factors.

An angiogenesis inhibition condition in which the endothelial cells are stimulated by one or more angiogenic factors and brought into the presence of one or more angiostatic conditions.

Another control condition in which the endothelial cells are stimulated by one or more angiostatic factors.

The endothelial cells were maintained in complete medium (EGM-2-MV from Clonetics).

For the identification of the genes implicated in angiogenesis in the in vitro angiogenesis test according to the model of Montesano et al. (1986, Proc. Natl. Acad. Sci. USA, 83(19), 7297-301, the entire disclosure of which is herein incorporated by reference), the cells were first cultured on a collagen type I gel in complete medium until confluence. The reference HUVEC cells were then cultured in serum-poor medium without growth factors: EBM-2-MV+2% serum and different factors were added in the test conditions as follows.

FGF2: at concentrations comprised between 5 ng/ml and 60 ng/ml, preferably between 10 and 40 ng/ml; VEGF: at concentrations comprised between 10 ng/ml and 60 ng/ml, preferably comprised between 30 ng/ml and 50 ng/ml; PF4: at concentrations between 0.1 and 5 µg/ml, preferably between 0.5 µg/ml and 1 µg/ml; TNF-alpha: at concentrations comprised between 20 ng/ml and 100 ng/ml, preferably comprised between 30 ng/ml and 60 ng/ml; IFN-gamma: at concentrations comprised between 50 ng/ml and 200 ng/ml, preferably between 80 ng/ml and 120 ng/ml.

The human endothelial cells placed under the previously mentioned four culture conditions were then used to identify the genes coding for the cellular constituents implicated in the regulation of angiogenesis.

2. Angiogenic and Angiostatic Factors

The angiogenic and angiostatic factors which were found to have an effect on the expression of the genes identified in correlation with the formation of neovessels or the inhibition of neovessels respectively, are described below.

VEGF=vascular endothelial growth factor.
PF4=platelet factor 4.
TNF-$\alpha$=tumor necrosis factor alpha.

TNF-$\alpha$, which is a regulator of angiogenesis, can induce angiogenesis in vivo but also inhibit the formation of vessels in vitro (Frater-Schroder et al., 1987, Proc. Natl. Acad. Sci. USA, 84(15), 5277-81; Sato et al., 1987, J. Natl. Cancer Inst. 79(6), 1383-91; Fajardo et al., 1992, Am. J. Pathol. Mar, 140(3), 539-44; Niida et al., 1995, Neurol. Med. Chir. (Tokyo), 35(4), 209-14). In the in vitro model of angiogenesis used herein, TNF-$\alpha$ was used under angiogenesis inhibition conditions.

3. Comparison of the Gene Expression

Gene expression can then be compared using DNA chips, SAGE, quantitative PCR amplification reaction, viral vectors to construct subtractive banks or differential display analysis.

In the framework of the experimental studies supporting our disclosure, the Applicant preferentially used the differential display technique for the identification of said genes.

Differential Display

RNA was prepared from HUVEC cells cultured on a collagen gel in the presence of the different factors employed by means of the RNeasy Mini kit (Qiagen) method integrating a step of DNase I digestion as recommended by the manufacturer.

Differential display from the total RNAs was performed according to the method described by Liang and Pardee (1992, Science, 14; 257(5072), 967-7, the entire disclosure of which is herein incorporated by reference) using alpha_P33-ATP in isotopic dilution during the PCR amplification, for the visualization by autoradiography of the electrophoresis gels.

Thus, the DNA fragments differentially present on the gel as a function of the culture conditions analyzed were cut out, reamplified, cloned in a PGEM easy vector plasmid (Promega), sequenced and identified by querying the BLAST bank.

4. Verification of the Implication of the Identified Genes in the Angiogenesis Mechanism Functionality Test of the Genes In a second step, the functionality of each identified sequence was tested in the in vitro angiogenesis model, with endothelial cells transfected with an expression vector comprising an antisense oligonucleotide of said sequence.

For the construction of these vectors, specific primers for each of the identified sequences were designated. These primers are indicated in Table I below and identified with the numbers of SEQ ID No. 19 to SEQ ID No. 26 in the attached sequence listing.

TABLE I

| ID SEQ. of the identified gene | Name of primer |
|---|---|
| SEQ ID No. 1 (GS-N1) | GV1-1 |
|  | GV1-2 |
| SEQ ID No. 2 (GS-N2) | GV2-1 |
|  | GV2-2 |
| SEQ ID No. 3 (GS-N3) | GV3-1 |
|  | GV3-2 |
| SEQ ID No. 4 (GS-N4) | GV4-1 |
|  | GV4-2 |
| SEQ ID No. 5 (GS-N5) | GV5-1 |
|  | GV5-2 |

Each of these primers contain at their ends a different restriction enzyme site (SalI GTCGAC or MluI: ACGCGT).

Amplified fragments of each gene were obtained by PCR from bacterial plasmids containing the fragment of the identified gene using said primers.

These fragments were purified, digested by the restriction enzymes SalI and MluI and inserted in an expression vector of the type pCI-neo vector (Promega), which itself had been digested by these two restriction enzymes.

Each fragment was introduced into the vector in the antisense orientation.

Generally speaking, the vectors that could be used for the demonstration of the functionality of the identified genes in the angiogenesis mechanism comprise any expression vector systems in mammals comprising a promoter enabling expression of a cloned gene; for example, the strong promoter of the human cytomegalovirus (CMV).

Constitutive or inducible vectors capable of being used in the practice of our disclosure are indicated in the nonexhaustive list below:

The vectors pCI Mammalian Expression vector, Expression Vector System cloning vector pALTER®*-MAX (Promega), vectors pcDNA3.1, -/hygro, -/Zeo, pcDNA4/His-MAx, -E, pBudCE4, pRcRSV, pRcCMV2, pSecTag2, -/hygro secretion vectors, the vectors pEBVHis A, B and C) (Invitrogen), the expression vectors in mammals pIRES, pIRES-EYFP pIRES2-EGFP, pCMV-Myc and pCMV-HA, Epitope-Tagged pTRE, the vectors VP16 Minimal Domain (ptTA 2, ptTA 3 and ptTA 4), the expression vectors Tet bidirectional (pBI, pBI-EGFP, pBI-G, pBI-L), pRevTRE, pTRE2, pLEGFP-N1 Vector Retroviral pLEGFP-C1, the adenoviral expression systems Adeno-X, pCMS-EGFP, pdI-EGFP-N1, pd2ECFP-N1, pd2EYFP-N1, pEGFP(-C1, -C2, -C3, -N2, -N3), pEYFP-C1, -N1 (Clontech).

Each vector comprising said antisense fragment was then produced in E. coli, extracted, purified and quantified. One μg of each vector was incubated in the presence of a transfectant agent (Effectene, Qiagen) according to the protocol recommended by the manufacturer with the endothelial cells. Twenty-four hours after transfection, the endothelial cells were trypsinized and spread on the extracellular matrix containing the angiogenesis factors in Matrigel according to the model described by Grant et al. (1989, Cell, 58(5), 933-43, the entire disclosure of which is herein incorporated by reference). After 24 h of incubation, the formation of vessels was observed and compared to the control cells transfected with the empty mammalian expression vector.

5. Establishment of the Bank of Stable Lines Expressing the Expression Vectors Containing the Gene Sequences or their Fragments or their Antisense Sequences The expression systems can comprise an antibiotic selection marker (an antibiotic resistance gene) in order to select the transfected cells expressing in a stable manner the vector comprising the nucleic acid cloned in said vector either in this same vector or in a second co-transfected vector.

This expression vector can be a constitutive or inducible expression system.

In the particular example described below, the stable lines for the expression of the antisense oligonucleotide corresponding to each identified gene were obtained with a constitutive expression vector after selection in the presence of antibiotic.

In order to do this, 24 h after the transfection performed under the conditions described above, the BAEC endothelial cells were trypsinized and sown at the rate of 80,000 cells/well in six-well plates in the presence of 700 μg/ml of the antibiotic G418 (Promega). A control well was sown with non-transfected cells. The medium was changed every three days with a recharge of the antibiotic. The control cells were eliminated after 8 to 10 days. The cells resistant to the antibiotic were collected at confluence (after 2 to 3 weeks) then transferred to culture flasks still in the presence of the antibiotic. The stable lines were then tested for their capacity to form or not form vessels in the in vitro angiogenesis test.

6. Results 6.1 Identification of the Genes

The nucleic acid sequence designated GS-N1 and the protein coded by said nucleic acid sequence GS-N1 identified by the number SEQ ID No. 6, designated angiopartnerine, had not previously been identified as having any biological role, least of all a role in the angiogenesis process or the differentiation of endothelial cells into capillary tubes. The nucleic acid sequences designated GS-N2 to GS-N5 identified by the numbers SEQ ID No. 2 to SEQ ID No. 5 in the attached sequence listing and, respectively, the proteins coded by said nucleic acids identified by the numbers SEQ ID No. 7 to SEQ ID No. 10 in the attached sequence listing, had not previously been identified as having a biological role in the angiogenesis process or in the differentiation of endothelial cells into capillary tubes. These sequences are described below.

The previously described differential display method allowed identification of the following mRNAs:

GS-N1: a 6160-bp mRNA identified by the sequence SEQ ID No. 1 in the attached sequence listing. A BLAST search on the GENBANK sequence database identified it by the accession number AB037857.

The coding sequence of this mRNA has a partial coding sequence from nucleotide 1 to nucleotide 2777. There was thus identified a protein GS-P1 resulting from the translation of this RNA. This protein was composed of 924 aa, identified by the number SEQ ID No. 6 in the attached sequence listing, called angiopartnerine.

GS-N2: a 3266-bp mRNA identified by the sequence SEQ ID No. 2 in the attached sequence listing. A BLAST search of the GENBANK sequence database identified it as accession number AF247704.

The sequence of this mRNA has a coding sequence from nucleotide 49 to nucleotide 753. There was thus identified a protein GS-P2 resulting from the translation of this mRNA. This protein is composed of 234 aa, identified by the number SEQ ID No. 7 in the attached sequence listing; it is called protein homeobox NKX3.1.

G3-N3: a 6711-bp mRNA identified by the sequence SEQ ID No. 3 in the attached sequence listing. A BLAST search of the GENBANK sequence database identified it as accession number U91543.

The sequence of this mRNA has a coding sequence from nucleotide 151 to nucleotide 6153. There was thus identified a protein GS-P3 resulting from the translation of this mRNA. This protein is composed of 2000 aa, identified by the number SEQ ID No. 8 in the attached sequence listing, called zinc finger helicase.

GS-N4: a 3041-bp mRNA identified by the sequence SEQ ID No. 4 in the attached sequence listing. A BLAST search of the GENBANK sequence database identified it as accession number BC001571.

The sequence of this mRNA has a coding sequence from nucleotide 67 to nucleotide 2808. There was thus identified a protein GS-P4 resulting from the translation of this mRNA. This protein is composed of 913 aa, identified by the number SEQ ID No. 9 in the attached sequence listing, designated initiation factor of eukaryote translation, subunit 8 (110 kDa) (EIF3S8).

This sequence GS-N4 presents an homology with the following sequence:

GS-N5: a 1507-pb mRNA identified by the sequence SEQ ID No. 5 in the attached sequence listing. A BLAST search on the GENBANK sequence database identified it as accession number BC000533.

The sequence of this mRNA has a coding sequence from nucleotide 407 to nucleotide 1384. There was thus identified a protein GS-P5 resulting from the translation of this mRNA. This protein is composed of 325 aa, identified by the number SEQ ID No. 10 in the attached sequence listing, designated protein similar to the initiation factor of eukaryote translation, subunit 8 (110 kDa).

The expression of the above identified mRNAs is observed in human endothelial cells when the formation of capillary tubes, synonymous with angiogenesis, is inhibited following the action of an angiostatic factor.

The Applicant has demonstrated that the augmentation of the expression of the gene corresponding to each of these mRNAs accompanies the inhibition of the formation of neovessels by endothelial cells.

In fact, the human endothelial cells forming neovessels following stimulation by an angiogenic factor exhibit a very weak expression of these mRNAs, whereas the same human endothelial cells stimulated by the same angiogenic factor and contacted with an angiostatic factor (where angiogenesis is inhibited) and/or the same endothelial cells stimulated solely by the angiostatic factor, exhibit an elevated expression of this gene (as shown in Table II).

These results indicate the existence of a direct correlation between the expression of each of these genes and the angiostatic state (i.e., the inhibition of angiogenesis) of human endothelial cells.

TABLE II

| ID SEQ | Inducers of expression |
|---|---|
| SEQ ID No. 1 (GS-N1) | TNF-alpha |
| SEQ ID No. 2 (GS-N2) | TNF-alpha |
| SEQ ID No. 3 (GS-N3) | TNF-alpha |
| SEQ ID No. 4 (GS-N4) | PF4 |
| SEQ ID No. 5 (GS-N5) | PF4 |

6.2 Verification of the Role of the Identified Genes in the Regulation of Angiogenesis The functional role of the above-described genes in the formation of neovessels by human endothelial cells was also demonstrated.

In fact, a specific nucleotide sequence of each of the identified genes, selected from among the nucleotide sequences identified by the sequences SEQ ID No. 11 to SEQ ID No. 14, was introduced into the expression vector pCI-neo Vector in the antisense orientation.

The resultant vectors, designated GS-V1 to GS-V4 and identified by their sequences SEQ ID No. 15 to SEQ ID No. 18, were used to repress the expression of the gene coding for this mRNA in human endothelial cells following the transfection of these cells by these vectors.

The human endothelial cells were then stimulated by angiogenic factors. The results obtained for each of the sequences GS-N1 to GS-N5 using the antisense sequences and the corresponding vectors show that repression of the expression of the genes identified by the sequence numbers SEQ ID No. 1 to SEQ ID No. 5 inhibits the formation of neovessels by human endothelial cells.

The results obtained for each of the sequences using the antisense sequences and the corresponding vectors, indicated in Table III below, are further illustrated in FIGS. 1A to 1E.

TABLE III

| | Genes Name SEQ. ID | Proteins SEQ. ID | Antisense sequences | Vector with inserted antisense | FIG. | Control FIG. |
|---|---|---|---|---|---|---|
| 1 | SEQ ID No. 1 (GS-N1) | SEQ ID No. 6 (GS-P1) angiopartnerine | SEQ ID No. 11 (392 bp) | SEQ ID No. 15 (GS-V1) | 1A | 1F |
| 2 | SEQ ID No. 2 (GS-N2) | SEQ ID No. 7 (GS-P2) homeobox NFX3.1 | SEQ ID No. 12 (250 bp) | SEQ ID No. 16 (GS-V2) | 1B | 1F |
| 3 | SEQ ID No. 3 (GS-N3) | SEQ ID No. 8 (GS-P3) zinc finger helicase | SEQ ID No. 13 (bp) | SEQ ID No. 17 (GS-V3) | 1C | 1F |
| 4 | SEQ ID No. 4 (GS-N4) | SEQ ID No. 9 (GS-P4) initiation factor of eukaryote translation, subunit 8 e | SEQ ID No. 14 (167 bp) | SEQ ID No. 18 (GS-V4) | 1D | 1F |

TABLE III-continued

| Genes Name SEQ. ID | Proteins SEQ. ID | Antisense sequences | Vector with inserted antisense | FIG. | Control FIG. |
|---|---|---|---|---|---|
| 5 SEQ ID No. 5 (GS-N5) | SEQ ID No. 10 (GS-P5) initiation factor of eukaryote translation, subunit 8 | SEQ ID No. 14 (167 bp) | SEQ ID No. 18 (GS-V4) | 15 | |

A variety of modifications to the embodiments described will be apparent to those skilled in the art from the disclosure provided herein. Thus, our disclosure may be embodied in other specific corms without departing from the spirit or essential attributes thereof and, accordingly, reference should be made to the appended claims, rather than to the foregoing specification, as indicating the scope of the disclosure.

We claim:

1. A composition comprising:
   a pharmaceutically acceptable carrier selected from the group consisting of: phosphate buffered saline (PBS), polyethylene glycol, glycerin, propylene glycol, an antibacterial agent, an antioxidant, a chelating agent, an acetate buffer, a citrate buffer, an agent for the adjustment of tonicity, a stabilizing or preservative agent, and combinations thereof; and,
   at least one active agent that is a polypeptide wherein the polypeptide is selected from the group consisting of: the polypeptide identified by SEQ ID NO: 6 and the polypeptide identified by SEQ ID NO: 32.

2. The composition according to claim 1, wherein the composition comprises benzyl alcohol and methyl parabens as an antibacterial agent.

3. The composition according to claim 1, wherein the composition comprises ascorbic acid or sodium bisulfite as an antioxidant agent.

4. The composition according to claim 1, wherein the composition comprises a ethylenediaminetetraacetic acid as a chelating agent.

5. The composition according to claim 1, wherein the composition comprises sodium chloride chlorobutanol or dextrose as an agent for the adjustment of tonicity.

6. The composition according to claim 1, wherein the composition comprises at least one stabilizing or preservative agents selected from the group consisting of sodium bisulfite, sodium sulfite, ascorbic acid, citric acid and salts thereof, ethylenediaminetetraacetic acid, benzalkonium chloride, methyl propylparaben chlorobutanol and propylparaben chlorobutanol.

* * * * *